United States Patent
Kan et al.

(10) Patent No.: US 10,745,673 B2
(45) Date of Patent: Aug. 18, 2020

(54) HEME PROTEIN CATALYSTS FOR CARBON-BORON BOND FORMATION IN VITRO AND IN VIVO

(71) Applicant: California Institute of Technology, Pasadena, CA (US)

(72) Inventors: S. B. Jennifer Kan, Pasadena, CA (US); Xiongyi Huang, Pasadena, CA (US); Kai Chen, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/914,788

(22) Filed: Mar. 7, 2018

(65) Prior Publication Data
US 2018/0273917 A1    Sep. 27, 2018

Related U.S. Application Data

(60) Provisional application No. 62/467,909, filed on Mar. 7, 2017, provisional application No. 62/535,411, filed on Jul. 21, 2017.

(51) Int. Cl.
| | |
|---|---|
| C12P 17/12 | (2006.01) |
| C12P 17/10 | (2006.01) |
| C12N 9/02 | (2006.01) |
| C07K 14/195 | (2006.01) |

(52) U.S. Cl.
CPC .......... *C12N 9/0053* (2013.01); *C07K 14/195* (2013.01); *C12P 17/10* (2013.01); *C12P 17/12* (2013.01); *C12Y 109/03001* (2013.01)

(58) Field of Classification Search
CPC ........... C12N 9/0053; C12Y 109/03001; C12P 17/12; C12P 17/10
See application file for complete search history.

(56) References Cited

FOREIGN PATENT DOCUMENTS

WO   2016/191612 A2   12/2016

OTHER PUBLICATIONS

Witkowski et al., Biochemistry 38:11643-11650, 1999.*
Ang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Salemme, F., Ann Rev Biochem 46:299-329, 1997.*
Sirim et al., BMC Structural Biology 10:34, 2010.*
Bailly et al., FEBS Journal 274:2641-2652, 2007.*
Yuan et al., Microbiol Mol Biol Rev 69(3):373-392, 2005.*
Arnold. "The nature of chemical innovation: new enzymes by evolution." *Q Rev Biophys*, Nov. 2015, 4(4): 404-410.
Cheng, Q.-Q., Zhu, S.-F., Zhang, Y.-Z., Xie, X.-L. & Zhou, Q.-L. "Copper-catalyzed B—H bond insertion reaction: a highly efficient and enantioselective C—B bond-forming reaction with amine-borane and phosphine-borane adducts." *J. Am. Chem. Soc.* 135, 14094-14097 (2013).
Coelho, P. S. et al. "A serine-substituted P450 catalyzes highly efficient carbene transfer to olefins in vivo." *Nat. Chem. Biol.* 9, 485-487 (2013).
Curran, D. P. et al. "Synthesis and reactions of N-heterocyclic carbene boranes." *Angew. Chem. Int. Ed.* 50, 10294-10317 (2011).
Hernandez, K. E. et al. "Highly Stereoselective Biocatalytic Synthesis of Key Cyclopropane Intermediate to Ticagrelor." *ACS Catal.* 6, 7810-7813 (2016).
Hyster, T. K., et al. "Genetic optimization of metalloenzymes: Enhancing enzymes for non-natural reactions." *Angew. Chem. Int. Ed.* 55, 7344-7357 (2016).
International Search Report dated Jul. 28, 2017 for Intl. Pat. Appl. No. PCT/US18/21381.
Jeschek, M. et al. "Directed evolution of artificial metalloenzymes for in vivo metathesis." *Nature* 537, 661-665 (2016).
Kan, S. B. J., et al. "Directed evolution of cytochrome c for carbon-silicon bond formation: Bringing silicon to life." *Science* 354, 1048-1051 (2016).
Kan, S. B. J., et al. "Genetically programmed chiral organoboranes synthesis." *Science* 552, 132-136 (2017).
Kawamoto, T. et al. "Radical Reactions of N-Heterocyclic Carbene Boranes with Organic Nitriles: Cyanation of NHC-Boranes and Reductive Decyanation of Malononitriles." *J. Am. Chem. Soc.* 137, 8617-8622 (2015).
Li, X. et al. "Insertion of reactive rhodium carbenes into boron-hydrogen bonds of stable N-heterocyclic carbene boranes." *J. Am. Chem. Soc.* 135, 12076-12081 (2013).
Renata, H., et al. "Expanding the enzyme universe: accessing non-natural reactions by mechanism-guided directed evolution." *Angew. Chem. Int. Ed.* 54, 3351-3367 (2015).
Renata, H. et al. "Identification of mechanism-based inactivation in P450-catalyzed cyclopropanation facilitates engineering of improved enzymes." *J. Am. Chem. Soc.* 138, 12527-12533 (2016).
Stelter, M. et al. "A novel type of monoheme cytochrome c: biochemical and structural characterization at 1.23 Å resolution of Rhodothermus marinus cytochrome c." *Biochemistry* 47, 11953-11963 (2008).

(Continued)

*Primary Examiner* — Delia M Ramirez
(74) *Attorney, Agent, or Firm* — Kilpatrick Townsend & Stockton LLP

(57) ABSTRACT

Provided herein are methods for producing an organoboron product. The methods include combining a boron-containing reagent and a carbene precursor in the presence of a heme protein, e.g., a cytochrome c, a cytochrome P450, a globin, a protoglobin, a nitric oxide dioxygenase, a peroxidase, or a catalase, or a variant thereof, under conditions sufficient to form the organoboron product. Reaction mixtures for producing organoboron products are also described, as well as whole-cell catalysts comprising heme proteins and variants thereof for forming carbon-boron bonds.

11 Claims, 10 Drawing Sheets
Specification includes a Sequence Listing.

(56) References Cited

OTHER PUBLICATIONS

Würtemberger-Pietsch, S., et al. "25 years of N-heterocyclic carbenes: activation of both main-group element-element bonds and NHCs themselves." *Dalton Trans.* 45, 5880-5895 (2016).

\* cited by examiner 2,440 TTN, 96:4 e.r.

Gram-scale synthesis
2,910 TTN, 96:4 e.r., 42% isolated yield
(64% based on recovered starting material)

SEQUENCE LISTING

<160> NUMBER OF SEQ ID NOS: 25

<210> SEQ ID NO 1
<211> LENGTH: 124
<212> TYPE: PRT
<213> ORGANISM: Rhodothermus marinus

<400> SEQUENCE: 1

Thr Glu Ser Gly Thr Ala Ala Gln Asp Pro Glu Ala Leu Ala Ala Glu
1               5                   10                  15

Ile Gly Pro Val Lys Gln Val Ser Leu Gly Glu Gln Ile Asp Ala Ala
            20                  25                  30

Leu Ala Gln Gln Gly Glu Gln Leu Phe Asn Thr Tyr Cys Thr Ala Cys
        35                  40                  45

His Arg Leu Asp Glu Arg Phe Ile Gly Pro Ala Leu Arg Asp Val Thr
    50                  55                  60

Lys Arg Arg Gly Pro Val Tyr Ile Met Asn Val Met Leu Asn Pro Asn
65                  70                  75                  80

Gly Met Ile Gln Arg His Pro Val Met Lys Gln Leu Val Gln Glu Tyr
                85                  90                  95

Gly Thr Met Met Thr Asp Met Ala Leu Ser Glu Glu Gln Ala Arg Ala
            100                 105                 110

Ile Leu Glu Tyr Leu Arg Gln Val Ala Glu Asn Gln
        115                 120

<210> SEQ ID NO 2
<211> LENGTH: 104
<212> TYPE: PRT
<213> ORGANISM: Equus caballus

<400> SEQUENCE: 2

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro Asn Leu
            20                  25                  30

His Gly Leu Phe Gly Arg Lys Thr Gly Gln Ala Pro Gly Phe Thr Tyr
        35                  40                  45

Thr Asp Ala Asn Lys Asn Lys Gly Ile Thr Trp Lys Glu Glu Thr Leu
    50                  55                  60

Met Glu Tyr Leu Glu Asn Pro Lys Lys Tyr Ile Pro Gly Thr Lys Met
65                  70                  75                  80

Ile Phe Ala Gly Ile Lys Lys Lys Thr Glu Arg Glu Asp Leu Ile Ala
                85                  90                  95

Tyr Leu Lys Lys Ala Thr Asn Glu
            100

<210> SEQ ID NO 3
<211> LENGTH: 104
<212> TYPE: PRT
<213> ORGANISM: Homo sapiens

<400> SEQUENCE: 3

Gly Asp Val Glu Lys Gly Lys Lys Ile Phe Ile Met Lys Cys Ser Gln
1               5                   10                  15

Cys His Thr Val Glu Lys Gly Gly Lys His Lys Thr Gly Pro Asn Leu
            20                  25                  30

His Gly Leu Phe Gly Arg Lys Thr Gly Gln Ala Pro Gly Tyr Ser Tyr
        35                  40                  45

```
Thr Ala Ala Asn Lys Asn Lys Gly Ile Ile Trp Gly Glu Asp Thr Leu
         50                  55                  60

Met Glu Tyr Leu Glu Asn Pro Lys Lys Tyr Ile Pro Gly Thr Lys Met
 65                  70                  75                  80

Ile Phe Val Gly Ile Lys Lys Glu Glu Arg Ala Asp Leu Ile Ala
                 85                  90                  95

Tyr Leu Lys Lys Ala Thr Asn Glu
            100

<210> SEQ ID NO 4
<211> LENGTH: 106
<212> TYPE: PRT
<213> ORGANISM: Rhodopila globiformis

<400> SEQUENCE: 4

Gly Ser Ala Pro Pro Gly Asp Pro Val Glu Gly Lys His Leu Phe His
 1               5                  10                  15

Thr Ile Cys Ile Leu Cys His Thr Asp Ile Lys Gly Arg Asn Lys Val
             20                  25                  30

Gly Pro Ser Leu Tyr Gly Val Val Gly Arg His Ser Gly Ile Glu Pro
         35                  40                  45

Gly Tyr Asn Tyr Ser Glu Ala Asn Ile Lys Ser Gly Ile Val Trp Thr
 50                  55                  60

Pro Asp Val Leu Phe Lys Tyr Ile Glu His Pro Gln Lys Ile Val Pro
 65                  70                  75                  80

Gly Thr Lys Met Gly Tyr Pro Gly Gln Pro Asp Pro Gln Lys Arg Ala
             85                  90                  95

Asp Ile Ile Ala Tyr Leu Glu Thr Leu Lys
            100                 105

<210> SEQ ID NO 5
<211> LENGTH: 80
<212> TYPE: PRT
<213> ORGANISM: Hydrogenobacter thermophilus

<400> SEQUENCE: 5

Asn Glu Gln Leu Ala Lys Gln Lys Gly Cys Met Ala Cys His Asp Leu
 1               5                  10                  15

Lys Ala Lys Lys Val Gly Pro Ala Tyr Ala Asp Val Ala Lys Lys Tyr
             20                  25                  30

Ala Gly Arg Lys Asp Ala Val Asp Tyr Leu Ala Gly Lys Ile Lys Lys
         35                  40                  45

Gly Gly Ser Gly Val Trp Gly Ser Val Pro Met Pro Pro Gln Asn Val
 50                  55                  60

Thr Asp Ala Glu Ala Lys Gln Leu Ala Gln Trp Ile Leu Ser Ile Lys
 65                  70                  75                  80

<210> SEQ ID NO 6
<211> LENGTH: 414
<212> TYPE: PRT
<213> ORGANISM: Pseudomonas putida

<400> SEQUENCE: 6

Thr Thr Glu Thr Ile Gln Ser Asn Ala Asn Leu Ala Pro Leu Pro Pro
 1               5                  10                  15

His Val Pro Glu His Leu Val Phe Asp Phe Asp Met Tyr Asn Pro Ser
             20                  25                  30
```

```
Asn Leu Ser Ala Gly Val Gln Glu Ala Trp Ala Val Leu Gln Glu Ser
             35                  40                  45

Asn Val Pro Asp Leu Val Trp Thr Arg Cys Asn Gly Gly His Trp Ile
 50                  55                  60

Ala Thr Arg Gly Gln Leu Ile Arg Glu Ala Tyr Glu Asp Tyr Arg His
 65                  70                  75                  80

Phe Ser Ser Glu Cys Pro Phe Ile Pro Arg Glu Ala Gly Glu Ala Tyr
                 85                  90                  95

Asp Phe Ile Pro Thr Ser Met Asp Pro Glu Gln Arg Gln Phe Arg
            100                 105                 110

Ala Leu Ala Asn Gln Val Val Gly Met Pro Val Val Asp Lys Leu Glu
            115                 120                 125

Asn Arg Ile Gln Glu Leu Ala Cys Ser Leu Ile Glu Ser Leu Arg Pro
130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
            195                 200                 205

Glu Gln Arg Arg Gln Lys Pro Gly Thr Asp Ala Ile Ser Ile Val Ala
            210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 7
<211> LENGTH: 471
<212> TYPE: PRT
<213> ORGANISM: Bacillus megaterium

<400> SEQUENCE: 7
```

```
Thr Ile Lys Glu Met Pro Gln Pro Lys Thr Phe Gly Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415
```

```
Met Leu Lys His Phe Asp Phe Glu Asp His Thr Asn Tyr Glu Leu Asp
            420             425                 430

Ile Lys Glu Thr Leu Thr Leu Lys Pro Glu Gly Phe Val Val Lys Ala
            435             440                 445

Lys Ser Lys Lys Ile Pro Leu Gly Gly Ile Pro Ser Pro Ser Thr Glu
            450             455                 460

Gln Ser Ala Lys Lys Val Arg
465             470
```

<210> SEQ ID NO 8
<211> LENGTH: 133
<212> TYPE: PRT
<213> ORGANISM: Methylacidiphilum infernorum

<400> SEQUENCE: 8

```
Met Ile Asp Gln Lys Glu Lys Glu Leu Ile Lys Glu Ser Trp Lys Arg
1               5                   10                  15

Ile Glu Pro Asn Lys Asn Glu Ile Gly Leu Leu Phe Tyr Ala Asn Leu
            20                  25                  30

Phe Lys Glu Glu Pro Thr Val Ser Val Leu Phe Gln Asn Pro Ile Ser
            35                  40                  45

Ser Gln Ser Arg Lys Leu Met Gln Val Leu Gly Ile Leu Val Gln Gly
        50                  55                  60

Ile Asp Asn Leu Glu Gly Leu Ile Pro Thr Leu Gln Asp Leu Gly Arg
65                  70                  75                  80

Arg His Lys Gln Tyr Gly Val Val Asp Ser His Tyr Pro Leu Val Gly
                85                  90                  95

Asp Cys Leu Leu Lys Ser Ile Gln Glu Tyr Leu Gly Gln Gly Phe Thr
            100                 105                 110

Glu Glu Ala Lys Ala Ala Trp Thr Lys Val Tyr Gly Ile Ala Ala Gln
            115                 120                 125

Val Met Thr Ala Glu
        130
```

<210> SEQ ID NO 9
<211> LENGTH: 140
<212> TYPE: PRT
<213> ORGANISM: Campylobacter jejuni

<400> SEQUENCE: 9

```
Met Thr Lys Glu Gln Ile Gln Ile Ile Lys Asp Cys Val Pro Ile Leu
1               5                   10                  15

Gln Lys Asn Gly Glu Asp Leu Thr Asn Glu Phe Tyr Lys Ile Met Phe
            20                  25                  30

Asn Asp Tyr Pro Glu Val Lys Pro Met Phe Asn Met Glu Lys Gln Ile
            35                  40                  45

Ser Gly Glu Gln Pro Lys Ala Leu Ala Met Ala Ile Leu Met Ala Ala
        50                  55                  60

Lys Asn Ile Glu Asn Leu Glu Asn Met Arg Ser Phe Val Asp Lys Val
65                  70                  75                  80

Ala Ile Thr His Val Asn Leu Gly Val Lys Glu Glu His Tyr Pro Ile
                85                  90                  95

Val Gly Ala Cys Leu Leu Lys Ala Ile Lys Asn Leu Leu Asn Pro Asp
            100                 105                 110

Glu Ala Thr Leu Lys Ala Trp Glu Val Ala Tyr Gly Lys Ile Ala Lys
            115                 120                 125
```

```
Phe Tyr Ile Asp Ile Glu Lys Lys Leu Tyr Asp Lys
        130                 135                 140
```

<210> SEQ ID NO 10
<211> LENGTH: 146
<212> TYPE: PRT
<213> ORGANISM: Vitreoscilla stercoraria

<400> SEQUENCE: 10

```
Met Leu Asp Gln Gln Thr Ile Asn Ile Ile Lys Ala Thr Val Pro Val
1               5                   10                  15

Leu Lys Glu His Gly Val Thr Ile Thr Thr Phe Tyr Lys Asn Leu
                20                  25                  30

Phe Ala Lys His Pro Glu Val Arg Pro Leu Phe Asp Met Gly Arg Gln
                35                  40                  45

Glu Ser Leu Glu Gln Pro Lys Ala Leu Ala Met Thr Val Leu Ala Ala
        50                  55                  60

Ala Gln Asn Ile Glu Asn Leu Pro Ala Ile Leu Pro Ala Val Lys Lys
65                  70                  75                  80

Ile Ala Val Lys His Cys Gln Ala Gly Val Ala Ala His Tyr Pro
                85                  90                  95

Ile Val Gly Gln Glu Leu Leu Gly Ala Ile Lys Glu Val Leu Gly Asp
                100                 105                 110

Ala Ala Thr Asp Asp Ile Leu Asp Ala Trp Gly Lys Ala Tyr Gly Val
                115                 120                 125

Ile Ala Asp Val Phe Ile Gln Val Glu Ala Asp Leu Tyr Ala Gln Ala
        130                 135                 140

Val Glu
145
```

<210> SEQ ID NO 11
<211> LENGTH: 150
<212> TYPE: PRT
<213> ORGANISM: Mus musculus

<400> SEQUENCE: 11

```
Met Glu Arg Pro Glu Ser Glu Leu Ile Arg Gln Ser Trp Arg Val Val
1               5                   10                  15

Ser Arg Ser Pro Leu Glu His Gly Thr Val Leu Phe Ala Arg Leu Phe
                20                  25                  30

Ala Leu Glu Pro Ser Leu Leu Pro Leu Phe Gln Tyr Asn Gly Arg Gln
                35                  40                  45

Phe Ser Ser Pro Glu Asp Cys Leu Ser Ser Pro Glu Phe Leu Asp His
        50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Thr Ser Leu Gly Arg Lys His
                85                  90                  95

Arg Ala Val Gly Val Arg Leu Ser Ser Phe Ser Thr Val Gly Glu Ser
                100                 105                 110

Leu Leu Tyr Met Leu Glu Lys Cys Leu Gly Pro Asp Phe Thr Pro Ala
                115                 120                 125

Thr Arg Thr Ala Trp Ser Arg Leu Tyr Gly Ala Val Val Gln Ala Met
        130                 135                 140

Ser Arg Gly Trp Asp Gly
145                 150
```

<210> SEQ ID NO 12
<211> LENGTH: 151
<212> TYPE: PRT
<213> ORGANISM: Homo sapiens

<400> SEQUENCE: 12

```
Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
            20                  25                  30

Ala Leu Glu Pro Asp Leu Leu Pro Leu Phe Gln Tyr Asn Cys Arg Gln
        35                  40                  45

Phe Ser Ser Pro Glu Asp Cys Leu Ser Ser Pro Glu Phe Leu Asp His
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150
```

<210> SEQ ID NO 13
<211> LENGTH: 150
<212> TYPE: PRT
<213> ORGANISM: Physeter catodon

<400> SEQUENCE: 13

```
Met Val Leu Ser Glu Gly Glu Trp Gln Leu Val Leu His Val Trp Ala
1               5                   10                  15

Lys Val Glu Ala Asp Val Ala Gly His Gly Gln Asp Ile Leu Ile Arg
            20                  25                  30

Leu Phe Lys Ser His Pro Glu Thr Leu Glu Lys Phe Asp Arg Phe Lys
        35                  40                  45

His Leu Lys Thr Glu Ala Glu Met Lys Ala Ser Glu Asp Leu Lys Lys
    50                  55                  60

His Gly Val Thr Val Leu Thr Ala Leu Gly Ala Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Glu Ala Ile
            100                 105                 110

Ile His Val Leu His Ser Arg His Pro Gly Asp Phe Gly Ala Asp Ala
        115                 120                 125

Gln Gly Ala Met Asn Lys Ala Leu Glu Leu Phe Arg Lys Asp Ile Ala
    130                 135                 140

Ala Lys Tyr Lys Glu Leu
145                 150
```

<210> SEQ ID NO 14
<211> LENGTH: 190

<212> TYPE: PRT
<213> ORGANISM: Homo sapiens

<400> SEQUENCE: 14

Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Cys Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

His Met Glu Asp Pro Leu Glu Met Glu Arg Ser Pro Gln Leu Arg Lys
65                  70                  75                  80

His Ala Cys Arg Val Met Gly Ala Leu Asn Thr Val Val Glu Asn Leu
                85                  90                  95

His Asp Pro Asp Lys Val Ser Ser Val Leu Ala Leu Val Gly Lys Ala
            100                 105                 110

His Ala Leu Lys His Lys Val Glu Pro Val Tyr Phe Lys Ile Leu Ser
        115                 120                 125

Gly Val Ile Leu Glu Val Val Ala Glu Glu Phe Ala Ser Asp Phe Pro
    130                 135                 140

Pro Glu Thr Gln Arg Ala Trp Ala Lys Leu Arg Gly Leu Ile Tyr Ser
145                 150                 155                 160

His Val Thr Ala Ala Tyr Lys Glu Val Gly Trp Val Gln Gln Val Pro
                165                 170                 175

Asn Ala Thr Thr Pro Pro Ala Thr Leu Pro Ser Ser Gly Pro
            180                 185                 190

<210> SEQ ID NO 15
<211> LENGTH: 338
<212> TYPE: PRT
<213> ORGANISM: Ascaris suum

<400> SEQUENCE: 15

Met Arg Ser Leu Leu Leu Ser Ile Val Phe Phe Val Val Thr Val
1               5                   10                  15

Ser Ala Asn Lys Thr Arg Glu Leu Cys Met Lys Ser Leu Glu His Ala
            20                  25                  30

Lys Val Asp Thr Ser Asn Glu Ala Arg Gln Asp Gly Ile Asp Leu Tyr
        35                  40                  45

Lys His Met Phe Glu Asn Tyr Pro Pro Leu Arg Lys Tyr Phe Lys Asn
    50                  55                  60

Arg Glu Glu Tyr Thr Ala Glu Asp Val Gln Asn Asp Pro Phe Phe Ala
65                  70                  75                  80

Lys Gln Gly Gln Lys Ile Leu Leu Ala Cys His Val Leu Cys Ala Thr
                85                  90                  95

Tyr Asp Asp Arg Glu Thr Phe Asn Ala Tyr Thr Arg Glu Leu Leu Asp
            100                 105                 110

Arg His Ala Arg Asp His Val His Met Pro Pro Glu Val Trp Thr Asp
        115                 120                 125

Phe Trp Lys Leu Phe Glu Glu Tyr Leu Gly Lys Lys Thr Thr Leu Asp
    130                 135                 140

Glu Pro Thr Lys Gln Ala Trp His Glu Ile Gly Arg Glu Phe Ala Lys
145                 150                 155                 160

Glu Ile Asn Lys His Gly Arg His Ala Val Arg His Gln Cys Met Arg
            165                 170                 175

Ser Leu Gln His Ile Asp Ile Gly His Ser Glu Thr Ala Lys Gln Asn
            180                 185                 190

Gly Ile Asp Leu Tyr Lys His Met Phe Glu Asn Tyr Pro Ser Met Arg
        195                 200                 205

Glu Ala Phe Lys Asp Arg Glu Asn Tyr Thr Ala Glu Asp Val Gln Lys
    210                 215                 220

Asp Pro Phe Phe Val Lys Gln Gly Gln Arg Ile Leu Leu Ala Cys His
225                 230                 235                 240

Leu Leu Cys Ala Ser Tyr Asp Asp Glu Glu Thr Phe His Met Tyr Val
                245                 250                 255

His Glu Leu Met Glu Arg His Glu Arg Leu Gly Val Gln Leu Pro Asp
            260                 265                 270

Gln His Trp Thr Asp Phe Trp Lys Leu Phe Glu Glu Phe Leu Glu Lys
        275                 280                 285

Lys Ser His Leu Cys Glu His Thr Lys His Ala Trp Ala Val Ile Gly
290                 295                 300

Lys Glu Phe Ala Tyr Glu Ala Thr Arg His Gly Lys Glu His His Glu
305                 310                 315                 320

His Lys Glu Glu His Lys Glu Glu His Lys Glu Glu His Lys Glu Glu
                325                 330                 335

Gln His

<210> SEQ ID NO 16
<211> LENGTH: 132
<212> TYPE: PRT
<213> ORGANISM: Bacillus subtilis

<400> SEQUENCE: 16

Met Gly Gln Ser Phe Asn Ala Pro Tyr Glu Ala Ile Gly Glu Glu Leu
1               5                   10                  15

Leu Ser Gln Leu Val Asp Thr Phe Tyr Glu Arg Val Ala Ser His Pro
            20                  25                  30

Leu Leu Lys Pro Ile Phe Pro Ser Asp Leu Thr Glu Thr Ala Arg Lys
        35                  40                  45

Gln Lys Gln Phe Leu Thr Gln Tyr Leu Gly Gly Pro Pro Leu Tyr Thr
    50                  55                  60

Glu Glu His Gly His Pro Met Leu Arg Ala Arg His Leu Pro Phe Pro
65                  70                  75                  80

Ile Thr Asn Glu Arg Ala Asp Ala Trp Leu Ser Cys Met Lys Asp Ala
                85                  90                  95

Met Asp His Val Gly Leu Glu Gly Glu Ile Arg Glu Phe Leu Phe Gly
            100                 105                 110

Arg Leu Glu Leu Thr Ala Arg His Met Val Asn Gln Thr Glu Ala Glu
        115                 120                 125

Asp Arg Ser Ser
    130

<210> SEQ ID NO 17
<211> LENGTH: 195
<212> TYPE: PRT
<213> ORGANISM: Methanosarcina acetivorans

<400> SEQUENCE: 17

Met Ser Val Glu Lys Ile Pro Gly Tyr Thr Tyr Gly Glu Thr Glu Asn

```
   1               5                  10                 15
Arg Ala Pro Phe Asn Leu Glu Asp Leu Lys Leu Leu Lys Glu Ala Val
                20                 25                 30

Met Phe Thr Ala Glu Asp Glu Tyr Ile Gln Lys Ala Gly Glu Val
                35                 40                 45

Leu Glu Asp Gln Val Glu Glu Ile Leu Asp Thr Trp Tyr Gly Phe Val
    50                 55                 60

Gly Ser His Pro His Leu Leu Tyr Tyr Phe Thr Ser Pro Asp Gly Thr
65                  70                 75                 80

Pro Asn Glu Lys Tyr Leu Ala Ala Val Arg Lys Arg Phe Ser Arg Trp
                85                 90                 95

Ile Leu Asp Thr Cys Asn Arg Ser Tyr Asp Gln Ala Trp Leu Asp Tyr
                100                105                110

Gln Tyr Glu Ile Gly Leu Arg His His Arg Thr Lys Lys Asn Gln Thr
                115                120                125

Asp Asn Val Glu Ser Val Pro Asn Ile Gly Tyr Arg Tyr Leu Val Ala
    130                135                140

Phe Ile Tyr Pro Ile Thr Ala Thr Met Lys Pro Phe Leu Ala Arg Lys
145                 150                155                160

Gly His Thr Pro Glu Glu Val Glu Lys Met Tyr Gln Ala Trp Phe Lys
                165                170                175

Ala Thr Thr Leu Gln Val Ala Leu Trp Ser Tyr Pro Tyr Val Lys Tyr
                180                185                190

Gly Asp Phe
        195

<210> SEQ ID NO 18
<211> LENGTH: 195
<212> TYPE: PRT
<213> ORGANISM: Aeropyrum pernix

<400> SEQUENCE: 18

Met Thr Pro Ser Asp Ile Pro Gly Tyr Asp Tyr Gly Arg Val Glu Lys
1               5                  10                 15

Ser Pro Ile Thr Asp Leu Glu Phe Asp Leu Leu Lys Lys Thr Val Met
                20                 25                 30

Leu Gly Glu Lys Asp Val Met Tyr Leu Lys Lys Ala Cys Asp Val Leu
                35                 40                 45

Lys Asp Gln Val Asp Glu Ile Leu Asp Leu Trp Tyr Gly Trp Val Ala
    50                 55                 60

Ser Asn Glu His Leu Ile Tyr Tyr Phe Ser Asn Pro Asp Thr Gly Glu
65                  70                 75                 80

Pro Ile Lys Glu Tyr Leu Glu Arg Val Arg Ala Arg Phe Gly Ala Trp
                85                 90                 95

Ile Leu Asp Thr Thr Cys Arg Asp Tyr Asn Arg Glu Trp Leu Asp Tyr
                100                105                110

Gln Tyr Glu Val Gly Leu Arg His His Arg Ser Lys Lys Gly Val Thr
                115                120                125

Asp Gly Val Arg Thr Val Pro His Ile Pro Leu Arg Tyr Leu Ile Ala
    130                135                140

Phe Ile Tyr Pro Ile Thr Ala Thr Ile Lys Pro Phe Leu Ala Lys Lys
145                 150                155                160

Gly Gly Ser Pro Glu Asp Ile Glu Gly Met Tyr Asn Ala Trp Phe Lys
                165                170                175
```

Ser Val Val Leu Gln Val Ala Ile Trp Ser His Pro Tyr Thr Lys Glu
            180                 185                 190

Asn Asp Trp
        195

<210> SEQ ID NO 19
<211> LENGTH: 192
<212> TYPE: PRT
<213> ORGANISM: Pyrobaculum ferrireducens

<400> SEQUENCE: 19

Met Arg Glu Ile Pro Gly Tyr Glu Phe Gly Lys Val Pro Asp Ala Pro
1               5                   10                  15

Ile Ser Asp Glu Glu Phe Glu Leu Leu Lys Lys Ser Val Met Trp Thr
            20                  25                  30

Glu Glu Asp Glu Lys Tyr Arg Lys Leu Ala Cys Glu Val Leu Lys Gly
        35                  40                  45

Gln Val Glu Gln Ile Leu Asp Leu Trp Tyr Gly Trp Val Gly Ser Asn
    50                  55                  60

Pro His Leu Val Tyr Tyr Phe Gly Asp Arg Ser Gly Arg Pro Ile Pro
65                  70                  75                  80

Gln Tyr Leu Glu Ala Val Arg Lys Arg Phe Gly Gln Trp Ile Leu Asp
                85                  90                  95

Thr Val Cys Arg Ser Tyr Asp Arg Gln Trp Leu Asn Tyr Val Tyr Glu
            100                 105                 110

Ile Gly Leu Arg His His Arg Thr Lys Lys Gly Lys Thr Asp Gly Val
        115                 120                 125

Glu Thr Val Glu His Ile Pro Leu Arg Tyr Met Val Ala Phe Ile Ala
    130                 135                 140

Pro Ile Gly Leu Thr Ile Lys Pro Phe Leu Glu Lys Gly Gly His Pro
145                 150                 155                 160

Pro Asp Val Val Glu Lys Met Trp Ala Ala Trp Ile Lys Ser Val Val
                165                 170                 175

Leu Gln Val Ala Ile Trp Ser His Pro Tyr Ala Lys Pro Gly Glu Trp
            180                 185                 190

<210> SEQ ID NO 20
<211> LENGTH: 400
<212> TYPE: PRT
<213> ORGANISM: Cupriavidus necator

<400> SEQUENCE: 20

Met Leu Thr Gln Lys Thr Lys Asp Ile Val Lys Ala Thr Ala Pro Val
1               5                   10                  15

Leu Ala Glu His Gly Tyr Asp Ile Ile Lys Cys Phe Tyr Gln Arg Met
            20                  25                  30

Phe Glu Ala His Pro Glu Leu Lys Asn Val Phe Asn Met Ala His Gln
        35                  40                  45

Glu Gln Gly Gln Gln Gln Ala Leu Ala Arg Ala Val Tyr Ala Tyr
    50                  55                  60

Ala Glu Asn Ile Glu Asp Pro Asn Ser Leu Met Ala Val Leu Lys Asn
65                  70                  75                  80

Ile Ala Asn Lys His Ala Ser Leu Gly Val Lys Pro Glu Gln Tyr Pro
                85                  90                  95

Ile Val Gly Glu His Leu Leu Ala Ala Ile Lys Glu Val Leu Gly Asn
            100                 105                 110

-continued

```
Ala Ala Thr Asp Asp Ile Ile Ser Ala Trp Ala Gln Ala Tyr Gly Asn
            115                 120                 125

Leu Ala Asp Val Leu Met Gly Met Glu Ser Glu Leu Tyr Glu Arg Ser
130                 135                 140

Ala Glu Gln Pro Gly Gly Trp Lys Gly Trp Arg Thr Phe Val Ile Arg
145                 150                 155                 160

Glu Lys Arg Pro Glu Ser Asp Val Ile Thr Ser Phe Ile Leu Glu Pro
                165                 170                 175

Ala Asp Gly Gly Pro Val Val Asn Phe Glu Pro Gly Gln Tyr Thr Ser
            180                 185                 190

Val Ala Ile Asp Val Pro Ala Leu Gly Leu Gln Gln Ile Arg Gln Tyr
        195                 200                 205

Ser Leu Ser Asp Met Pro Asn Gly Arg Ser Tyr Arg Ile Ser Val Lys
    210                 215                 220

Arg Glu Gly Gly Gly Pro Gln Pro Pro Gly Tyr Val Ser Asn Leu Leu
225                 230                 235                 240

His Asp His Val Asn Val Gly Asp Gln Val Lys Leu Ala Ala Pro Tyr
                245                 250                 255

Gly Ser Phe His Ile Asp Val Asp Ala Lys Thr Pro Ile Val Leu Ile
            260                 265                 270

Ser Gly Gly Val Gly Leu Thr Pro Met Val Ser Met Leu Lys Val Ala
        275                 280                 285

Leu Gln Ala Pro Pro Arg Gln Val Val Phe Val His Gly Ala Arg Asn
    290                 295                 300

Ser Ala Val His Ala Met Arg Asp Arg Leu Arg Glu Ala Ala Lys Thr
305                 310                 315                 320

Tyr Glu Asn Leu Asp Leu Phe Val Phe Tyr Asp Gln Pro Leu Pro Glu
                325                 330                 335

Asp Val Gln Gly Arg Asp Tyr Asp Tyr Pro Gly Leu Val Asp Val Lys
            340                 345                 350

Gln Ile Glu Lys Ser Ile Leu Leu Pro Asp Ala Asp Tyr Tyr Ile Cys
        355                 360                 365

Gly Pro Ile Pro Phe Met Arg Met Gln His Asp Ala Leu Lys Asn Leu
    370                 375                 380

Gly Ile His Glu Ala Arg Ile His Tyr Glu Val Phe Gly Pro Asp Leu
385                 390                 395                 400
```

<210> SEQ ID NO 21
<211> LENGTH: 145
<212> TYPE: PRT
<213> ORGANISM: Rhodothermus marinus

<400> SEQUENCE: 21

```
Met Ala Pro Thr Leu Ser Glu Gln Thr Arg Gln Leu Val Arg Ala Ser
1               5                   10                  15

Val Pro Ala Leu Gln Lys His Ser Val Ala Ile Ser Ala Thr Met Tyr
            20                  25                  30

Arg Leu Leu Phe Glu Arg Tyr Pro Glu Thr Arg Ser Leu Phe Glu Leu
        35                  40                  45

Pro Glu Arg Gln Ile His Lys Leu Ala Ser Ala Leu Leu Ala Tyr Ala
    50                  55                  60

Arg Ser Ile Asp Asn Pro Ser Ala Leu Gln Ala Ala Ile Arg Arg Met
65                  70                  75                  80

Val Leu Ser His Ala Arg Ala Gly Val Gln Ala Val His Tyr Pro Leu
                85                  90                  95
```

```
Val Trp Glu Cys Leu Arg Asp Ala Ile Lys Glu Val Leu Gly Pro Asp
                100                 105                 110

Ala Thr Glu Thr Leu Leu Gln Ala Trp Lys Glu Ala Tyr Asp Phe Leu
            115                 120                 125

Ala His Leu Leu Ser Thr Lys Glu Ala Gln Val Tyr Ala Val Leu Ala
        130                 135                 140

Glu
145

<210> SEQ ID NO 22
<211> LENGTH: 293
<212> TYPE: PRT
<213> ORGANISM: Saccharomyces cerevisiae

<400> SEQUENCE: 22

Thr Pro Leu Val His Val Ala Ser Val Glu Lys Gly Arg Ser Tyr Glu
1               5                   10                  15

Asp Phe Gln Lys Val Tyr Asn Ala Ile Ala Leu Lys Leu Arg Glu Asp
                20                  25                  30

Asp Glu Tyr Asp Asn Tyr Ile Gly Tyr Gly Pro Val Leu Val Arg Leu
            35                  40                  45

Ala Trp His Thr Ser Gly Thr Trp Asp Lys His Asp Asn Thr Gly Gly
        50                  55                  60

Ser Tyr Gly Gly Thr Tyr Arg Phe Lys Lys Glu Phe Asn Asp Pro Ser
65                  70                  75                  80

Asn Ala Gly Leu Gln Asn Gly Phe Lys Phe Leu Glu Pro Ile His Lys
                85                  90                  95

Glu Phe Pro Trp Ile Ser Ser Gly Asp Leu Phe Ser Leu Gly Gly Val
                100                 105                 110

Thr Ala Val Gln Glu Met Gln Gly Pro Lys Ile Pro Trp Arg Cys Gly
            115                 120                 125

Arg Val Asp Thr Pro Glu Asp Thr Thr Pro Asp Asn Gly Arg Leu Pro
        130                 135                 140

Asp Ala Asp Lys Asp Ala Asp Tyr Val Arg Thr Phe Phe Gln Arg Leu
145                 150                 155                 160

Asn Met Asn Asp Arg Glu Val Val Ala Leu Met Gly Ala His Ala Leu
                165                 170                 175

Gly Lys Thr His Leu Lys Asn Ser Gly Tyr Glu Gly Pro Trp Gly Ala
            180                 185                 190

Ala Asn Asn Val Phe Thr Asn Glu Phe Tyr Leu Asn Leu Leu Asn Glu
        195                 200                 205

Asp Trp Lys Leu Glu Lys Asn Asp Ala Asn Asn Glu Gln Trp Asp Ser
    210                 215                 220

Lys Ser Gly Tyr Met Met Leu Pro Thr Asp Tyr Ser Leu Ile Gln Asp
225                 230                 235                 240

Pro Lys Tyr Leu Ser Ile Val Lys Glu Tyr Ala Asn Asp Gln Asp Lys
                245                 250                 255

Phe Phe Lys Asp Phe Ser Lys Ala Phe Glu Lys Leu Leu Glu Asn Gly
            260                 265                 270

Ile Thr Phe Pro Lys Asp Ala Pro Ser Pro Phe Ile Phe Lys Thr Leu
        275                 280                 285

Glu Glu Gln Gly Leu
    290
```

<210> SEQ ID NO 23
<211> LENGTH: 306
<212> TYPE: PRT
<213> ORGANISM: Armoracia rusticana

<400> SEQUENCE: 23

Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
            20                  25                  30

Ala Ala Ser Ile Leu Arg Leu His Phe His Asp Cys Phe Val Asn Gly
        35                  40                  45

Cys Asp Ala Ser Ile Leu Leu Asp Asn Thr Thr Ser Phe Arg Thr Glu
    50                  55                  60

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
                85                  90                  95

Cys Ala Asp Leu Leu Thr Ile Ala Ala Gln Gln Ser Val Thr Leu Ala
            100                 105                 110

Gly Gly Pro Ser Trp Arg Val Pro Leu Gly Arg Arg Asp Ser Leu Gln
        115                 120                 125

Ala Phe Leu Asp Leu Ala Asn Ala Asn Leu Pro Ala Pro Phe Phe Thr
    130                 135                 140

Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
                165                 170                 175

Cys Arg Phe Ile Met Asp Arg Leu Tyr Asn Phe Ser Asn Thr Gly Leu
            180                 185                 190

Pro Asp Pro Thr Leu Asn Thr Thr Tyr Leu Gln Thr Leu Arg Gly Leu
        195                 200                 205

Cys Pro Leu Asn Gly Asn Leu Ser Ala Leu Val Asp Phe Asp Leu Arg
    210                 215                 220

Thr Pro Thr Ile Phe Asp Asn Lys Tyr Tyr Val Asn Leu Glu Glu Gln
225                 230                 235                 240

Lys Gly Leu Ile Gln Ser Asp Gln Glu Leu Phe Ser Ser Pro Asn Ala
                245                 250                 255

Thr Asp Thr Ile Pro Leu Val Arg Ser Phe Ala Asn Ser Thr Gln Thr
            260                 265                 270

Phe Phe Asn Ala Phe Val Glu Ala Met Asp Arg Met Gly Asn Ile Thr
        275                 280                 285

Pro Leu Thr Gly Thr Gln Gly Gln Ile Arg Leu Asn Cys Arg Val Val
    290                 295                 300

Asn Ser
305

<210> SEQ ID NO 24
<211> LENGTH: 527
<212> TYPE: PRT
<213> ORGANISM: Homo sapiens

<400> SEQUENCE: 24

Met Ala Asp Ser Arg Asp Pro Ala Ser Asp Gln Met Gln His Trp Lys
1               5                   10                  15

Glu Gln Arg Ala Ala Gln Lys Ala Asp Val Leu Thr Thr Gly Ala Gly

```
                20                  25                  30
Asn Pro Val Gly Asp Lys Leu Asn Val Ile Thr Val Gly Pro Arg Gly
     35                  40                  45
Pro Leu Leu Val Gln Asp Val Phe Thr Asp Glu Met Ala His Phe
 50                  55                  60
Asp Arg Glu Arg Ile Pro Glu Arg Val Val His Ala Lys Gly Ala Gly
 65                  70                  75                  80
Ala Phe Gly Tyr Phe Glu Val Thr His Asp Ile Thr Lys Tyr Ser Lys
                 85                  90                  95
Ala Lys Val Phe Glu His Ile Gly Lys Lys Thr Pro Ile Ala Val Arg
             100                 105                 110
Phe Ser Thr Val Ala Gly Glu Ser Gly Ser Ala Asp Thr Val Arg Asp
             115                 120                 125
Pro Arg Gly Phe Ala Val Lys Phe Tyr Thr Glu Asp Gly Asn Trp Asp
             130                 135                 140
Leu Val Gly Asn Asn Thr Pro Ile Phe Phe Ile Arg Asp Pro Ile Leu
145                 150                 155                 160
Phe Pro Ser Phe Ile His Ser Gln Lys Arg Asn Pro Gln Thr His Leu
                 165                 170                 175
Lys Asp Pro Asp Met Val Trp Asp Phe Trp Ser Leu Arg Pro Glu Ser
             180                 185                 190
Leu His Gln Val Ser Phe Leu Phe Ser Asp Arg Gly Ile Pro Asp Gly
             195                 200                 205
His Arg His Met Asn Gly Tyr Gly Ser His Thr Phe Lys Leu Val Asn
             210                 215                 220
Ala Asn Gly Glu Ala Val Tyr Cys Lys Phe His Tyr Lys Thr Asp Gln
225                 230                 235                 240
Gly Ile Lys Asn Leu Ser Val Glu Asp Ala Ala Arg Leu Ser Gln Glu
                 245                 250                 255
Asp Pro Asp Tyr Gly Ile Arg Asp Leu Phe Asn Ala Ile Ala Thr Gly
             260                 265                 270
Lys Tyr Pro Ser Trp Thr Phe Tyr Ile Gln Val Met Thr Phe Asn Gln
             275                 280                 285
Ala Glu Thr Phe Pro Phe Asn Pro Phe Asp Leu Thr Lys Val Trp Pro
             290                 295                 300
His Lys Asp Tyr Pro Leu Ile Pro Val Gly Lys Leu Val Leu Asn Arg
305                 310                 315                 320
Asn Pro Val Asn Tyr Phe Ala Glu Val Glu Gln Ile Ala Phe Asp Pro
                 325                 330                 335
Ser Asn Met Pro Pro Gly Ile Glu Ala Ser Pro Asp Lys Met Leu Gln
             340                 345                 350
Gly Arg Leu Phe Ala Tyr Pro Asp Thr His Arg His Arg Leu Gly Pro
             355                 360                 365
Asn Tyr Leu His Ile Pro Val Asn Cys Pro Tyr Arg Ala Arg Val Ala
             370                 375                 380
Asn Tyr Gln Arg Asp Gly Pro Met Cys Met Gln Asp Asn Gln Gly Gly
385                 390                 395                 400
Ala Pro Asn Tyr Tyr Pro Asn Ser Phe Gly Ala Pro Glu Gln Gln Pro
                 405                 410                 415
Ser Ala Leu Glu His Ser Ile Gln Tyr Ser Gly Glu Val Arg Arg Phe
             420                 425                 430
Asn Thr Ala Asn Asp Asp Asn Val Thr Gln Val Arg Ala Phe Tyr Val
             435                 440                 445
```

```
Asn Val Leu Asn Glu Glu Gln Arg Lys Arg Leu Cys Glu Asn Ile Ala
    450                 455                 460

Gly His Leu Lys Asp Ala Gln Ile Phe Ile Gln Lys Lys Ala Val Lys
465                 470                 475                 480

Asn Phe Thr Glu Val His Pro Asp Tyr Gly Ser His Ile Gln Ala Leu
                485                 490                 495

Leu Asp Lys Tyr Asn Ala Glu Lys Pro Lys Asn Ala Ile His Thr Phe
                500                 505                 510

Val Gln Ser Gly Ser His Leu Ala Ala Arg Glu Lys Ala Asn Leu
                515                 520                 525

<210> SEQ ID NO 25
<211> LENGTH: 753
<212> TYPE: PRT
<213> ORGANISM: Escherichia coli

<400> SEQUENCE: 25

Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
                20                  25                  30

Asp Gly Ser His Arg Pro Ala Ala Glu Pro Thr Pro Pro Gly Ala Gln
            35                  40                  45

Pro Thr Ala Pro Gly Ser Leu Lys Ala Pro Asp Thr Arg Asn Glu Lys
50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
                100                 105                 110

Lys Ile Thr His Phe Asp His Glu Arg Ile Pro Glu Arg Ile Val His
            115                 120                 125

Ala Arg Gly Ser Ala Ala His Gly Tyr Phe Gln Pro Tyr Lys Ser Leu
130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
                195                 200                 205

Gln Asp Ala His Lys Phe Pro Asp Phe Val His Ala Val Lys Pro Glu
            210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
                275                 280                 285

Val Arg Phe His Trp Lys Pro Leu Ala Gly Lys Ala Ser Leu Val Trp
```

-continued

```
            290                 295                 300
Asp Glu Ala Gln Lys Leu Thr Gly Arg Asp Pro Asp Phe His Arg Arg
305                 310                 315                 320
Glu Leu Trp Glu Ala Ile Glu Ala Gly Asp Phe Pro Glu Tyr Glu Leu
                    325                 330                 335
Gly Phe Gln Leu Ile Pro Glu Glu Glu Phe Lys Phe Asp Phe Asp
                340                 345                 350
Leu Leu Asp Pro Thr Lys Leu Ile Pro Glu Glu Leu Val Pro Val Gln
                355                 360                 365
Arg Val Gly Lys Met Val Leu Asn Arg Asn Pro Asp Asn Phe Phe Ala
            370                 375                 380
Glu Asn Glu Gln Ala Ala Phe His Pro Gly His Ile Val Pro Gly Leu
385                 390                 395                 400
Asp Phe Thr Asn Asp Pro Leu Leu Gln Gly Arg Leu Phe Ser Tyr Thr
                405                 410                 415
Asp Thr Gln Ile Ser Arg Leu Gly Gly Pro Asn Phe His Glu Ile Pro
                420                 425                 430
Ile Asn Arg Pro Thr Cys Pro Tyr His Asn Phe Gln Arg Asp Gly Met
            435                 440                 445
His Arg Met Gly Ile Asp Thr Asn Pro Ala Asn Tyr Glu Pro Asn Ser
            450                 455                 460
Ile Asn Asp Asn Trp Pro Arg Glu Thr Pro Pro Gly Pro Lys Arg Gly
465                 470                 475                 480
Gly Phe Glu Ser Tyr Gln Glu Arg Val Glu Gly Asn Lys Val Arg Glu
                485                 490                 495
Arg Ser Pro Ser Phe Gly Glu Tyr Tyr Ser His Pro Arg Leu Phe Trp
                500                 505                 510
Leu Ser Gln Thr Pro Phe Glu Gln Arg His Ile Val Asp Gly Phe Ser
                515                 520                 525
Phe Glu Leu Ser Lys Val Val Arg Pro Tyr Ile Arg Glu Arg Val Val
                530                 535                 540
Asp Gln Leu Ala His Ile Asp Leu Thr Leu Ala Gln Ala Val Ala Lys
545                 550                 555                 560
Asn Leu Gly Ile Glu Leu Thr Asp Asp Gln Leu Asn Ile Thr Pro Pro
                565                 570                 575
Pro Asp Val Asn Gly Leu Lys Lys Asp Pro Ser Leu Ser Leu Tyr Ala
                580                 585                 590
Ile Pro Asp Gly Asp Val Lys Gly Arg Val Val Ala Ile Leu Leu Asn
            595                 600                 605
Asp Glu Val Arg Ser Ala Asp Leu Leu Ala Ile Leu Lys Ala Leu Lys
            610                 615                 620
Ala Lys Gly Val His Ala Lys Leu Leu Tyr Ser Arg Met Gly Glu Val
625                 630                 635                 640
Thr Ala Asp Asp Gly Thr Val Leu Pro Ile Ala Ala Thr Phe Ala Gly
                645                 650                 655
Ala Pro Ser Leu Thr Val Asp Ala Val Ile Val Pro Cys Gly Asn Ile
                660                 665                 670
Ala Asp Ile Ala Asp Asn Gly Asp Ala Asn Tyr Tyr Leu Met Glu Ala
            675                 680                 685
Tyr Lys His Leu Lys Pro Ile Ala Leu Ala Gly Asp Ala Arg Lys Phe
            690                 695                 700
Lys Ala Thr Ile Lys Ile Ala Asp Gln Gly Glu Glu Gly Ile Val Glu
705                 710                 715                 720
```

```
Ala Asp Ser Ala Asp Gly Ser Phe Met Asp Glu Leu Leu Thr Leu Met
            725                 730                 735
Ala Ala His Arg Val Trp Ser Arg Ile Pro Lys Ile Asp Lys Ile Pro
            740                 745                 750
Ala
```

HEME PROTEIN CATALYSTS FOR CARBON-BORON BOND FORMATION IN VITRO AND IN VIVO

CROSS-REFERENCES TO RELATED APPLICATIONS

The present application claims priority to U.S. Provisional Pat. Appl. No. 62/467,909, filed Mar. 7, 2017, and U.S. Provisional Pat. Appl. No. 62/535,411, filed Jul. 21, 2017, which applications are incorporated herein by reference in their entirety.

STATEMENT AS TO RIGHTS TO INVENTIONS MADE UNDER FEDERALLY SPONSORED RESEARCH AND DEVELOPMENT

This inventions was made with government support under Grant No. CBET1403077 awarded by the National Science Foundation and Grant No. F32GM125231 awarded by the National Institutes of Health. The government has certain rights in the invention.

REFERENCE TO SUBMISSION OF A SEQUENCE LISTING AS A TEXT FILE

The Sequence Listing written in file SEQ_086544-1074263-020820US_ST25.txt created on Mar. 9, 2018, 52,899 bytes, machine format IBM-PC, MS-Windows operating system, is hereby incorporated by reference in its entirety for all purposes.

BACKGROUND OF THE INVENTION

Organoboron compounds are useful for a variety of biomedical applications (see, e.g., Das, et al. *Future Med. Chem.* 2013, 5, 653.). For instance, $^{10}$B-containing molecules are widely used in boron neutron capture therapy (BNCT), a radiation therapy for the treatment of malignant tumors (see, e.g., Barth, et al. *Clin. Cancer Res.* 2005, 11, 3987). In addition, there is interest of organoboron compounds to treat diseases, as exemplified by bortezomib (Velcade), the first FDA-approved boron-based drug for the treatment of multiple myeloma and mantle cell lymphoma (see, e.g., Gorovoy, et al. *Chem. Biol. Drug Des.* 2013, 81, 408; Richardson, et al. *Annu. Rev. Med.* 2006; Vol. 57, p 33; Smoum, et al. *Chem. Rev.* 2012, 112, 4156.). The prevalence of organoborons necessitates the development of new methods for preparing molecules with high efficiency and selectivity. Carbenoid insertion into a B-H bond represents a very appealing strategy for introducing boron atoms into organic molecules that offers several distinct advantages over other borylation methods. It utilizes tetravalent boranes as borane reagents, which are much more stable, less toxic, and easier to handle than the Lewis-acidic trivalent borane reagents used in most borylation reactions (see, e.g., Curran, et al. *Angew. Chem. Int. Ed.* 2011, 50, 10294). Furthermore, carbenoid B-H insertion is highly desirable for the synthesis of α-borylcarbonyl molecules, which can be easily derivatized to a wide range of functionalized organoborons such as β-boryl alcohols, enamines, and enol ethers (see, e.g., He, et al. *Acc. Chem. Res.* 2014, 47, 1029; He, et al. *Dalton Trans.* 2014, 43, 11434; He, et al. *J. Am. Chem. Soc.* 2011, 133, 13770; He, et al. *J. Am. Chem. Soc.* 2012, 134, 9926.). Examples of metal-catalyzed carbene insertions into B-H bonds were reported only very recently with rhodium and copper-based catalysts (see, e.g., Li, et al. *J. Am. Chem. Soc.* 2013, 135, 12076; Cheng, et al. *J. Am. Chem. Soc.* 2013, 135, 14094; Chen, et al. *J. Am. Chem. Soc.* 2015, 137, 5268.). These reactions allow the preparation of α-borylcarbonyl compounds, but not without limitations. In addition to low catalyst turnovers (<100) and hazardous halogenated solvents, these reactions are narrow in scope: only α-aryl-α-diazocarbonyl compounds are accommodated in the enantioselective B-H insertion reactions reported in the literature.

Enzymes are remarkable for catalyzing chemical transformations with high chemo-, regio-, and enantio-selectivity under environmentally benign conditions (see, e.g., Bornscheuer, et al. *Nature* 2012, 485, 185; Bloom, Arnold. *Proc. Natl. Acad. Sci. U.S.A.* 2009, 106, 9995; Reetz, *J. Am. Chem. Soc.* 2013, 135, 12480.). Therefore, biocatalysis has become increasingly important for the pharmaceutical industry, with applications ranging from drug discovery to industrial-scale pharmaceutical production (see, e.g., Tucker, et al. *Nature* 2016, 534, 27; Tao, et al. *Biocatalysis for the Pharmaceutical Industry: Discovery, Development, and Manufacturing*; Wiley, 2009.). Despite the myriad of currently available biocatalysts, however, enzymes that catalyze the formation of carbon-boron (C—B) bonds are unknown. During the past four years, the Arnold laboratory has developed a biocatalytic platform that uses cytochrome P450s, nature's most versatile oxidation catalysts, for a broad range of non-natural transformations including alkene cyclopropanation, aziridination, aliphatic C—H amination, sulfimidation, and carbenoid insertion into N—H bonds (see, e.g., Hernandez, Arnold, et al. *ACS Catalysis* 2016, 6, 7810; Renata, Arnold, et al. *Angew. Chem. Int. Ed.* 2015, 54, 3351; Wang, Arnold, et al. *Chem. Sci.* 2014, 5, 598; Hyster, Arnold. *Isr. J. Chem.* 2015, 55, 14; Coelho, Arnold, et al. *Nat. Chem. Biol.* 2013, 9, 485; Arnold. *Q. Rev. Biophys.* 2015, 48, 404; Coelho, Arnold, et al. *Science* 2013, 339, 307; Kan, Arnold, et al. *Science* 2016, 354, 1048.). They and others have also demonstrated that other heme-containing proteins can catalyze carbenoid insertion and other reactions (see also, e.g., Bordeaux, et al. *Bioorg. Med. Chem.* 2014, 22, 5697; Bordeaux et al. *Angew. Chem. Int. Ed.* 2015, 54, 1744; Sreenilayam, et al. *Chem. Commun.* 2015, 51, 1532; Tyagi, et al. *Chem Sci.* 2015, 6, 2488; Bajaj, et al. *Angew. Chem. Int. Ed.* 2016, 55, 16110; Tyagi, et al. *Angew. Chem. Int. Ed.* 2016, 55, 2512; Giavani, et al. *Chem Sci.* 2016, 7, 234; Gober, et al. *ChemBioChem* 2016, 17, 394.). However, C—B bond formation using an enzyme has never been demonstrated. Harnessing the highly evolvable nature of hemoproteins toward metal-carbenoid chemistries, herein we developed the first biocatalytic C—B bond forming transformation. We have used directed evolution of hemoproteins to create enzymes that effect iron-carbenoid insertion into boron-hydrogen bonds for the first time.

Recent advances in enzyme engineering and design have expanded nature's catalytic repertoire to functions that are new to biology[1-3]. Yet only a subset of these engineered enzymes can function in living systems[4-7]. Finding enzymatic pathways that forge chemical bonds not found in biology is particularly difficult in the cellular environment, as this hinges on the discovery not only of new enzyme activities but also reagents that are simultaneously sufficiently reactive for the desired transformation and stable in vivo. Here we report the discovery, evolution, and generalisation of a fully genetically-encoded platform for producing chiral organoboranes in bacteria. *Escherichia coli* harbouring wild-type cytochrome c from *Rhodothermus marinus*[8] (Rma cyt c) were found to form carbon-boron bonds in the presence of borane-Lewis base complexes, through carbene insertion into B—H bonds. Directed evolution of Rma cyt c in the bacterial catalyst provided access to 16 novel chiral organoboranes. The catalyst is suitable for gram scale biosynthesis, offering up to 15300 turnovers, 6100 h$^{-1}$ turnover frequency, 99:1 enantiomeric ratio (e.r.), and 100% chemoselectivity. The enantio-preference of the biocatalyst could also be switched to provide either enantiomer of the organoborane products. Evolved in the context of whole-cell catalysts, the proteins were more active in the whole-cell system than in purified forms. This study establishes a DNA-encoded and readily engineered bacterial platform for borylation; engineering can be accomplished at a pace which rivals the development of chemical synthetic methods, with the ability to achieve turnovers that are two orders of magnitude (over 400-fold) greater than that of known chiral catalysts for the same class of transformation[9-11]. This tunable method for manipulating boron in cells opens a whole new world of boron chemistry in living systems.

Boron-containing natural products are synthesised in the soil by the myxobacterium *Sorangium cellulosum* as antibiotics against Gram-positive bacteria[12]. In the sea, these molecules give the Jurassic red alga *Solenopora jurassica* its distinct pink colouration[13]; they are also produced by the bioluminescent bacterium *Vibrio harveyi* for cell-cell communications[14] (FIG. 1). To prepare boron-containing biomolecules, living organisms produce small molecules that spontaneously react with boric acid available in the environment[15,16]. While this non-enzymatic method for capturing boron is sufficient for an organism's survival, it is limited to a substrate's inherent affinity towards boric acid, and lacks tunability and generality for synthetic biology applications. Moreover, organisms that produce organoboranes (compounds that contain carbon-boron bonds) are unknown.

BRIEF SUMMARY OF THE INVENTION

Provided herein are methods for producing an organoboron product. The methods include combining a boron-containing reagent and a carbene precursor in the presence of a heme protein or a variant thereof under conditions sufficient to form the organoboron product.

In some embodiments, the heme protein is a cytochrome c, a cytochrome P450, a globin, a protoglobin, a nitric oxide dioxygenase, a peroxidase, a catalase, or a variant thereof. In some embodiments, the heme protein is *Rhodothermus marinus* (Rma) mature cytochrome c or a variant thereof.

In some embodiments, the carbene precursor is a diazo compound such as an α-diazoester or a diazoalkylbenzene. In some embodiments, the boron-containing reagent contains a borane-Lewis base complex such as a borane N-heterocyclic carbene complex.

Also provided are reaction mixtures for producing organoboron products, as well as whole-cell catalysts comprising heme proteins and variants thereof for forming carbon-boron bonds.

DETAILED DESCRIPTION OF THE INVENTION

I. Introduction

Figure 1:
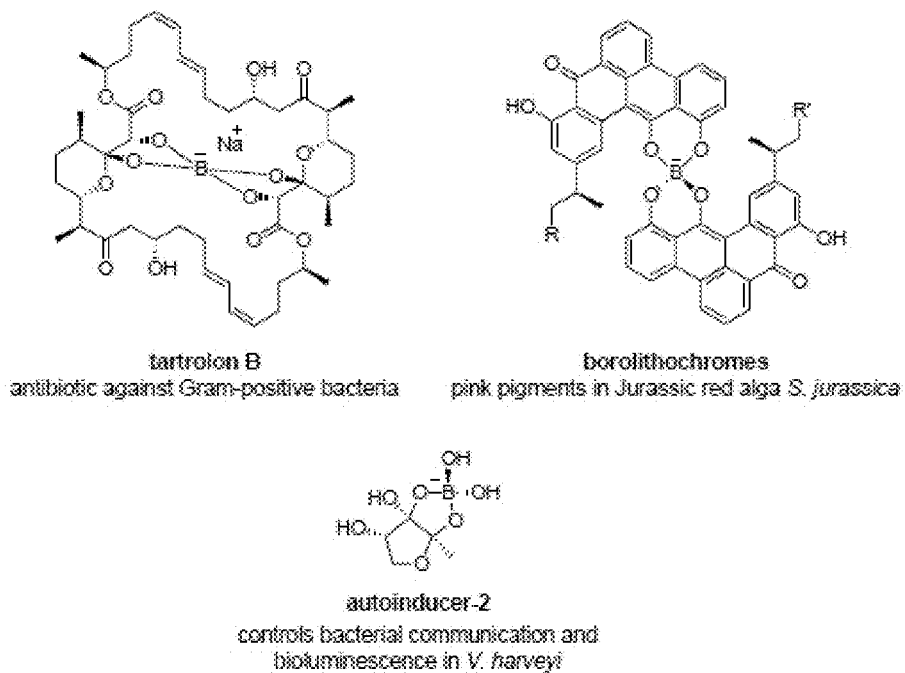
FIG. 1 shows examples of boron-containing natural products.

The present disclosure is directed to the in vitro and in vivo formation of carbon-boron bond between a boron-containing reagent and a diazo substrate catalyzed by various heme enzymes. The studies described herein represent the first example of biological C—B bond formation, and the first use of iron-based catalysts for carbene insertion into B—H bonds. In addition, the use of directed protein evolution for improving the enzyme's ability to construct C—B chemical bonds is demonstrated. Described herein are engineered heme proteins that catalyze carbon-boron bond formation with a total turnover number (TTN) up to 7000 and enantiomeric excess (ee) up to 98%, which can be improved by further engineering if desired. Processes for making compounds containing a C—B bond by treating a boron-containing reagent and a diazo substrate under appropriate conditions with a heme protein having C—B bond-forming activity are also described.

Enzyme-catalyzed borylation as described herein provides living organisms with the ability to produce boron-containing products. Such enzymes are not known in nature, but the present invention was developed based, in part, on the insight that existing natural proteins might be repurposed and engineered to perform this task. In the past, the present inventors and others have exploited the promiscuity of natural and engineered heme proteins for various non-natural reactions.[4,6,7,17] The resulting enzymes are fully genetically-encoded and carry out their synthetic functions in their bacterial expression hosts. Introducing boron motifs to organic molecules enantioselectively was one focus of the studies described herein, as this would generate boron-containing carbon-stereocenters, which are important structural features in functional organoboranes such as the FDA-approved chemotherapeutics Velcade® and Ninlaro®.[18] They are also versatile precursors for chemical derivatization through stereospecific carbon-boron to carbon-carbon/carbon-heteroatom bond conversion[19-21].

The platform for biological borylation disclosed herein can be tuned and configured through DNA manipulation. Microorganisms are powerful alternatives to chemical methods for producing pharmaceuticals, agrochemicals, materials, and fuels. They are available by fermentation at large scale and low cost, and their genetically-encoded synthetic prowess can be systematically modified and optimised. The methods disclosed herein provide a means for borylation chemistry to be added to biology's vast synthetic repertoire.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "heme protein variant" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The term "whole cell catalyst" includes cells expressing heme-containing enzymes, wherein the whole cell catalyst displays carbon-boron bond formation activity.

The term "carbene precursor" includes molecules that can be decomposed in the presence of metal (or enzyme) catalysts to form structures that contain at least one divalent carbon with two unshared valence shell electrons (i.e., carbenes) and that can be transferred to a boron-hydrogen bond, a boron-carbon bond, a boron-sulfur bond, a boron-nitrogen bond, a boron-boron bond, a boron-boron bond, or a boron-phosphorus bond to form various carbon ligated products. Examples of carbene precursors include, but are not limited to, diazo reagents, diazirene reagents, and epoxide reagents.

As used herein, the term "anaerobic", when used in reference to a reaction, culture or growth condition, is intended to mean that the concentration of oxygen is less than about 25 µM, preferably less than about 5 µM, and even more preferably less than 1 µM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. For example, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. For example, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. For example, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. For example, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. For example, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. For example, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be unsubstituted or substituted. For example, "substituted heteroaryl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. For example, "substituted alkoxy" groups can be substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. groups can be unsubstituted or substituted. For example, "substituted alkylthio" groups can be substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —$SiR_3$, wherein at least one R group is alkyl and the other R groups are H or alkyl. The alkyl groups can be substituted with one more halogen atoms.

As used herein, the term "acyl" refers to a moiety —C(O)R, wherein R is an alkyl group.

As used herein, the term "oxo" refers to an oxygen atom that is double-bonded to a compound (i.e., O═).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —$NR_3$, wherein each R group is H or alkyl.

As used herein, the term "amido" refers to a moiety —NRC(O)R or —C(O)$NR_2$, wherein each R group is H or alkyl.

As used herein, the term "phosphine" refers to a moiety —$PR_3$, wherein each R group is H, alkyl, cycloalkyl, aryl, or heterocyclyl.

As used herein, the term "organoboron compound" refers to a compound that contains a carbon-boron (C—B) bond. In general, C—B bonds have low polarity which contributes to the stability of many alkyl boron compounds. Boron often forms electron-deficient compounds, such as triorganoboranes. Organoboron compounds include, but are not limited to boranes, borohydrides, boronic acids, boronic esters, and borates.

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

III. Description of the Embodiments

The present invention provides compositions and enzymatic methods for the formation of carbon-boron (C—B) bonds from boron-containing reagents and reactive partners such as carbene precursors. The methods described herein provide organoboron products (e.g., compounds of Formula III and Formula IV as described below) as pure stereochemical isomers or as a mixture of stereochemically isomeric forms. In certain embodiments, heme protein variants comprising one or more amino acid mutations that catalyze carbene insertion into boron-hydrogen bonds are providing, allowing for the preparation of organoboron products with high stereoselectivity. In some embodiments, the heme protein variants have the ability to form carbon-boron bonds efficiently, display increased total turnover numbers, and/or demonstrate highly regio- and/or enantioselective product formation compared to the corresponding wild-type enzymes.

In some embodiments, the invention provides a method for producing an organoboron product in the presence of a boron-containing reagent, a diazo substrate, and a heme protein according to Equation 1 or Equation 2.

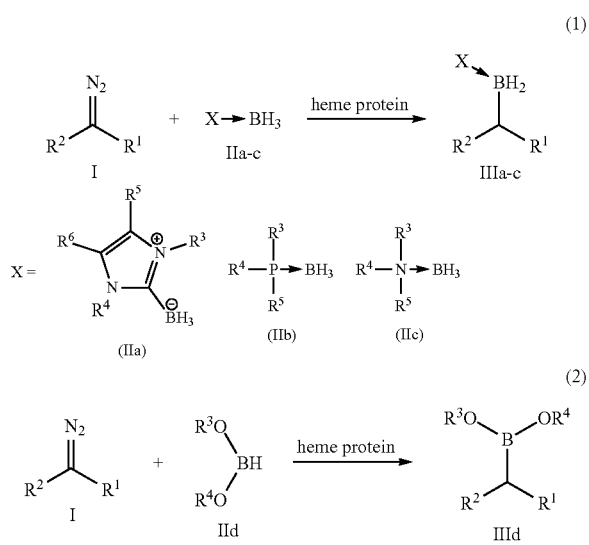

In Equations 1 and 2, $R^1$ and $R^2$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$.

$R^{1a}$ is selected from the group consisting of H, optionally substituted $C_{1-18}$ alkyl, $C_{1-18}$ alkoxy, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$.

$R^3$, $R^4$, $R^5$, and $R^6$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$.

each $R^7$, $R^8$, and $R^9$ is independently selected from the group consisting of H, optionally substituted $C_{1-18}$ alkyl, $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

A. Heme Proteins

The terms "heme protein" and "heme enzyme" are used herein to include any member of a group of proteins containing heme as a prosthetic group. Non-limiting examples of heme proteins include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome c1, cytochrome c, and combinations thereof. Heme-containing oxidoreductases include, but are not limited to, catalases, oxidases, oxygenases, haloperoxidases, peroxidases, and combinations thereof. In some instances, the globin protein is from *Methylacidiphilum infernorum*. In some other instances, the cytochrome P450 protein is a cytochrome P450 BM3 (CYP102A1) protein. Exemplary catalysts used in this method include, but are not limited to, heme proteins of the sort described in US 20140242647 A1.

In some embodiments, the heme protein is a member of one of the enzyme classes set forth in Table 1. In other embodiments, the heme protein is a variant or homolog of a member of one of the enzyme classes set forth in Table 1. In yet other embodiments, the heme protein comprises or consists of the heme domain of a member of one of the enzyme classes set forth in Table 1 or a fragment thereof (e.g., a truncated heme domain) that is capable of carrying out the carbene insertion reactions described herein.

TABLE 1

Heme enzymes identified by their enzyme classification number (EC number) and classification name

| EC Number | Name |
|---|---|
| 1.1.2.3 | L-lactate dehydrogenase |
| 1.1.2.6 | polyvinyl alcohol dehydrogenase (cytochrome) |
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH): |
| 1.3.5.1 | succinate dehydrogenase (ubiquinone) |
| 1.3.5.4 | fumarate reductase (menaquinone) |
| 1.3.99.1 | succinate dehydrogenase |

TABLE 1-continued

Heme enzymes identified by their enzyme classification number (EC number) and classification name

| EC Number | Name |
|---|---|
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide: cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | Catalase |
| 1.11.1.7 | Peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | Myeloperoxidase |
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen: quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |

TABLE 1-continued

Heme enzymes identified by their enzyme classification number (EC number) and classification name

| EC Number | Name |
|---|---|
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | Tyrosinase |
| 1.14.19.1 | stearoyl-CoA 9-desaturase |
| 1.14.19.3 | linoleoyl-CoA desaturase |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascorbate ferrireductase (transmembrane) |
| 1.16.9.1 | iron: rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | Cobaltochelatase |

In some embodiments, the heme protein is an engineered variant or a fragment thereof (e.g., a truncated variant containing the heme domain) comprising one or more mutation(s). In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val. In other embodiments, the heme protein variant is a chimeric protein comprising recombined sequences or blocks of amino acids from two, three, or more different heme-containing proteins. As described herein, heme protein catalysts described be improved through the introduction of mutations which alter the amino acid sequence of the heme protein so as to generate a catalyst that is highly productive and selective for the desired carbon-boron bond forming reaction. In particular, there are many examples in the scientific literature that describe processes through which the enantioselectivity and activity of carbene-transfer heme proteins can be optimized to form products that do not contain boron. Specifically, one skilled in the art will know that through a process of random mutagenesis via error-prone PCR, or through a process of site-saturation mutagenesis in which one or more codons are randomized sequentially or simultaneously, or through a process of gene synthesis in which random or directed mutations are introduced, many different mutants of the genes encoding the hemoprotein catalysts described herein can be generated. One skilled in the art will appreciate that heme protein variants can be expressed in a whole cell using an expression vector under the control of an inducible promoter or by means of chromosomal integration under the control of a constitutive promotor. The carbon-boron bond-forming activities of whole cell catalysts, cell lysates or purified proteins can be screened by GC or HPLC, using parameters including but not limited to turnovers and selectivities as selection criteria to find beneficial mutations.

In some embodiments, the heme enzyme comprises an oxidoreductase. Oxidoreductases are enzymes that catalyze the transfer of electrons from a reductant (i.e., an electron donor) to an oxidant (i.e., an electron acceptor) and are divided into 22 subclasses. Oxidoreductases typically utilize NADP or NAD+ as a cofactor. EC 1.1 oxidoreductases (alcohol oxidoreductases) act on the CH—OH group of donors. EC 1.2 oxidoreductases act on the aldehyde or oxo group of donors. EC 1.3 oxidoreductases (CH—CH oxidoreductases) act on the CH—CH group of donors. EC 1.4 oxidoreductases (amino acid oxidoreductases, monoamine oxidase) act on the CH—NH$_2$ group of donors. EC 1.5 oxidoreductases act on the CH—NH group of donors. EC 1.6 oxidoreductases act on NADH or NADPH. EC 1.7 oxidoreductases act on other nitrogenous compounds as donors. EC 1.8 oxidoreductases act on a sulfur group of donors. EC 1.9 oxidoreductases act on a heme group of donors. EC 1.10 oxidoreductases act on diphenols and related substances as donors. EC 1.12 oxidoreductases act on hydrogen as donors. EC 1.13 oxidoreductases (oxygenases) act on single donors with incorporation of molecular oxygen. EC 1.14 oxidoreductases act on paired donors with incorporation of molecular oxygen. EC 1.15 oxidoreductases act on superoxide radicals as acceptors. EC 1.16 oxidoreductases oxidize metal ions. EC 1.17 oxidoreductases act on CH or CH$_2$ groups. EC 1.18 oxidoreductases act on iron-sulfur proteins as donors. EC 1.19 oxidoreductases act on reduced flavodoxin as a donor. EC 1.20 oxidoreductases act on phosphorous or arsenic in donors. EC 1.21 oxidoreductases act on X—H and Y—H to form an X—Y bond. Enzyme classification number 1.97 includes other oxidoreductases that do not fit into any of the aforementioned subclasses. Haloperoxidases are peroxidases that mediate halide oxidation by hydrogen peroxide (EC 1.11.1).

In some embodiments, the heme enzyme comprises a cytochrome. Cytochromes are a class of heme proteins that are found in bacteria, as well as mitochondria and chloroplasts of eukaryotic organisms, and are typically associated with membranes. Cytochromes typically function in oxidative phosphorylation as components of electron transport chain systems. Cytochromes can be classified by spectroscopy, or by features such as the structure of the heme group, inhibitor sensitivity, or reduction potential. Three of the cytochromes, cytochromes a, b, and d, are classified by their prosthetic group (the prosthetic groups consisting of heme a, heme b, and tetrapyrrolic chelate of iron, respectively). Unlike the aforementioned cytochromes, cytochrome c is not defined in terms of its heme group. Cytochrome f, which performs similar functions to cytochrome $c_1$ but has a different structure, is sometimes regarded as a type of cytochrome c. Cytochrome P450 proteins form a distinct family of cytochromes.

In bacteria, mitochondria, and chloroplasts, various cytochromes form different combinations to that perform different functions. Cytochromes a and $a_3$ combine to form cytochrome c oxidase (also known as Complex IV), which is the last enzyme in the respiratory chain of bacteria and mitochondria. Cytochromes b and $c_1$ combine to form coenzyme Q-cytochrome c reductase—the third complex in the electron transport chain. Cytochromes $b_6$ and f combine to form plastoquinol-plastocyanin reductase, which is found in the chloroplasts of plants, cyanobacteria and green algae and functions in photosynthesis.

In some embodiments, the heme protein is a cytochrome c or a variant thereof. Cytochrome c proteins are a superfamily of proteins that have one or more covalently bonded heme prosthetic groups (i.e., heme c groups). Generally, the heme groups are bonded to the protein by one, or more typically two, thioether bonds involving sulfhydryl groups of cysteine residues. This superfamily of proteins possesses a characteristic CXXCH amino acid motif that binds heme, wherein X can be any amino acid. The fifth heme iron ligand is often provided by a histidine residue. Cytochrome c proteins possess a wide range of characteristics, enabling them to function in a large number of redox processes.

Cytochrome c is highly conserved across the spectrum of species. Non-limiting examples of cytochrome c amino acid sequences (encoded by the CYCS gene) can be found in NCBI Reference Sequence No. NM_018947.54→NP_061820.1 (human), NCBI Reference Sequence No. NM_007808.4→NP_031834.1 (mouse), and NCBI Reference No. ACA83734.1 (*Rhodothermus marinus* unprocessed).

Cytochrome c proteins fall into one of four classes. Class I contains soluble, low spin single domain C-type cytochromes. There are at least six subclasses of Class 1 cytochrome c proteins that are found in prokaryotes including *Desulfovibrio desulfuricans*, *Rhodospirillum rubrum*, *Rhodopila globiformis*, and *Rhodothermus marinus* (Rma). Class I proteins have a single heme that is attached near the N-terminus of the polypeptide, with a methionine residue being the sixth iron coordination site. Class II contains higher spin-state cytochrome c proteins, with the heme prosthetic group being attached closer to the C-terminus. Class III contains cytochromes with multiple heme groups. These proteins have lower redox potentials compared to the other three classes. Class IV contains more complex proteins having higher molecular weights. Class IV proteins contain heme c as well as other prosthetic groups.

In some embodiments, the cytochrome c protein is selected from the group consisting of *Rhodothermus marinus* (Rma) cytochrome c, *Rhodopila globiformis* cytochrome c, *Hydrogenobacter thermophilus* cytochrome c, *Saccharomyces cerevisiae* cytochrome c, horse heart cytochrome c, bovine heart cytochrome c, and combinations thereof.

In some embodiments, the cytochrome c protein variant comprises a mutation at one or more of the conserved residues of the corresponding wild-type sequence that serve as heme axial ligands. In a particular embodiment, the heme protein is a mature cytochrome c protein (residues 29-152 of the unprocessed peptide) B3FQS5_RHOMR (Swiss-prot: B3FQS5) from *Rhodothermus marinus* (*Rhodothermus*

*obamensis*), comprising the amino acid sequence set forth in SEQ ID NO:1, or a variant thereof.

In certain embodiments, the cytochrome c protein variant comprises one or more mutations at one or more conserved residues of the corresponding wild-type sequences that reside near (e.g., within about 10 Å, such as within 7 Å) the heme center. In some embodiments, for example, the B3FQS5_RHOMR protein (Rma cyt c) contains a mutation at the axial heme ligand residue M100 (mature peptide numbering convention) to any other amino acid residue that is among the naturally occurring twenty amino acids. The mutation can be, for example, an M100D mutation, an M100E mutation, an M100S mutation, an M100T, or an M100Y mutation. In some embodiments, the M100 mutation is an M100D mutation or an M100E mutation. In some embodiments, the M100 mutation is an M100D mutation. Without wishing to be bound by any particular theory, it is believed that a distal axial heme ligand mutation can enhance borylation activity by promoting formation of an iron carbenoid and subsequent formation of organoboron products.

Class I cytochrome c proteins often exhibit a conserved fold containing three α-helices arranged around the heme prosthetic group. In some embodiments, the heme protein is a cytochrome c having a mutation in a heme-adjacent helix. Amino acid residues in a heme-adjacent helix may reside within 10 angstroms of the heme prosthetic group (e.g., within 6 angstroms of the heme prosthetic group, or within 4 angstroms of the heme prosthetic group). In some instances the helix mutation can result in a structural change such as kink, bend, or other perturbation. Mutation of a helix residue to proline, for example, may cause the helix to bend or otherwise change. In certain instances, a helix mutation in Rma cyt c may reside in helix "C" (at any of residues 69-76) of the cytochrome c fold. The helix mutation can be a P69 mutation, a V70 mutation, a Y71 mutation, an I72 mutation, an M73 mutation, an N74 mutation, a V75 mutation, or an M76 mutation. In another non-limiting example, the helix mutation can reside in helix "A" (at any of residues 31-44) of the cytochrome c fold. The helix mutation can be an A31 mutation, an A32 mutation, an L33 mutation, an A34 mutation, a Q35 mutation, a Q36 mutation, a G37 mutation, an E38 mutation, a Q39 mutation, an L40 mutation, an F41 mutation, an N42 mutation, a T43 mutation, or a Y44 mutation. In another non-limiting example, the helix mutation can reside in helix "E" (at any of residues 107-122) of the cytochrome c fold. The helix mutation can be an E107 mutation, an E108 mutation, a Q109 mutation, an A110 mutation, an R111 mutation, an A112 mutation, an I113 mutation, an L114 mutation, an E115 mutation, a Y116 mutation, an L117 mutation, an R118 mutation, a Q119 mutation, a V120 mutation, an A121 mutation, or an E122 mutation. In another non-limiting example, the helix mutation can reside in helix "B'" of Rma cyt c (at any of residues 87-96). The helix mutation can be a P87 mutation, a V88 mutation, an M89 mutation, a K90 mutation, a Q91 mutation, an L92 mutation, a V93 mutation, a Q94 mutation, an E95 mutation, or a Y96 mutation.

Examples of helix mutations in Rma cyt c include, but are not limited to, an A31P mutation, an A32P mutation, an L33P mutation, an A34P mutation, a Q35P mutation, a Q36P mutation, a G37P mutation, an E38P mutation, a Q39P mutation, an L40P mutation, an F41P mutation, an N42P mutation, a T43P mutation, a Y44P mutation, a V70P mutation, a Y71P mutation, an I72P mutation, an M73P mutation, an N74P mutation, a V75P mutation, an M76P mutation, a V88P mutation, an M89P mutation, a K90P mutation, a Q91P mutation, an L92P mutation, a V93P mutation, a Q94P mutation, an E95P mutation, a Y96P mutation, an E107P mutation, an E108P mutation, a Q109P mutation, an A110P mutation, an R111P mutation, an A112P mutation, an I113P mutation, an L114P mutation, an E115P mutation, a Y116P mutation, an L117P mutation, an R118P mutation, a Q119P mutation, a V120P mutation, an A121P mutation, or an E122P mutation.

In some embodiments, the heme protein is an Rma cyt c variant having a mutation at V75 relative to the amino acid sequence set forth in SEQ ID NO:1. In some instances, the mutation is a V75R mutation, a V75P mutation, or a V75G mutation. As described in more detail below, Rma cyt c variants having a V75P mutation can be particularly useful for borylation of bulky diazoester substrates (including, but not limited to, ethyl 2-diazophenylacetate) while Rma cyt c variants having a V75G can be particularly useful for borylation of diazoalkyl benzene substrates (including, but not limited to, 1-diazo-2,2,2-trifluoroethyl)benzene). In some embodiments, the heme protein is an Rma cyt c variant having a mutation at Y71 relative to the amino acid sequence set forth in SEQ ID NO:1. In some instances, the mutation is Y71C.

In some embodiments, the heme protein is an Rma cyt c variant having a mutation at M89 relative to the amino acid sequence set forth in SEQ ID NO:1. In some instances, the mutation is an M89C mutation or an M89F mutation. In some embodiments, the heme protein is an Rma cyt c variant having a mutation at T98 relative to the amino acid sequence set forth in SEQ ID NO:1. In some instances, the mutation is T98V. In some embodiments, the heme protein is an Rma cyt c variant having a mutation at M99 relative to the amino acid sequence set forth in SEQ ID NO:1. In some instances, the mutation is an M99Y mutation, an M99C mutation, or an M99L mutation. Cysteine mutations (including, but not limited to, Y71C, M89C, or M99C) may form disulfide bonds which introduce alterations in protein tertiary structure at the active site, leading to enhancement of organoboron product formation in certain cases.

In some embodiments, the heme protein is an Rma cyt c variant having a mutation at T101 relative to the amino acid sequence set forth in SEQ ID NO:1. In some instances, the mutation is a T101A mutation or a T101L mutation. In some embodiments, the heme protein is an Rma cyt c variant having a mutation at M103 relative to the amino acid sequence set forth in SEQ ID NO:1. In some instances, the mutation is an M103T mutation, an M103D mutation, or an M103F mutation.

The Rma cyt c variants used in the methods can contain any number of mutations in any combination. The variant can contain, for example, an M100 mutation and a V75 mutation. In some embodiments, the Rma cyt c variant contains an M100 mutation, a V75 mutation, and an M103 mutation. In some embodiments, the Rma cyt c variant contains an M100 mutation, a V75 mutation, an M99 mutation, a T101 mutation, and an M103 mutation. In some embodiments, the Rma cyt c variant contains an M100 mutation, a V75 mutation, a Y71 mutation, an M89 mutation, and an M99 mutation. In some embodiments, the Rma cyt c variant contains an M100 mutation, a V75 mutation, an M89 mutation, a T98 mutation, and an M99 mutation.

In some embodiments, the Rma cyt c protein contains a single mutation of the position V75 to any other amino acid. In some embodiments, the Rma cyt c protein contains a single mutation of the residue M103 to any other amino acid. In some embodiments, the Rma cyt c protein contains a single mutation of the residue Y71 to any other amino acid.

In some embodiments, the Rma cyt c protein contains a single mutation of the residue M89 to any other amino acid. In some embodiments, the Rma cyt c protein contains a single mutation of the residue T101 to any other amino acid. In some embodiments, the Rma cyt c protein contains a single mutation of the residue M99 to any other amino acid. In some embodiments, the Rma cyt c protein contains any combination of mutations residues M100, V75, M103, M89, T101, and M99 to any other amino acid.

Mutations analogous to the Rma cyt c proteins may be present in other cytochrome c proteins. For example, an axial variant of horse heart cyt c can comprise a M80 mutation relative to the amino acid sequence set forth in SEQ ID NO:2. A horse heart cyt c variant may contain one or more helix mutations such as a D50 mutation, an A51 mutation, an N52 mutation, a K53 mutation, or an N54 mutation relative to the amino acid sequence set forth in SEQ ID NO:2. An axial variant of human cyt c can comprise a M80 mutation relative to the amino acid sequence set forth in SEQ ID NO:3. A horse heart cyt c variant may contain one or more helix mutations such as an A50 mutation, an A51 mutation, an N52 mutation, a K53 mutation, an N54 mutation, E61 mutation, a D62 mutation, a T63 mutation, an L64 mutation, an M65 mutation, an E66 mutation, a Y67 mutation, an L68 mutation relative to the amino acid sequence set forth in SEQ ID NO:3.

In some embodiments, the heme protein is a cytochrome c protein CYC2_RHOGL (Swiss-prot: P00080) from *Rhodopila globiformis* (*Rhodopsuedomonas globiformis*; Rgl), having the amino acid sequence set forth in SEQ ID NO:4, or a variant thereof. In some embodiments, the heme protein is a mature cytochrome c protein (residues 19-98 of the unprocessed peptide) CY552_HYDTT (Swiss-prot: P15452) from *Hydrogenobacter thermophilus* (strain DSM 6534 I/AM 12695 I TK-6; Hth), having the amino acid sequence set forth in SEQ ID NO: 5, or a variant thereof.

Cytochrome P450 enzymes constitute a large superfamily of heme-thiolate proteins involved in the metabolism of a wide variety of both exogenous and endogenous compounds. Usually, they act as the terminal oxidase in multicomponent electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., *Biochim. Biophys. Acta* 1770, 314 (2007)). P450s typically contain a single polypeptide, ranging from 40 to 55 kDa in molecular weight, and the same general fold has been observed in all P450s with known structures (T. L. Poulous, *Chem Rev.*, 114, 3919 (2014)). The active site of these enzymes contains an $Fe^{III}$-protoporphyrin IX cofactor (heme) ligated proximally by a conserved cysteine thiolate (M. T. Green, *Current Opinion in Chemical Biology* 13, 84 (2009)). The remaining axial iron coordination site is occupied by a water molecule in the resting enzyme, but during native catalysis, this site is capable of binding molecular oxygen. P450 structure is also typically characterized by a long "I helix" (typically around 50 angstroms in length) which runs over the surfaces of the heme and interacts with oxygen and the oxidation substrate. In the presence of an electron source, typically provided by NADH or NADPH from an adjacent fused reductase domain or an accessory cytochrome P450 reductase enzyme, the heme center of cytochrome P450 activates molecular oxygen, generating a high valent iron(IV)-oxo porphyrin cation radical species intermediate and a molecule of water.

Cytochrome P450 BM3 (CYP102A1) proteins are found in the soil bacterium *Bacillus megaterium* and catalyze the NADPH-dependent hydroxylation of long-chain fatty acids at the ω-1 through ω-3 positions. Unlike most other cytochrome P450 proteins, cytochrome P450 BM3 proteins are a natural fusion between the cytochrome P450 domain and an electron donating cofactor. Thus, cytochrome P450 BM3 proteins are useful in a number of biotechnological applications.

In some embodiments, the heme protein used for formation of organoboron products is cytochrome P450 or a variant thereof having one or more mutations. For example, the P450 may be *P. putida* P450cam having the amino acid structure set forth in SEQ ID NO:6 or a variant thereof having one or more mutations. A helix mutation, as described above, may reside within any of the helices at residues 235-264 of SEQ ID NO:6, or within the analogous regions of other P450s such as P450 BM3, also known as CYP102A1 (with a hemoprotein domain containing the amino acid sequence set forth in SEQ ID NO: 7).

In some embodiments, the heme enzyme comprises a globin enzyme. Globins are a superfamily of globular heme proteins that are typically involved in the transport and binding of oxygen. A characteristic of globins is a three-dimensional fold consisting of eight alpha helices, often labeled A-H, that can fold into a three-over-three sandwich structure. Some globins also additional terminal helix extensions. So-called "truncated hemoglobins" contain four alpha helices arranged in a two-over-two sandwich. Globins can be divided into three groups: single-domain globins, flavohemoglobins (not observed in archaea), and globin-coupled sensors (not observed in eukaryotes). All three groups are observed in bacteria. Globin proteins include hemoglobin, myoglobin, neuroglobin, cytoglobin, erythrocruorin, leghemoglobin, non-symbiotic hemoglobin, flavohemoglobins (one group of chimeric globins), globin E, globin-coupled sensors (another group of chimeric globins), protoglobin, truncated 2/2 globin, HbN, cyanoglobin, HbO, and Glb3.

In some embodiments, the heme protein used for formation of organoboron products is a globin or a variant thereof. For example, the globin may be an *M. infernorum* hemoglobin comprising the amino acid sequence set forth in SEQ ID NO:8, or a variant thereof containing one or more mutations. A helix mutation, as described above, may reside within any of the helices at residues 22-34, residues 38-41, residues 47-63, residues 73-84, residues 90-107, and residues 113-131 with respect to SEQ ID NO:8, or within the analogous regions of other globins such those containing a three-over-three helix sandwich fold (including but not limited to, *C. jejuni* globin (SEQ ID NO:9), *V. stercoraria* hemoglobin (SEQ ID NO:10), murine neuroglobin (SEQ ID NO:11), human neuroglobin (SEQ ID NO:12), sperm whale myoglobin (SEQ ID NO:13), human cytoglobin (SEQ ID NO:14), and *A. suum* hemoglobin (SEQ ID NO:15). One or more mutations may reside with the distal binding pocket of *M. infernorum* hemoglobin, such as at F28, Y29, L32, F43, Q44, N45, Q50, K53, L54 and/or V95 with respect to SEQ ID NO:8, or within the analogous regions of other globins such those containing a three-over-three helix sandwich fold.

In some embodiments, the globin is a truncated globin such as *B. subtilis* truncated hemoglobin comprising the amino sequence set forth in SEQ ID NO:16 or a variant thereof having one or more mutations. A helix mutation, as described above, may reside within any of residues 25-29, residues 33-37, residues 44-54, residues 62-65, residues 72-77, residues 85-90, and residues 114-119 with respect to SEQ ID NO:16, or within the analogous regions of other globins such as those containing a two-over-two helix sandwich fold. One or more mutations may reside within the distal binding pocket of *B. subtilis* truncated hemoglobin, for example at T45 and/or at Q49 with respect to SEQ ID NO:16, or at analogous positions of other truncated globins. In some embodiments, the heme protein is a myoglobin or a variant thereof.

Protoglobins were the first globins identified in Archaea such as *M. acetivorans, A. pernix*, and *P. ferrireducens*. Protoglobin tertiary structure frequently includes the canonical globin fold, as well as a pre-A helix (termed "Z" in certain instances) and an N-terminal extension. In some embodiments, the heme protein used for formation of organoboron products is a protoglobin or a variant thereof. For example, the protoglobin may be an *M. acetivorans* protoglobin comprising the amino acid sequence set forth in SEQ ID NO:17, or a variant thereof containing one or more mutations. A helix mutation, as described above, may reside within any of the helices at residues 53-65, residues 69-73, residues 83-102, residues 107-120, residues 140-158, and residues 164-189 with respect to SEQ ID NO:17, or within the analogous regions of other protoglobins such as *A. pernix* protoglobin (containing the amino sequence set forth in SEQ ID NO:18) and *P. ferrireducens* protoglobin (containing the amino sequence set forth in SEQ ID NO:19).

Flavohemoglobins (flavoHbs) are typically characterized by an N-terminal heme b binding globin domain, as well as an FAD binding domain and an NADH binding domain. Electrons are transferred from $NAD^+$/NADH via FAD to heme b, where redox chemistry occurs. Flavohemoglobin activity has been implicated in nitric oxide (NO) detoxification and in NO signaling in organisms such as *E. coli* and *R. eutropha*. Nitric oxide dioxygenases (NODs) include such flavoHbs, as well as globin-type proteins lacking the NADH binding domain or lacking the NADH binding domain and the FAD binding domain. In some embodiments, the heme protein used for formation of organoboron products is an NOD or a variant having one or more mutations in the NOD globin domain. For example, the NOD variant may be a *C. necator* NOD variant containing one or more mutations at any one residues 1-145 in SEQ ID NO:20 (i.e., within the globin domain of the *C. necator* NOD). A helix mutation, as described above, may reside within any of the helices at residues 4-19, residues 21-35, residues 50-67, residues 92-113, and residues 116-145 of SEQ ID NO: 20. Other structurally similar NOD proteins, including *R. marinus* NOD comprising the amino acid sequence set forth in SEQ ID NO:21 may also contain such mutations. In some embodiments, the heme protein is *R. marinus* NOD comprising the amino acid sequence set forth in SEQ ID NO:21, or a variant thereof. In some embodiments, the *R. marinus* NOD variant comprises one or mutations at Y32 or V97 relative to the amino acid sequence set forth in SEQ ID NO:21.

EC 1.11 oxidoreductases (peroxidases) act on peroxide as an acceptor. Non-mammalian peroxidases include Class I intercellular peroxidases, Class II extracellular fungal peroxidases, and Class III extracellular plant peroxidases. All classes are generally characterized by a single polypeptide chain with one heme attached via iron ligation. Class II and Class III peroxidases generally contain disulfide bridges and calcium binding sites, whereas Class I peroxidases do not. The topography of non-mammalian peroxidases, characterized by two all-alpha domains between which the heme group is embedded, is conserved across many species. Animal peroxidases such as myeloperoxidase and the catalytic domain of prostaglandin H synthase, also exhibit mainly helical structures. In some embodiments, the heme protein used for formation of organoboron products is a peroxidase or a variant thereof. For example, the peroxidase variant may be a yeast cytochrome c peroxidase (CCP) comprising the amino acid sequence set forth in SEQ ID NO:22, or a variant thereof containing one or more mutations. A helix mutation, as described above, may reside within any of the helices at residues 43-55 and residues 165-174 with respect to SEQ ID NO:22. More particularly, the variant may contain mutations at R48, W51, or H52 in the distal heme pocket of CCP. In some embodiments, peroxidase variant may be a horseradish peroxidase (HRP) comprising the amino acid sequence set forth in SEQ ID NO:23, or variant thereof containing one or more mutations. A helix mutation, as described above, may reside within any of the helices at residues 31-44, residues 145-154, residues 161-166, residues 245-249, and residues 271-285 with respect to SEQ ID NO:23. The variant may contain mutations at R38, H40, F41, or H42 in the distal heme pocket of HRP. Mutations or cysteine residues at C11, C91, C44, C49, C97, C301, C177, or C209 of HRP may also be included.

Heme-containing catalases catalyze the decomposition of hydrogen peroxide to oxygen and water (EC 1.11.1.6). Catalases have been identified in numerous organisms including bacteria, humans, and other mammals. A number of catalases (e.g., human erythrocyte catalase having the sequence set forth in SEQ ID NO:24) are tetramers, where each of the four subunits is characterized by a hydrophobic core containing an eight-stranded β-barrel and a C-terminal helical domain. Each subunit also contains a wrapping loop between the β-barrel and the C-terminal helical domain, as well as an N-terminal threading arm. The threading arm of one subunit hooks through the wrapping loop of another subunit to form a subunit dimer, and two dimers assemble to form the tetramer. The heme prosthetic group in each subunit is packed against the β2 strand, the β3 strand, and the β4 strand, and held between the α4 helix and the α12 helix. Upon tetramer assembly, each heme is contacted by the α2 helix of an adjacent subunit. The heme iron is pentacoordinate, bound by Y358, and the porphyrin carboxylates are neutralized by neighboring R72, R112, and R72 residues. Certain bacterial catalases (e.g., *E. coli* catalase HPII having subunits with the sequence set forth in SEQ ID NO:25) are characterized by larger subunits but share the β-barrel core structure and homotetrameric quaternary structure. In some embodiments, the heme protein used for formation of organoboron products is a catalase or a variant thereof. For example, the catalase variant may be a human erythrocyte catalase variant containing one or more mutations in SEQ ID NO:24. A helix mutation, as described above, may reside within any of the helices at residues 55-63, residues 158-167, and residues 349-364 of SEQ ID NO:24, or within the analogous regions of SEQ ID NO:25 and other like sequences.

In certain embodiments, the heme protein is a fragment thereof comprising the heme domain. In some embodiments, the cofactor of the heme protein is the native heme cofactor. In other embodiments, the cofactor of the heme protein is modified or replaced by a non-native cofactor (i.e., metals other than iron), including, but not limited to, cobalt, rhodium, copper, ruthenium, iridium, and manganese, which are active carbon-boron bond formation catalysts.

One skilled in the art will understand that heme protein mutants identified as improved in the formation of carbon-boron bond can themselves be subjected to additional mutagenesis and screening to find improvements as described herein, resulting in progressive, cumulative improvements in one or more reaction parameters including but not limited to turnover frequency, total turnover number, yield, chemoselectivity, regioselectivity, diastereoselectivity, enantioselectivity, expression, thermostability, or solvent tolerance.

In some embodiments, the heme protein, homolog, variant, or fragment thereof has a turnover frequency (TOF) between about 1 min$^{-1}$ and 10 min$^{-1}$ (e.g., about 1 min$^{-1}$, 1.5 min$^{-1}$, 2 min$^{-1}$, 2.5 min$^{-1}$, 3 min$^{-1}$, 3.5 min$^{-1}$, 4 min$^{-1}$, 4.5 min$^{-1}$, 5 min$^{-1}$, 5.5 min$^{-1}$, 6 min$^{-1}$, 6.5 min$^{-1}$, 7 min$^{-1}$, 7.5 min$^{-1}$, 8 min$^{-1}$, 8.5 min$^{-1}$, 9 min$^{-1}$, 9.5 min$^{-1}$, or 10 min$^{-1}$). In other embodiments, the TOF is between about 10 min$^{-1}$ and 100 min$^{-1}$ (e.g., about 10 min$^{-1}$, 11 min$^{-1}$, 12 min$^{-1}$, 13 min$^{-1}$, 14 min$^{-1}$, 15 min$^{-1}$, 16 min$^{-1}$, 17 min$^{-1}$, 18 min$^{-1}$, 19 min$^{-1}$, 20 min$^{-1}$, 21 min$^{-1}$, 22 min$^{-1}$, 23 min$^{-1}$, 24 min$^{-1}$, 25 min$^{-1}$, 26 min$^{-1}$, 27 min$^{-1}$, 28 min$^{-1}$, 29 min$^{-1}$, 30 min$^{-1}$, 31 min$^{-1}$, 32 min$^{-1}$, 33 min$^{-1}$, 34 min$^{-1}$, 35 min$^{-1}$, 36 min$^{-1}$, 37 min$^{-1}$, 38 min$^{-1}$, 39 min$^{-1}$, 40 min$^{-1}$, 41 min$^{-1}$, 42 min$^{-1}$, 43 min$^{-1}$, 44 min$^{-1}$, 45 min$^{-1}$, 46 min$^{-1}$, 47 min$^{-1}$, 48 min$^{-1}$, 49 min$^{-1}$, 50 min$^{-1}$, 55 min$^{-1}$, 60 min$^{-1}$, 65 min$^{-1}$, 70 min$^{-1}$, 75 min$^{-1}$, 80 min$^{-1}$, 85 min$^{-1}$, 90 min$^{-1}$, 95 min$^{-1}$, or 100 min$^{-1}$). In other instances, the TOF is greater than about 100 min$^{-1}$ to 1,000 min$^{-1}$ (e.g., greater than about 100 min$^{-1}$, 150 min$^{-1}$, 200 min$^{-1}$, 250 min$^{-1}$, 300 min$^{-1}$, 350 min$^{-1}$, 400 min$^{-1}$, 450 min$^{-1}$, 500 min$^{-1}$, 550 min$^{-1}$, 600 min$^{-1}$, 650 min$^{-1}$, 700 min$^{-1}$, 750 min$^{-1}$, 800 min$^{-1}$, 850 min$^{-1}$, 900 min$^{-1}$, 950 min$^{-1}$, 1,000 min$^{-1}$, or more). In some instances, the TOF is greater than about 10 min$^{-1}$. In other instances, the TOF is greater than about 45 min$^{-1}$.

In other embodiments, the heme protein, homolog, variant, or fragment thereof has a total turnover number (TTN), which refers to the maximum number of molecules of a substrate that the protein can convert before becoming inactivated, of between about 1 and 100 (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In some other embodiments, the TTN is between about 100 and 1,000 (e.g., about 100, 150, 200, 250, 300, 350, 400, 450, 500, 550, 600, 650, 700, 750, 800, 850, 900, 950, or 1,000). In some embodiments, the TTN is between about 1,000 and 2,000 (e.g., about 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 or 2,000). In other embodiments, the TTN is at least about 2,000 (e.g., at least about 2,000, 2,500, 3,000, 3,500, 4,000, 4,500, 5,000, 5,500, 6,000, 6,500, 7,000, 7,500, 8,000, 8,500, 9,000, 9,500, or 10,000). In some instances, the TTN is greater than about 70. In other instances, the TTN is greater than about 1,800.

In some embodiments, the heme protein variant or fragment thereof has enhanced activity of at least about 1.5 to 2,000 fold (e.g., at least about 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, or more) fold compared to the corresponding wild-type heme protein.

In some embodiments, activity is expressed in terms of turnover frequency (TOF). In particular embodiments, the TOF of the heme protein variant or fragment thereof is at least about 1.5, 2, 2.5, 3, 3.5, 4, 4.5, 5, 5.5, 6, 6.5, 7, 7.5, 8, 8.5, 9, 9.5, or 10 fold higher than the corresponding wild-type protein.

In other instances, activity is expressed in terms of total turnover number (TTN). In particular instances, the TTN of the theme protein variant or fragment thereof is about at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 fold higher than the corresponding wild-type protein.

In some embodiments, the present invention provides heme proteins, homologs, variants, and fragments thereof that catalyze enantioselective carbene insertion into boron-hydrogen bonds with high enantiomeric excess. In particular embodiments, the heme proteins are variants or fragments thereof that catalyze enantioselective carbene insertion into boron-hydrogen bonds with higher enantiomeric excess values than that of the corresponding wild-type protein. In some embodiments, the heme protein, homolog, variants, or fragment thereof catalyzes carbene insertion into boron-hydrogen bonds with an enantiomeric excess value of at least about 30% ee (e.g., at least about 30%, 35%, 40%, 45%, 50%, 55%, 60%, 65%, 70%, 75%, 80%, 85%, 90%, 95%, or 100% ee). Preferably, the heme protein, homolog, variant, or fragment thereof catalyzes carbene insertion into boron-hydrogen bonds with at least about 80% ee (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100% ee). More preferably, the heme protein, homolog, variant, or fragment thereof catalyzes carbene insertion into boron-hydrogen bonds with at least about 95% ee (e.g., at least about 95%, 96%, 97%, 98%, 99%, or 100% ee).

In certain embodiments, a conserved residue in a heme protein of interest that serves as an heme axial ligand can be identified by locating the segment of the DNA sequence in the corresponding gene which encodes the conserved residue. In some instances, this DNA segment is identified through detailed mutagenesis studies in a conserved region of the protein. In other instances, the conserved residue is identified through crystallographic study.

In situations where detailed mutagenesis studies and crystallographic data are not available for a heme protein of interest, the axial ligand may be identified through phylogenetic study. Due to the similarities in amino acid sequence within families of heme proteins (e.g., cytochrome c proteins), standard protein alignment algorithms may show a phylogenetic similarity between a heme protein for which crystallographic or mutagenesis data exist and a new heme protein for which such data do not exist. Thus, the polypeptide sequences of the present invention for which the heme axial ligand is known can be used as a "query sequence" to perform a search against a specific new heme protein of interest or a database comprising heme protein sequences to identify the heme axial ligand. Such analyses can be performed using the BLAST programs (see, e.g., Altschul et al., *J Mol. Biol.* 215(3):403-10(1990)). Software for performing BLAST analyses publicly available through the National Center for Biotechnology Information. BLASTP is used for amino acid sequences.

Exemplary parameters for performing amino acid sequence alignments to identify the heme axial ligand in a heme protein of interest using the BLASTP algorithm include E value=10, word size=3, Matrix=Blosum62, Gap opening=11, gap extension=1, and conditional compositional score matrix adjustment. Those skilled in the art will know what modifications can be made to the above parameters, e.g., to either increase or decrease the stringency of the comparison and/or to determine the relatedness of two or more sequences.

In some embodiments, the heme protein comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., the amino acid sequence set forth in SEQ ID NO:1). In other embodiments, the heme protein comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., the amino acid sequence set forth in SEQ ID NO:1). In particular embodiments, the heme protein comprises an amino acid sequence that has about 90% or greater (e.g., about 90%, 91%, 92%, 93%, 94%, 95%, 96%, 97%, 98%, 99%, or 100%) identity any of the amino acid sequences described herein (e.g., the amino acid sequence set forth in SEQ ID NO:1). In some instances, the heme protein comprises an amino acid sequence that is about 95%, 96,%, 97%, 98%, 99%, or 100% identical any of the amino acid sequences described herein (e.g., the amino acid sequence set forth in SEQ ID NO:1).

In some embodiments, the heme protein comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NO:1. The amino acids may be contiguous, or separated by any number of amino acids.

In certain embodiments, mutations can be introduced into the target gene using standard cloning techniques (e.g., site-directed mutagenesis, site-saturated mutagenesis) or by gene synthesis to produce the heme proteins, fragments thereof, variants thereof, or homologs thereof of the present invention.

In some embodiments, the heme protein, fragment thereof, variant thereof, or homolog thereof is recombinantly expressed and optionally isolated and/or purified for carrying out the in vitro boron-hydrogen carbene insertion reactions of the present invention. In other embodiments, the heme protein, fragment thereof, variant thereof, or homolog thereof is expressed in whole cells such as bacterial cells, archaeal cells, yeast cells, fungal cells, insect cells, plant cells, or mammalian cells, and these cells are used for carrying out the in vivo boron-hydrogen carbene insertion reactions of the present invention. The wild-type or mutated gene can be expressed in a whole cell using an expression vector under the control of an inducible promoter or by means of chromosomal integration under the control of a constitutive promoter. Boron-hydrogen carbene insertion activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NSO hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, the present invention provides the heme proteins, fragments thereof, variants thereof, or homologs thereof, such as the cytochrome c variants described herein that are active boron-hydrogen carbene insertion catalysts, inside living cells. As a non-limiting example, bacterial cells (e.g., *E. coli*) can be used as host whole cell catalysts for the in vivo boron-hydrogen carbene insertion reactions of the present invention, although any number of host whole cells may be used, including but not limited to the host cells described herein. In some embodiments, host whole cell catalysts containing heme proteins, fragments thereof, variants thereof, or homologs thereof are found to significantly enhance the total turnover number (TTN) compared to the in vitro reactions using isolated heme proteins, fragments thereof, variants thereof, or homologs thereof.

The expression vector comprising a nucleic acid sequence that encodes a heme protein, fragment thereof, variant thereof, or homolog thereof of the invention can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme protein, fragment thereof, variant thereof, or homolog thereof that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a heme protein that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:1. In other embodiments, the nucleic acid sequence encodes a heme protein that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:1. In particular embodiments, the nucleic acid sequence encodes a heme protein that comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NO:1. In some instances, the nucleic acid sequence encodes a heme protein that comprises an amino acid sequence that is about 95%, 96,%, 97%, 98%, 99%, or 100% identical to the amino acid sequence set forth in SEQ ID NO:1.

In other embodiments, the nucleic acid sequence encodes a heme protein that comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NO:1. The amino acids may be contiguous, or separated by any number of amino acids.

It is understood that affinity tags may be added to the N- and/or C-terminus of a heme protein, fragment thereof, variant thereof, or homolog thereof expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

B. Organoboron Products

The methods of the invention can be used to provide a number of organoboron products. The organoboron products include several classes of compound including, but not limited to, pharmaceutical compounds (i.e., drugs, therapeutic agents, etc.), reagents for chemical synthesis, and functional materials such as sensors for biological molecules and other targets. Examples of pharmaceutical compounds that can be prepared using the methods of the invention include, but are not limited to, proteasome inhibitors (including, e.g., bortezomib described by Gupta in U.S. Pat. No. 6,713,446 and WO 02/059130, as well as ixazomib as described by Olhava et al. in U.S. Pat. No. 7,442,830 and WO 2009/020448), antifungal agents (including, e.g., tavaborole and other leucyl-tRNA synthetase inhibitors described by Baker et al. in U.S. Pat. No. 7,582,621 and WO 2006/089067), and phosphodiesterase-4-ihibitors (including, e.g., crisaborole and other compounds described by Baker et al. in U.S. Pat. No. 8,039,451). Examples of reagents for chemical synthesis include, but are not limited to, boronic esters (including, but not limited to, alkenyl boronates) which can be used for cross-couplings such Suzuki reactions; vinyloxyboranes which can be used in in aldol-type reactions as developed by Mukaiyama and other; and triorganoboranes (e.g., triallyl-boron, B-allyldiisopinocamphenylborane, and the like) which can be used as alkylating reagents.

In some embodiments, the methods of the present invention for producing organoboron products comprise combining a boron-containing reagent, a carbene precursor, and a heme protein, homolog thereof, variant thereof, or fragment thereof as described herein under conditions sufficient to form an organoboron product.

In some embodiments, the organoboron product is a compound according to Formula III:

(III)

wherein:

X is

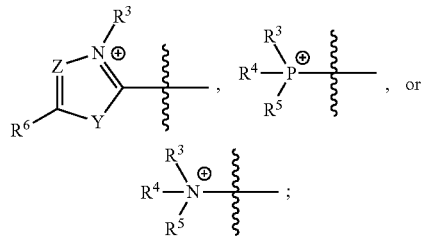

the wavy line represents the point of connection between X and the boron atom;

Y is selected from the group consisting of $NR^4$, $C(R^4)_2$, O, and S;

Z is selected from the group consisting of N and $CR^5$;

$R^1$ and $R^2$ are independently selected from the group consisting of H, optionally substituted $C_{1-18}$ alkyl, optionally substituted $C_{1-18}$ alkoxy, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^{1a}$ is selected from the group consisting of H, optionally substituted $C_{1-18}$ alkyl, optionally substituted $C_{1-18}$ alkoxy, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^3$, $R^4$, $R^5$, and $R^6$ are independently selected from the group consisting of H, optionally substituted $C_{1-18}$ alkyl, optionally substituted $C_{1-18}$ alkoxy, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

any two of $R^3$, $R^4$, $R^5$, and $R^6$ are optionally taken together with the atoms to which they are attached to form a 5- or 6-membered ring when X is

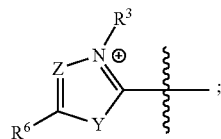

any two of $R^3$, $R^4$, and $R^5$ are optionally taken together with the nitrogen atom to which they are connected to form optionally substituted 6- to 10-membered heterocyclyl or $R^3$, $R^4$, and $R^5$ are optionally taken together with the nitrogen atom to which they are connected to form optionally substituted 6- to 10-membered heteroaryl when X is

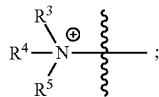

and
each $R^7$, $R^8$, and $R^9$ is independently selected from the group consisting of H, optionally substituted $C_{1-18}$ alkyl, optionally substituted $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some embodiments, the organoboron product is a compound according to Formula IV:

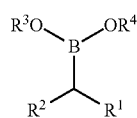

wherein
$R^1$ and $R^2$ are independently selected from the group consisting of H, optionally substituted $C_{1-18}$ alkyl, optionally substituted $C_{1-18}$ alkoxy, $C_{1-18}$ haloalkyl, $C_2$-18 alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^{1a}$ is selected from the group consisting of H, optionally substituted $C_{1-18}$ alkyl, optionally substituted $C_{1-18}$ alkoxy, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $C(O)R^{1a}$, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^3$ and $R^4$ are independently selected from the group consisting of H, optionally substituted $C_{1-18}$ alkyl, optionally substituted $C_{1-18}$ alkoxy, $C_{1-18}$ haloalkyl, $C_2$-18 alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, optionally substituted $C_{1-18}$ alkyl, optionally substituted $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

Compounds of Formula III and Formula IV can be formed via the heme protein-catalyzed reaction of a carbene precursor according to Formula I:

with a boron-containing reagent according to Formula IIa, IIb, IIc, or IId:

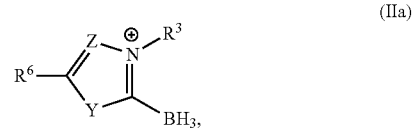

A number of carbene precursors can be used in the methods and reaction mixtures of the invention including, but not limited to, amines, azides, hydrazines, hydrazones, epoxides, diazirenes, and diazo reagents. In some embodiments, the carbene precursor is an epoxide (i.e., a compound containing an epoxide moiety). The term "epoxide moiety" refers to a three-membered heterocycle having two carbon atoms and one oxygen atom connected by single bonds. In some embodiments, the carbene precursor is a diazirene (i.e., a compound containing a diazirine moiety). The term "diazirine moiety" refers to a three-membered heterocycle having one carbon atom and two nitrogen atoms, wherein the nitrogen atoms are connected via a double bond. Diazirenes are chemically inert, small hydrophobic carbene precursors described, for example, in US 2009/0211893, by Turro (*J. Am. Chem. Soc.* 1987, 109, 2101-2107), and by Brunner (*J. Biol. Chem.* 1980, 255, 3313-3318), which are incorporated herein by reference in their entirety.

In some embodiments, the carbene precursor is a diazo reagent, e.g., an α-diazoester, an α-diazoamide, an α-diazonitrile, an α-diazoketone, an α-diazoaldehyde, and an α-diazosilane. Diazo reagents can be formed from a number of starting materials using procedures that are known to those of skill in the art. Ketones (including 1,3-diketones), esters (including β-ketones), acyl chlorides, and carboxylic acids can be converted to diazo reagents employing diazo transfer conditions with a suitable transfer reagent (e.g., aromatic and aliphatic sulfonyl azides, such as toluenesulfonyl azide, 4-carboxyphenylsulfonyl azide, 2-naphthalenesulfonyl azide, methylsulfonyl azide, and the like) and a suitable base (e.g., triethylamine, triisopropylamine, diazobicyclo[2.2.2]octane, 1,8-diazabicyclo[5.4.0]undec-7-ene, and the like) as described, for example, in U.S. Pat. No. 5,191,069 and by Davies (*J. Am. Chem. Soc.* 1993, 115, 9468-9479), which are incorporated herein by reference in their entirety. The preparation of diazo compounds from azide and hydrazone precursors is described, for example, in U.S. Pat. Nos. 8,350,014 and 8,530,212, which are incorporated herein by reference in their entirety. Alkylnitrite reagents (e.g., (3-methylbutyl)nitrite) can be used to convert α-aminoesters to the corresponding diazo compounds in non-aqueous media as described, for example, by Takamura (*Tetrahedron,* 1975, 31: 227), which is incorporated herein by reference in its entirety. Alternatively, a diazo compound can be formed from an aliphatic amine, an aniline or other arylamine, or a hydrazine using a nitrosating agent (e.g., sodium nitrite) and an acid (e.g., p-toluenesulfonic acid) as described, for example, by Zollinger (*Diazo Chemistry I and II,* VCH Weinheim, 1994) and in US 2005/0266579, which are incorporated herein by reference in their entirety.

In some embodiments, $R^1$ is $C(O)R^{1a}$ in compounds according to Formula I and Formula III or Formula IV. In some such embodiments, $R^{1a}$ is optionally substituted $C_{1-6}$ alkyl or optionally substituted $C_{1-6}$ alkoxy. In some embodiments, $R^{1a}$ is optionally substituted $C_{1-6}$ alkyl (e.g., the carbene precursor is a diazoketone). In some embodiments, $R^{1a}$ is optionally substituted $C_{1-6}$ alkoxy (e.g., the carbene precursor is a diazoester). For example, $R^{1a}$ can be optionally substituted methoxy (e.g., benzyloxy), optionally substituted ethoxy, optionally substituted n-propoxy, optionally substituted isopropoxy, optionally substituted n-butoxy, optionally substituted isobutoxy, or optionally substituted t-butoxy. $R^{1a}$ can be methyl, ethyl, n-propyl, isopropyl, n-butyl, isobutyl, sec-butyl, tert-butyl, n-pentyl, isopentyl, n-hexyl.

In some embodiments, $R^1$ is $C_{1-6}$ haloalkyl in compounds according to Formula I and Formula III or Formula IV. For example, $R^1$ can be chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like.

In some embodiments, $R^2$ in compounds of Formula I and Formula III or Formula IV is $C_{1-6}$ alkyl or $C_{6-10}$ aryl. For example, $R^2$ can be methyl, ethyl, n-propyl, isopropyl, n-butyl, isobutyl, sec-butyl, tert-butyl, n-pentyl, isopentyl, n-hexyl, phenyl, naphthyl, or anthracenyl.

In some embodiments, $R^1$ is $C(O)R^{1a}$, $R^{1a}$ is optionally substituted $C_{1-6}$ alkoxy, and $R^2$ is $C_{1-6}$ alkyl. In some embodiments, $R^1$ is $C(O)R^{1a}$, $R^{1a}$ is optionally substituted $C_{1-6}$ alkoxy, and $R^2$ is $C_{6-10}$ aryl. In some embodiments, $C_{1-6}$ haloalkyl and $R^2$ is $C_{1-6}$ alkyl. In some embodiments, $C_{1-6}$ haloalkyl and $R^2$ is $C_{6-10}$ aryl.

In some embodiments, the invention provides methods and reaction mixtures for producing an organoboron product wherein the carbene precursor is an amine. In some embodiments, the amine is converted to a diazo reagent by contacting the amine with a nitrosating agent under conditions sufficient to form the diazo reagent. In some embodiments, the nitrosating agent is selected from the group consisting of sodium nitrite, potassium nitrite, lithium nitrite, calcium nitrite, magnesium nitrite, ethyl nitrite, n-butyl nitrite, and (3-methylbutyl)nitrite. In the some embodiments, the amine is contacted with the nitrosating agent in the presence of an acid. Examples of suitable acids include, but are not limited to, sulfonic acids (e.g., p-toluenesulfonic acid, methanesulfonic acid, and the like), phosphoric acid, nitric acid, sulfuric acid, and hydrochloric acid. In some embodiments, the nitrosating agent is sodium nitrite. In some embodiments, the nitrosating agent is sodium nitrite and the acid is p-toluenesulfonic acid. In some embodiments, the nitrosating agent is sodium nitrite, the acid is p-toluenesulfonic acid, and the amine is selected from the group consisting of an alkylamine, an arylamine, an α-aminoketone, an α-aminoester, and an α-aminoamide. In some embodiments, the amine is contacted with the nitrosating reagent (and the acid, when used) in a suitable organic solvent (e.g., acetonitrile, N,N-dimethylformamide, dimethylsulfoxide, and the like) for a time sufficient to form the diazo reagent prior to combination with the boron-containing reagent and the heme protein used for forming the organoboron product. The diazo reagent in the organic solvent can then be combined with a mixture containing the boron-containing reagent and the heme protein. In some embodiments, the mixture containing the boron-containing reagent and the heme protein is an aqueous mixture containing a suitable buffer as described below. Alternatively, the amine can be converted to the diazo reagent in situ, by combining the amine, the nitrosating agent, and the acid (when used) directly with the boron-containing reagent and the heme protein.

In some embodiments, the boron-containing reagent contains a borane-Lewis base complex. Examples of Lewis bases include, but are not limited to, carbenes, ammonia, primary amines, secondary amines, tertiary amines, organophosphines, organosulfur compounds, alcohols, ethers, and water. In some embodiments, the borane-Lewis base complex is a borane-N-heterocyclic carbene (NCH) complex. The N-heterocyclic moiety in the borane-NHC complex can be, for example, an optionally substituted imidazol-3-ium-2-yl moiety, an optionally substituted 1,2,4-triazol-1-ium-5-yl moiety, an optionally substituted tetrazol-4-ium-5-yl moiety, an optionally substituted pyrazol-1-ium-5-yl moiety, an optionally substituted benzimidazol-3-ium-2-yl moiety, an optionally substituted oxazol-3-ium-2-yl moiety, or an optionally substituted thiazol-3-ium-2-yl moiety.

In some embodiments, the N-heterocyclic moiety is an optionally substituted imidazol-3-ium-2-yl moiety or an optionally substituted 1,2,4-triazol-1-ium-5-yl moiety. In some embodiments, the N-heterocyclic moiety is 1,3-dimethyl-1H-imidazol-3-ium-2-yl or 1,4-dimethyl-4H-1,2,4-triazol-1-ium-5-yl.

In some embodiments, the boron-containing reagent is a compound according to Formula IIa:

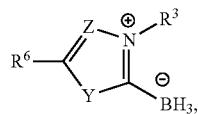
(IIa)

wherein
Y is selected from the group consisting of NR$^4$, C(R$^4$)$_2$, O, and S
Z is selected from the group consisting of N and CR$^5$;
R$^3$, R$^4$, R$^5$, and R$^6$ are independently selected from the group consisting of H, optionally substituted C$_{1-18}$ alkyl, optionally substituted C$_{1-18}$ alkoxy, C$_{1-18}$ haloalkyl, C$_{2-18}$ alkenyl, C$_{2-18}$ alkynyl, optionally substituted C$_{6-10}$ aryl, optionally substituted 6- to 10-membered heteroaryl, optionally substituted 6- to 10-membered heterocyclyl, cyano, halo, nitro, N(R$^8$)$_2$, B(R$^9$)$_3$, Si(R$^9$)$_3$, C(O)OR$^7$, C(O)SR$^7$, C(O)N(R$^7$)$_2$, C(O)R$^7$, C(O)ON(R$^7$)$_2$, C(O)NR$^7$OR$^8$, C(O)C(O)OR$^7$, and P(O)(OR$^7$)$_2$; or
any two of R$^3$, R$^4$, R$^5$, and R$^6$ are taken together with the atoms to which they are attached to form a 5- or 6-membered ring; and
each R$^7$, R$^8$, and R$^9$ is independently selected from the group consisting of H, optionally substituted C$_{1-18}$ alkyl, optionally substituted C$_{1-18}$ alkoxy, C$_{2-18}$ alkenyl, C$_{2-18}$ alkynyl, optionally substituted C$_{6-10}$ aryl, optionally substituted 6- to 10-membered heteroaryl, and optionally substituted 6- to 10-membered heterocyclyl.

In embodiments, where the boron-containing reagent is a compound according to Formula IIa, the Y, Z, and R$^3$-R$^9$ groups in the organoboron product according to Formula III are defined as for Formula IIa. In some such embodiments, R$^1$ and R$^2$ in the organoboron product according to Formula III are defined as above.

In some embodiments, the boron-containing reagent has the formula:

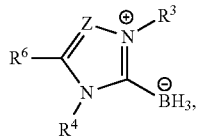

wherein Z is N or CR$^5$.

In some embodiments, Y is NR$^4$ and Z is CR$^5$ in the compound of Formula IIa or the compound of Formula III. In some such embodiments, R$^4$ is C$_{1-6}$ alkyl. R$^4$ can be, for example, methyl, ethyl, n-propyl, isopropyl, n-butyl, isobutyl, sec-butyl, tert-butyl, n-pentyl, isopentyl, or n-hexyl. In some such embodiments, R$^3$ is C$_{1-6}$ alkyl or R$^3$ is C$_{2-6}$ alkenyl.

In some embodiments, Y is NR$^4$, Z is CR$^5$, and R$^5$ is selected from H, halogen, C$_{1-6}$ alkyl, and C$_{1-6}$ haloalkyl. R$^5$ can be, for example, hydrogen, fluoro, chloro, bromo, iodo, methyl, ethyl, n-propyl, isopropyl, n-butyl, isobutyl, sec-butyl, tert-butyl, n-pentyl, isopentyl, n-hexyl, chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, or 1,1,1,3,3,3-hexafluoropropyl. In some such embodiments, R$^6$ is independently selected from H, halogen, C$_{1-6}$ alkyl, and C$_{1-6}$ haloalkyl.

In some embodiments, the boron-containing reagent is a compound according to Formula IIa, wherein R$^3$ is methyl, ethyl, n-propyl, isopropyl, n-butyl, isobutyl, sec-butyl, tert-butyl, n-pentyl, isopentyl, n-hexyl, vinyl, or allyl; Y is NR$^4$; R$^4$ is methyl, ethyl, n-propyl, isopropyl, n-butyl, isobutyl, sec-butyl, tert-butyl, n-pentyl, isopentyl, n-hexyl, vinyl, or allyl; Z is CR$^5$; R$^5$ is H, methyl, ethyl, n-propyl, isopropyl, n-butyl, isobutyl, sec-butyl, tert-butyl, fluoro, chloro, chloromethyl, dichloromethyl, trichloromethyl, fluoromethyl, difluoromethyl, or trifluoromethyl; and R$^6$ is H, methyl, ethyl, n-propyl, isopropyl, n-butyl, isobutyl, sec-butyl, tert-butyl, fluoro, chloro, chloromethyl, dichloromethyl, trichloromethyl, fluoromethyl, difluoromethyl, or trifluoromethyl.

In some embodiments, the boron-containing reagent is a compound according to Formula IIa, wherein R$^3$ is methyl, ethyl, n-propyl, isopropyl, n-butyl, isobutyl, sec-butyl, tert-butyl, n-pentyl, isopentyl, n-hexyl, vinyl, or allyl; Y is NR$^4$; R$^4$ is methyl, ethyl, n-propyl, isopropyl, n-butyl, isobutyl, sec-butyl, or tert-butyl; Z is N; and R$^6$ is H, methyl, ethyl, n-propyl, isopropyl, n-butyl, isobutyl, sec-butyl, tert-butyl, fluoro, chloro, chloromethyl, dichloromethyl, trichloromethyl, fluoromethyl, difluoromethyl, or trifluoromethyl.

In some embodiments, the boron-containing reagent is selected from:

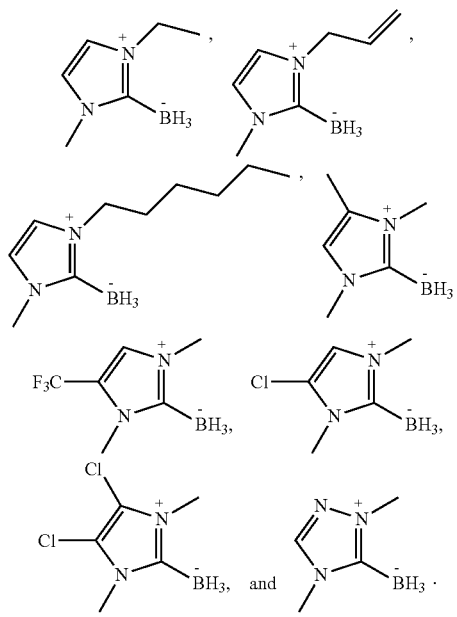

Figure 6A:
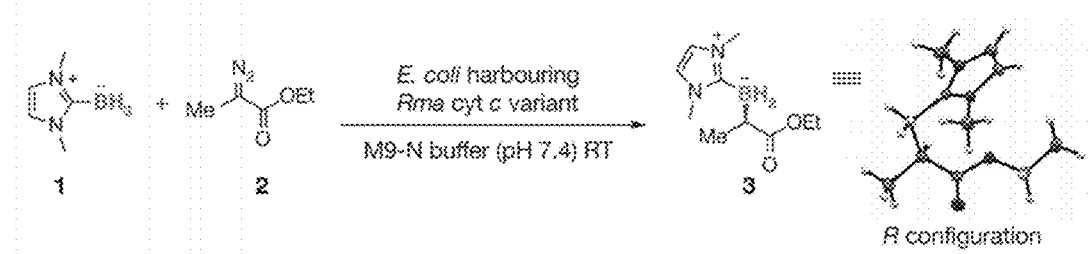
FIG. 6A shows a reaction scheme for a representative in vivo borylation reaction between NHC-borane 1 and diazo ester 2 to yield organoborane 3. Standard substrate loading is 10 mM for both 1 and 2. The absolute configuration of biosynthesized 3 was assigned to be R by X-ray crystallography.

NHC-boranes can be prepared from a free carbene and a borane complex (e.g., a borane ether complex or a borane sulfide complex) with a base such a sodium hexamethyldisilazide (NaHMDS) or potassium tert-butoxide. Amineboranes can also be used for NHC-borane formation. Free carbenes are can be conveniently prepared by in situ deprotonation of azolium salts. For example, the treatment of 1,3-dimethylimidazolium iodide with NaHMDS in tetrahydrofuran, followed by addition of tetrahydrofuran-borane, can be used to prepare (1,3-dimethyl-1H-imidazol-3-ium-2-yl)trihydroborate (compound 1 as shown in FIG. 6A). NHC—BH$_3$ complexes can often be easily obtained as solids which are stable to air, moisture, chromatography purification, and storage. These features make them advantageous as starting points for the preparation of other substituted boranes. Also advantageously, NHC-boranes are stable under aqueous conditions suitable for enzyme-catalyzed reactions.

In some embodiments, the borane-Lewis base complex comprises an amine moiety or a phosphine moiety. Examples of such complexes include, but are not limited to, borane-triethylamine, borane-diisopropylamine, borane-dimethylamine, borane-pyridine, borane-tert-butylamine, borane-triphenylphosphine, borane di(tert-butyl)phosphine, 2-methylpyridine borane, and the like.

In some embodiments, the boron-containing reagent is a compound according to Formula IIb:

wherein
$R^3$, $R^4$, and $R^5$, are independently selected from the group consisting of H, optionally substituted $C_{1-18}$ alkyl, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, optionally substituted $C_{1-18}$ alkyl, optionally substituted $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some embodiments, the boron-containing reagent is a compound according to Formula IIc:

wherein
$R^3$, $R^4$, and $R^5$, are independently selected from the group consisting of H, optionally substituted $C_{1-18}$ alkyl, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

any two of $R^3$, $R^4$, and $R^5$ are optionally taken together with the nitrogen atom to which they are connected to form optionally substituted 6- to 10-membered heterocyclyl;

$R^3$, $R^4$, and $R^5$ are optionally taken together with the nitrogen atom to which they are connected to form optionally substituted 6- to 10-membered heteroaryl;

each $R^7$, $R^8$, and $R^9$ is independently selected from the group consisting of H, optionally substituted $C_{1-18}$ alkyl, optionally substituted $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some embodiments, the boron-containing reagent is a compound according to Formula IIc wherein two of $R^3$, $R^4$, and $R^5$ are optionally taken together with the nitrogen atom to which they are connected to form optionally substituted 6- to 10-membered heterocyclyl. In some embodiments, the boron-containing reagent is a compound according to Formula IIc wherein $R^3$, $R^4$, and $R^5$ are taken together with the nitrogen atom to which they are connected to form optionally substituted 6- to 10-membered heteroaryl. In some embodiments, $R^3$, $R^4$, and $R^5$ are taken together with the nitrogen atom to which they are connected to form optionally substituted pyridine (e.g., 2-methylpyridine).

In some embodiments, the boron-containing reagent comprises a boronate ester. (e.g., compounds of Formula IId). Examples of boronate esters include, but are not limited to, tributyl borate, catecholborane, and phenylboronic acid esters (e.g., phenylboronic acid pinacol ester).

In some embodiments, the boron-containing reagent is a compound according to Formula IId:

wherein
$R^3$ and $R^4$ are independently selected from the group consisting of H, optionally substituted $C_{1-18}$ alkyl, $C_{1-18}$ haloalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_3$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, optionally substituted $C_{1-18}$ alkyl, optionally substituted $C_{1-18}$ alkoxy, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some embodiments, the boron-containing reagent is a carborane. Carboranes are a family of polyhedral borane clusters and have fascinating properties for multiple biomedical applications. See, e.g., Dash et al in *Boron Science*; CRC Press, 2011. Because of their hydrophobicity and unique three-dimensional structures, there has been a growing interest in using carboranes as pharmacophores for drug design. See, e.g., Issa, et al. *Chem. Rev.* 2011, 111, 5701-5722. In addition, the rich boron content of carborane makes these compounds ideal carriers for boron neutron capture therapy (BNCT). See, e.g., Barth, et al. *Clin. Cancer Res.* 2005, 11, 3987-4002. These important biomedical applications necessitate the development of methods for selective functionalization of carboranes. Currently, most carboranes are modified at two CH units because of the ease of access to these sites. See, e.g., Xie, et al. *Science China Chemistry*

2014, 57, 1061-1063; Olid, et al. *Chem. Soc. Rev.* 2013, 42, 3318-3336). Selective boron modification remains a challenging synthetic proposition, as there are multiple similar BH units present in carboranes. See, e.g., Qiu, et al. *Tetrahedron Lett.* 2015, 56, 963-971. This limitation greatly restricts the diversity of carboranes, as there are only two carbon sites compared to nine boron sites. By harnessing the well-defined three-dimensional structures of enzymes, the methods described herein can provide selectively functionalize carboranes with site specificity readily modified via directed evolution.

The organoboron products and reagents described herein can be further substituted. A compound according to Formula I, Formula III, or Formula IV may contain, for example, an optionally substituted $R^1$ group or an optionally substituted $R^2$ group, while a compound according to Formula II, Formula III, or Formula IV may contain an optionally substituted $R^3$ group, one or more optionally substituted $R^4$ groups, an optionally substituted $R^5$ group, an optionally substituted $R^6$ group, one or more optionally substituted $R^7$ groups, one or more optionally substituted $R^8$ groups, and/or one or more optionally substituted $R^9$ groups. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure is substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In general, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group.

Suitable monovalent substituents on a substitutable carbon atom of an "optionally substituted" group are independently halogen; $-(CH_2)_{0-4}R^\alpha$; $-(CH_2)_{0-4}OR^\alpha$; $-O(CH_2)_{0-4}R^\alpha$, $-O-(CH_2)_{0-4}C(O)OR^\alpha$; $-(CH_2)_{0-4}CH(OR^\alpha)_2$; $-(CH_2)_{0-4}SR^\alpha$; $-(CH_2)_{0-4}Ph$, wherein Ph is phenyl which may be substituted with $R^\alpha$; $-(CH_2)_{0-4}O(CH_2)_{0-1}$phenyl, which phenyl may be substituted with $R^\alpha$; $-CH=CHPh$, wherein Ph is phenyl which may be substituted with $R^\alpha$; $-(CH_2)_{0-4}O(CH_2)_{0-1}$-Py, wherein Py is pyridyl which may be substituted with $R^\alpha$; $-NO_2$; $-CN$; $-N_3$; $-(CH_2)_{0-4}N(R^\alpha)_2$; $-(CH_2)_{0-4}N(R^\alpha)C(O)R^\alpha$; $-N(R^\alpha)C(S)R^\alpha$; $-(CH_2)_{0-4}N(R^\alpha)C(O)NR^\alpha_2$; $-N(R^\alpha)C(S)NR^\alpha_2$; $-(CH_2)_{0-4}N(R^\alpha)C(O)OR^\alpha$; $-N(R^\alpha)N(R^\alpha)C(O)R^\alpha$; $-N(R^\alpha)N(R^\alpha)C(O)NR^\alpha_2$; $-N(R^\alpha)N(R^\alpha)C(O)OR^\alpha$; $-(CH_2)_{0-4}C(O)R^\alpha$; $-C(S)R^\alpha$; $-(CH_2)_{0-4}C(O)OR^\alpha$; $-(CH_2)_{0-4}C(O)SR^\alpha$; $-(CH_2)_{0-4}C(O)OSiR^\alpha_3$; $-(CH_2)_{0-4}OC(O)R^\alpha$; $-OC(O)(CH_2)_{0-4}SR-SC(S)SR^\alpha$; $-(CH_2)_{0-4}SC(O)R^\alpha$; $-(CH_2)_{0-4}C(O)NR^\alpha_2$; $-C(S)NR^\alpha_2$; $-C(S)SR^\alpha$; $-SC(S)SR^\alpha$, $-(CH_2)_{0-4}OC(O)NR^\alpha_2$; $-C(O)N(OR^\alpha)R^\alpha$; $-C(O)C(O)R^\alpha$; $-C(O)CH_2C(O)R^\alpha$; $-C(NOR^\alpha)R^\alpha$; $-(CH_2)_{0-4}SR^\alpha$; $-(CH_2)_{0-4}S(O)_2R^\alpha$; $-(CH_2)_{0-4}S(O)_2OR^\alpha$; $-(CH_2)_{0-4}OS(O)_2R^\alpha$; $-S(O)_2NR^\alpha_2$; $-(CH_2)_{0-4}S(O)R^\alpha$; $-N(R^\alpha)S(O)_2NR^\alpha_2$; $-N(R^\alpha)S(O)_2R^\alpha$; $-N(OR^\alpha)R^\alpha$; $-C(NH)NR^\alpha_2$; $-P(O)_2R^\alpha$; $-P(O)R^\alpha_2$; $-OP(O)R^\alpha_2$; $-OP(O)(OR^\alpha)_2$; $SiR^\alpha_3$; $-(C_{1-4}$ straight or branched)alkylene)-O$-N(R^\alpha)_2$; or $-(C_{1-4}$ straight or branched)alkylene)C(O)O$-N(R^\alpha)_2$. Each $R^\alpha$ is independently hydrogen; $C_{1-6}$ alkyl; $-CH_2Ph$, $-O(CH_2)_{0-1}Ph$; $-CH_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Suitable monovalent substituents on $R^\alpha$ are independently halogen, $-(CH_2)_{0-2}R^\beta$; $-(CH_2)_{0-2}OH$; $-(CH_2)_{0-2}OR^\beta$; $-(CH_2)_{0-2}CH(OR^\beta)_2$; $-CN$; $-N_3$; $-(CH_2)_{0-2}C(O)R^\beta$; $-(CH_2)_{0-2}C(O)OH$; $-(CH_2)_{0-2}C(O)OR^\beta$; $-(CH_2)_{0-2}SR^\beta$; $-(CH_2)_{0-2}SH$; $-(CH_2)_{0-2}NH_2$, $-(CH_2)_{0-2}NHR^\beta$; $-(CH_2)_{0-2}NR^\beta_2$; $-NO_2$; $SiR^\beta_3$; $-OSiR^\beta_3$; $-C(O)SR^\beta$; $-(C_{1-4}$ straight or branched alkylene)-C(O)OR$^\beta$; or $-SSR^\beta$; wherein each $R^\beta$ is independently selected from $C_{1-4}$ alkyl; $-CH_2Ph$; $-O(CH_2)_{0-1}Ph$; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include $=O$ and $=S$.

Suitable divalent substituents on a saturated carbon atom of an "optionally substituted" group include the following: $=O$; $=S$; $=NNR^\gamma_2$; $=NNHC(O)R^\gamma$; $=NNHC(O)OR^\gamma$; $=NNHS(O)_2R^\gamma$; $=NR^\gamma$; $=NOR^\gamma$; $-O(C(RY_2))_{2-3}O-$; or $-S(C(R^\gamma_2))_{2-3}S-$; wherein each independent occurrence of $R^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: $-O(CR^\beta 2)_{2-3}O-$; wherein each independent occurrence of $R^\beta$ is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\gamma$ include halogen; $-R^\delta$; $-OH$; $-OR^\delta$; $-CN$; $-C(O)OH$; $-C(O)OR^\delta$; $-NH_2$; $-NHR^\delta$; $-NR^\delta_2$; or $-NO_2$; wherein each $R^\delta$ is independently $C_{1-4}$ alkyl; $-CH_2Ph$; $-O(CH_2)_{0-1}Ph$; 4- to 10-membered heterocyclyl; or 6- to 10-membered heteroaryl.

Suitable substituents on a substitutable nitrogen of an "optionally substituted" group include $-R^\varepsilon$; $-NR^\varepsilon_2$; $-C(O)R^\varepsilon$; $-C(O)OR^\varepsilon$; $-C(O)C(O)R^\varepsilon$; $-C(O)CH_2C(O)R^\varepsilon$; $-S(O)_2R^\varepsilon$; $-S(O)_2NR^\varepsilon_2$; $-C(S)NR^\varepsilon_2$; $-C(NH)NR^\varepsilon_2$; or $-N(R^\varepsilon)S(O)_2R^\varepsilon$; wherein each $R^\varepsilon$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\varepsilon$ are independently halogen; $-R^\delta$; $-OH$; $-OR^\delta$; $-CN$; $-C(O)OH$; $-C(O)OR^\delta$; $-NH_2$; $-NHR^\delta$; $-NR^\delta_2$; or $-NO_2$; wherein each $R^\delta$ is independently $C_{1-4}$ alkyl; $-CH_2Ph$; $-O(CH_2)_{0-1}Ph$; $C_{6-10}$ aryl; 4- to 10-membered heterocyclyl; or 6- to 10-membered heteroaryl.

C. Reaction Conditions

The methods of the invention include forming reaction mixtures that comprise a boron-containing reagent, a carbene precursor, and a heme protein, fragment thereof, homolog thereof, or variant thereof as described above. In some embodiments, the method is carried out in vitro. In other embodiments, the heme protein is localized within a whole cell and the method is carried out in vivo. In some embodiments, the heme protein is expressed in a bacterial, archaeal, yeast or fungal host organism. In some embodiments, the method is carried out under anaerobic conditions. In other embodiments, the process is carried out under aerobic conditions.

The heme proteins, fragments thereof, homologs thereof, or variants thereof can be, for example, purified prior to addition to a reaction mixture or secreted by a cell present in the reaction mixture. The reaction mixture can contain a cell lysate including the heme protein, fragment thereof, homolog thereof, or variant thereof, as well as other proteins and other cellular materials. Alternatively, a heme protein, fragment thereof, homolog thereof, or variant thereof can catalyze the reaction within a cell expressing the heme protein, fragment thereof, homolog thereof, or variant thereof. Any suitable amount of heme protein, fragment thereof, homolog thereof, or variant thereof can be used in the methods of the invention. In general, boron-hydrogen carbene insertion reaction mixtures contain from about 0.01 mol % to about 10 mol % heme protein with respect to the carbene precursor (e.g., diazo reagent) and/or boron-containing reagent. The reaction mixtures can contain, for example, from about 0.01 mol % to about 0.1 mol % heme protein, or from about 0.1 mol % to about 1 mol % heme protein, or from about 1 mol % to about 10 mol % heme protein. The reaction mixtures can contain from about 0.05 mol % to about 5 mol % heme protein, or from about 0.05 mol % to about 0.5 mol % heme protein. The reaction mixtures can contain about 0.1, 0.2, 0.3, 0.4, 0.5, 0.6, 0.7, 0.8, 0.9, or about 1 mol % heme protein.

The concentration of boron-containing reagent and carbene precursor (e.g., diazo reagent) are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of boron-containing reagent or carbene precursor can be, for example, about 100, 200, 300, 400, 500, 600, 700, 800, or 900 µM. The concentration of boron-containing reagent or carbene precursor can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guanadinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of an organoboron product. The reactions can be conducted at any suitable temperature. In general, the reactions are conducted at a temperature of from about 4° C. to about 40° C. The reactions can be conducted, for example, at about 25° C. or about 37° C. The heme proteins or cells expressing or containing the heme proteins can be heat treated. In some embodiments, heat treatment occurs at a temperature of about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the carbene insertion into boron-hydrogen bonds occurs in the aqueous phase. In some embodiments, the heme protein, fragment thereof, variant thereof, or homolog thereof, is located in the aqueous layer whereas the substrates and/or products occur in an organic layer. Other reaction conditions may be employed in the methods of the invention, depending on the identity of a particular heme protein, boron-containing reagent, or carbene precursor (e.g., diazo reagent).

Reactions can be conducted in vivo with intact cells expressing a heme enzyme of the invention. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Organoboron product yields from reactions in vivo can be controlled, in part, by controlling the cell density in the reaction mixtures. Cellular suspensions exhibiting optical densities ranging from about 0.1 to about 50 at 600 nm can be used for boron-hydrogen carbene insertion reactions. Other densities can be useful, depending on the cell type, specific heme proteins, or other factors.

The methods of the invention can be assessed in terms of the diastereoselectivity and/or enantioselectivity of carbene insertion into boron-hydrogen bonds—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods of the invention include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments of the invention provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

IV. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1: Identifying Biocatalysts for C—B Bond Formation to Yield Compounds of Formula III by Screening a 96-Well Plate Containing Various Hemeproteins Hemeprotein Expression in 96-Well Plate Single colonies were picked with toothpicks from LBamp/chlor agar plates, and grown in deep-well (2 ml) 96-well plates containing LBamp/chlor (400 µL) at 37° C., 250 rpm shaking, and 80% relative humidity overnight. After 16 hours, 30 µL aliquots of these overnight cultures were transferred to deep-well 96-well plates containing HBamp/chlor (1 ml) using a 12-channel EDP3-Plus 5-50 µL pipette (Rainin). Glycerol stocks of the libraries were prepared by mixing cells in LBamp/chlor (100 µL) with 50% v/v glycerol (100 µL). Glycerol stocks were stored at −78° C. in 96-well microplates. Growth plates were allowed to shake for 3 hours at 37° C., 250 rpm shaking, and 80% relative humidity. The plates were then placed on ice for 30 min. Cultures were induced by adding 10 µL of a solution, prepared in sterile deionized water containing isopropyl β-D-1-thiogalactopyranoside (IPTG) and ALA. The following concentrations of IPTG and ALA are used: 2 mM IPTG and 20 mM ALA for cytochrome c proteins and 50 mM IPTG and 100 mM ALA for cytochrome P450 variants, globins and nitric oxide dioxygenases. The incubator temperature was reduced to 20° C., and the induced cultures were allowed to shake for 20 hours (250 rpm, no humidity control). Cells were pelleted (4,000×g, 5 min, 4° C.) and resuspended in 380 µL M9-N buffer.

Screening for Borylation Reactivity of Various Heme Proteins with Small-Scale Whole Cell Reactions in 96-Well Plate Plates containing cells suspended in 380 µL M9-N buffer were transferred to an anaerobic chamber and were added 1,3-dimethylimidazol-2-ylidene borane (10 µL per well, 400 mM in MeCN) and ethyl 2-diazopropanoate (abbr. Me-EDA) (10 µL per well, 400 mM in MeCN). The plates were sealed with aluminum sealing tape and shaken in the anaerobic chamber at 480 rpm for 6 h. After quenching with cyclohexane (0.6 ml), internal standard was added (20 µL of 20 mM acetophenone in cyclohexane) and the reaction mixtures were pipetted up and down to thoroughly mix the organic and aqueous layers. The plates were centrifuged (4,000×g, 5 min) and the organic layer (400 µL) was analyzed by gas chromatography (GC), gas chromatography-mass spectrometry (GCMS), supercritical fluid chromatography (SFC) or normal-phase high performance liquid chromatography (HPLC) for determination of yields and enantioselectivities.

The results of the screening are presented below and demonstrate that a variety of heme proteins and variants thereof are capable of catalyzing the formation of carbon-boron bond to give product of Formula III with varied yields and enantioselectivities. Specifically, wild-type cytochrome c from *Rhodothermus marinus* (Rma cyt c WT) can catalyzed the desired reaction with 42% yield and 72% ee. Furthermore, the opposite enantioselectivity was observed for reactions catalyzed by nitric oxide dioxygenase from *Rhodothermus marinus* (Rma NOD) and its variants as well as a truncated globin from *Bacillus subtilis* (BS).

Example 2: Enzymatic C—B Bond Formation to Yield Compounds of Formula III Using Rma Cyt c Variants In Vitro and In Vivo Cytochrome c Expression.

One liter Hyperbroth (100 µg/ml ampicillin, 20 µg/ml chloramphenicol) was inoculated with an overnight culture of 20 ml LB (100 µg/ml ampicillin, 20 µg/ml chloramphenicol). The overnight culture contained recombinant *E. coli* BL21-DE3 cells harboring a pET22 plasmid and pEC86 plasmid, encoding the cytochrome c variant under the control of the T7 promoter, and the cytochrome c maturation (ccm) operon under the control of a tet promoter, respectively. The cultures were shaken at 200 rpm at 37° C. for approximately 2 h or until an optical of density of 0.6-0.9 was reached. The flask containing the cells was placed on ice for 30 min. The incubator temperature was reduced to 20° C., maintaining the 200 rpm shake rate. Cultures were induced by adding IPTG and aminolevulinic acid (ALA) to a final concentration of 20 μM and 200 μM respectively. The cultures were allowed to continue for another 20-24 hours at this temperature and shake rate. Cells were harvested by centrifugation (4° C., 15 min, 3,000×g) to produce a cell pellet.

Preparation of Whole Cell and Heat-Treated Lysate Catalysts.

To prepare whole cells for catalysis, the cell pellet prepared in the previous paragraph was resuspended in M9-N minimal medium (M9 medium without ammonium chloride) to an optical density ($OO_{600}$) of 60. To prepare heat-treated lysate for catalysis, whole cells in M9-N minimal medium at $OO_{600}$=15 were placed in a water bath at 75° C. for 10 minutes. After the time at 75° C., the sample was centrifuged to remove the precipitate (4° C., 10 min, 4,000× g). The supernatant was collected and used as the heat-treated lysate catalyst, while the pellet was discarded.

Purification of Rma Cyt c.

To prepare purified proteins, the cell pellet prepared as described above was stored at −20° C. or below overnight. For the purification of 6×His tagged cytochrome c proteins, the thawed cell pellet was resuspended in Ni-NTA buffer A (25 mM Tris.HCl, 200 mM NaCl, 25 mM imidazole, pH 8.0, 4 ml/gcw) and lysed by sonication (2 min, 2 s pulse, 2 s off, 50% amplitude on a 0500 Qsonica sonicator). After sonication, the sample was centrifuged at 27,000×g for 10 min at 4° C. to remove cell debris. The sample was then placed in a water bath at 75° C. for 10 minutes, and centrifuged at 27,000×g for 10 min at 4° C. to remove cell debris. The collected supernatant was purified using an AKTA purifier 10 FPLC with a Ni Sepharose column (HisTrap-HP, GE healthcare, Piscataway, N.J.). The cytochrome c was eluted from the Ni Sepharose column using 25 mM Tris.HCl, 200 mM NaCl, 300 mM imidazole, pH 8.0. The Ni-purified protein was buffer exchanged into 0.1 M phosphate buffer (pH 8.0) using a 10 kDa molecular weight cut-off centrifugal filter, then dialyzed overnight at 4° C. in 20 mM phosphate buffer (pH 8.0) using a 3.5 kDa molecular weight cut-off dialysis bag. Protein concentrations were determined by BCA assay, using BSA to create the standard curve. For storage, proteins were portioned into 300 μl aliquots and stored at −80° C.

Small-Scale C—B Bond Forming Reactions in Heat-Treated Lysate Under Anaerobic Conditions.

Small-scale (400 μl) reactions were carried out in 2 ml glass crimp vials (Agilent Technologies, San Diego, Calif.). Heat-treated lysate (340 μl) was added to an unsealed crimp vial before crimp sealing with a silicone septum. The headspace of the vial was flushed with argon for 10 min (no bubbling). A solution of sodium dithionite (40 μl, 100 mM) was added, followed by a solution of boron reagent of formula I (10 μl, 400 mM in MeCN; for example, 1,3-dimethylimidazol-2-ylidene borane) and a solution of diazo reagent of formula II (10 μl, 400 mM in MeCN; for example, ethyl 2-diazopropanoate or Me-EDA). The reaction vial was left to shake on a plate shaker at 400 rpm for 6 h at room temperature. To quench the reaction, the vial was uncapped and a 1:1 mixture of ethylacetate/cyclohexane (0.6 ml) was added, followed by 1,2,3-trimethoxybenzene (20 μl, 20 mM in toluene) as an internal standard. The mixture was transferred to a 1.5 ml Eppendorf tube and vortexed and centrifuged (14000× ref, 5 min). The organic layer was analyzed by gas chromatography (GC), gas chromatography-mass spectrometry (GCMS), supercritical fluid chromatography (SFC) or normal-phase high performance liquid chromatography (HPLC).

Figure 2:
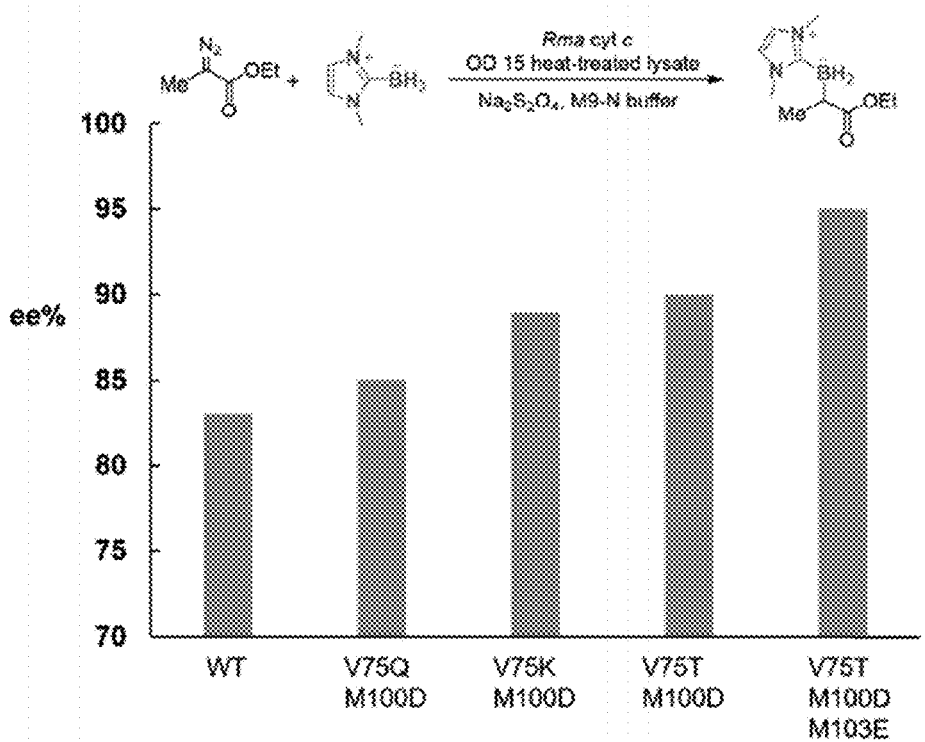
FIG. 2 shows the formation of carbon-boron bonds by cytochrome c and variants thereof.

The results of the small scale reactions are presented in FIG. 2 and demonstrate that Rma cyt c and variants thereof are capable of catalyzing the formation of carbon-boron bond to give product of Formula III with high selectivity. Specifically, the best variant found in the initial screen of Rma cyt c variants encoded the mutations V75T, M100D and M103E, which catalyzed the desired reaction with >95% ee. This can be improved by further engineering, if desired.

Small-Scale Whole Cell Catalysis of Carbon-Boron Bond Formation.

Small-scale (400 μl) reactions were carried out in 2 ml glass crimp vials (Agilent Technologies, San Diego, Calif.). Whole cell catalysts (380 $OD_{600}$=15 in M9-N minimal medium) were added to an unsealed crimp vial before crimp sealing with a silicone septum. The headspace of the vial was flushed with argon for 10 min (no bubbling). A solution of borane reagent of formula I (10 μl, 400 mM in MeCN; for example, 1,3-dimethylimidazol-2-ylidene borane) and a solution of diazo reagent of formula II (10 μl, 400 mM in MeCN; for example, ethyl 2-diazopropanoate or Me-EDA). The reaction vial was left to shake on a plate shaker at 400 rpm for 6 h at room temperature. To quench the reaction, the vial was uncapped and a 1:1 mixture of ethylacetate/cyclohexane (0.6 ml) was added, followed by 1,2,3-trimethoxybenzene (20 μl, 20 mM in toluene) as an internal standard. The mixture was transferred to a 1.5 ml Eppendorf tube and vortexed and centrifuged (14000× ref, 5 min). The organic layer was analyzed by gas chromatography (GC), gas chromatography-mass spectrometry (GCMS), supercritical fluid chromatography (SFC) or normal-phase high performance liquid chromatography (HPLC).

Figure 3:
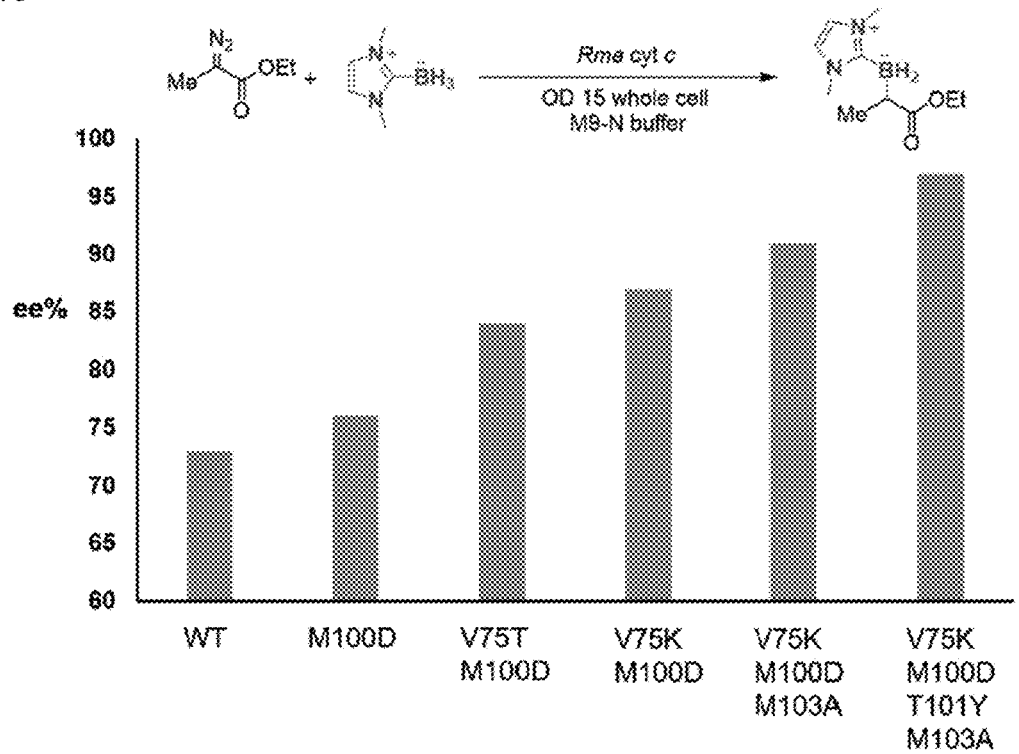
FIG. 3 shows the use of cytochrome c in whole cell catalysts for organoboron product formation.

The results of the small scale reactions are presented in FIG. 3 and demonstrate that Rma cyt c and variants thereof function as whole cell catalysts and promote the formation of carbon-boron bond to give products of Formula III with high selectivity. Specifically, the best variant found in the initial screen of Rma cyt c variants encoded the mutations, which provided products of Formula III in >97% ee. The catalytic performance of these heme proteins can be improved by further engineering, if desired.

Example 3: Enzymatic Carbon-Boron Bond Formation to Yield Compounds of Formula III Using Globins and Nitric Oxide Dioxygenase (NOD)

Globin Expression and Purification.

One liter Hyperbroth (0.1 mg/ml ampicillin) was inoculated with an overnight culture (25 ml LB, 0.1 mg/ml ampicillin) of recombinant *E. coli* BL21 cells harboring a pCWori or pET22 plasmid encoding the globin variants or nitric oxide dioxygenase (NOD) variants under the control of the tac promoter. The cultures were shaken at 200 rpm at 37° C. for approximately 2 h or until an optical of density of 0.6-0.9 was reached. The flask containing the cells was placed on ice for 30 min. Then the cultures were induced by adding IPTG and aminolevulinic acid (ALA) to a final concentration of 0.25 mM and 0.5 mM respectively. The temperature was reduced to 20° C. and the shake rate was reduced to 130-150 rpm for 20 min The cultures were allowed to continue for another 20-24 hours at this temperature and shake rate. Cells were harvested by centrifugation (4° C., 15 min, 3,000×g) to produce a cell pellet. To prepare whole cells for catalysis, the cell pellet prepared above was resuspended in M9-N minimal medium (M9 medium without ammonium chloride) to an optical density (OD600) of 15.

Small-Scale Whole Cell Catalysis of Carbon-Boron Bond Formation.

Small-scale (400 µl) reactions were carried out in 2 ml glass crimp vials (Agilent Technologies, San Diego, Calif.). Whole cell catalysts (380 µl, $OD_{600}$=15 in M9-N minimal medium) were added to an unsealed crimp vial before crimp sealing with a silicone septum. The headspace of the vial was flushed with argon for 10 min (no bubbling). A solution of borane reagent of formula I (10 µl, 400 mM in MeCN; for example, 1,3-dimethylimidazol-2-ylidene borane) and a solution of diazo reagent of formula II (10 µl, 400 mM in MeCN; for example, ethyl 2-diazopropanoate or Me-EDA). The reaction vial was left to shake on a plate shaker at 400 rpm for 6 h at room temperature. To quench the reaction, the vial was uncapped and a 1:1 mixture of ethylacetate/cyclohexane (0.6 ml) was added, followed by 1,2,3-trimethoxybenzene (20 µl, 20 mM in toluene) as an internal standard. The mixture was transferred to a 1.5 ml Eppendorf tube and vortexed and centrifuged (14000× ref, 5 min). The organic layer was analyzed by gas chromatography (GC), gas chromatography-mass spectrometry (GCMS), supercritical fluid chromatography (SFC) or normal-phase high performance liquid chromatography (HPLC).

Figure 4:
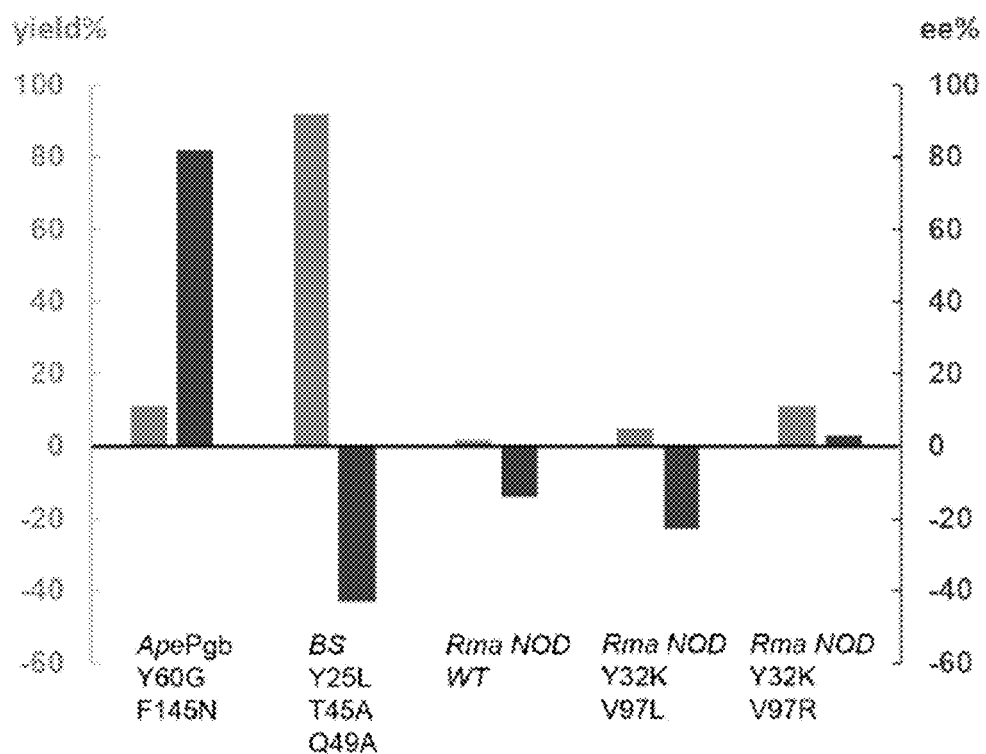
FIG. 4 shows the formation of carbon-boron bonds by nitric oxide dioxygenase, globins, and variants thereof.

The results of the small scale reactions are presented in FIG. 4 and demonstrate that several globins, nitric oxide dioxygenase (NOD) and variants thereof function as whole cell catalysts and promote the formation of carbon-boron bond to give product of Formula III. A variant of truncated hemoglobin from *Bacillus subtilis* (BS) exhibited a high yield (92%). Furthermore, enantioselectivity opposite to those obtained with Rma cyt c variants were obtained with BS Y251 T45A Q49A (−43%) and several Rma NOD variants. The catalytic performance of these heme proteins can be improved by further engineering, if desired.

Example 4: Enzymatic Carbon-Boron Bond Formation to Yield Compounds of Formula III Using P450s P450 Expression.

One liter Hyperbroth (0.1 mg/ml ampicillin) was inoculated with an overnight culture (25 ml LB, 0.1 mg/ml ampicillin) of recombinant *E. coli* BL21 cells harboring a pCWori or pET22 plasmid encoding the P450 variant under the control of the tac promoter. The cultures were shaken at 200 rpm at 37° C. for roughly 3.5 h or until an optical of density of 1.2-1.8 was reached. The temperature was reduced to 20° C. and the shake rate was reduced to 130-150 rpm for 20 min, then the cultures were induced by adding IPTG and aminolevulinic acid to a final concentration of 0.25 mM and 0.5 mM, respectively. The cultures were allowed to continue for another 20 hours at this temperature and shake rate. Cell were harvested by centrifugation (4° C., 15 min, 3,000×g) to produce a cell pellet. To prepare whole cells for catalysis, the cell pellet prepared above was resuspended in M9-N minimal medium (M9 medium without ammonium chloride) to an optical density (00500) of 15.

Small-Scale Whole Cell Catalysis of Carbon-Boron Bond Formation.

Small-scale (400 µL) reactions were carried out in 2 ml glass crimp vials (Agilent Technologies, San Diego, Calif.). Whole cell catalysts (380 µL, $OD_{600}$=15 in M9-N minimal medium) were added to an unsealed crimp vial before crimp sealing with a silicone septum. The headspace of the vial was flushed with argon for 10 min (no bubbling). A solution of borane reagent of formula I (10 µl, 400 mM in MeCN; for example, 1,3-dimethylimidazol-2-ylidene borane) and a solution of diazo reagent of formula II (10 µl, 400 mM in MeCN; for example, ethyl 2-diazopropanoate or Me-EDA). The reaction vial was left to shake on a plate shaker at 400 rpm for 6 h at room temperature. To quench the reaction, the vial was uncapped and a 1:1 mixture of ethylacetate/cyclohexane (0.6 ml) was added, followed by 1,2,3-trimethoxybenzene (20 µl, 20 mM in toluene) as an internal standard. The mixture was transferred to a 1.5 ml Eppendorf tube and vortexed and centrifuged (14000× ref, 5 min). The organic layer was analyzed by gas chromatography (GC), gas chromatography-mass spectrometry (GCMS), supercritical fluid chromatography (SFC) or normal-phase high performance liquid chromatography (HPLC).

Figure 5:
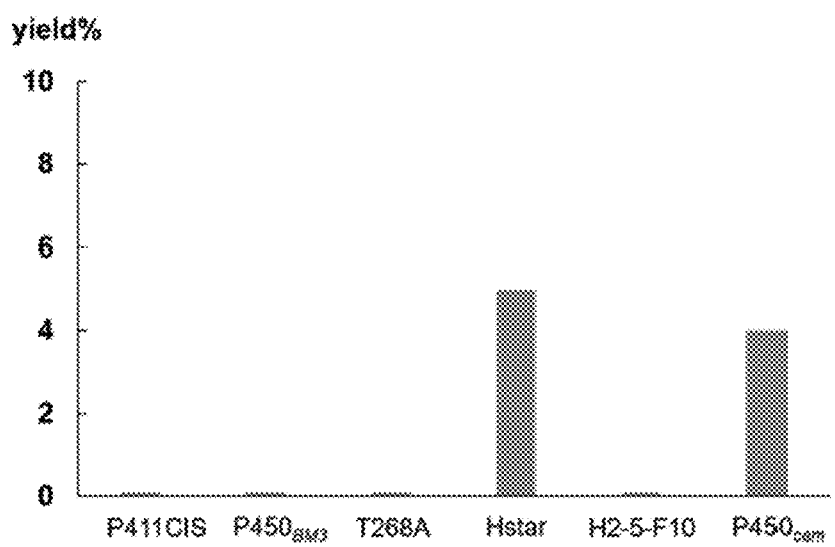
FIG. 5 shows the formation of carbon-boron bonds by cytochrome P450 and variants thereof.

The results of the small scale reactions are presented in FIG. 5 and demonstrate that Rma cyt c and variants thereof function as whole cell catalysts and promote the formation of carbon-boron bond to give product of formula 111. Although yields are currently low (<5%), catalytic performance of these heme proteins can be improved by further engineering, if desired.

Small-scale carbon-boron bond forming reactions under aerobic conditions. The procedures for carbon-boron bond formation under aerobic conditions are similar to that described for anaerobic conditions, except that the reactions are carried out under air. Products of Formula III are obtained in reduced yield compared to the anaerobic reactions, but this can be improved by further protein engineering, if desired.

Example 5: Biological Organoborane Production with *R. marinus* Cytochrome c

Figure 6B:
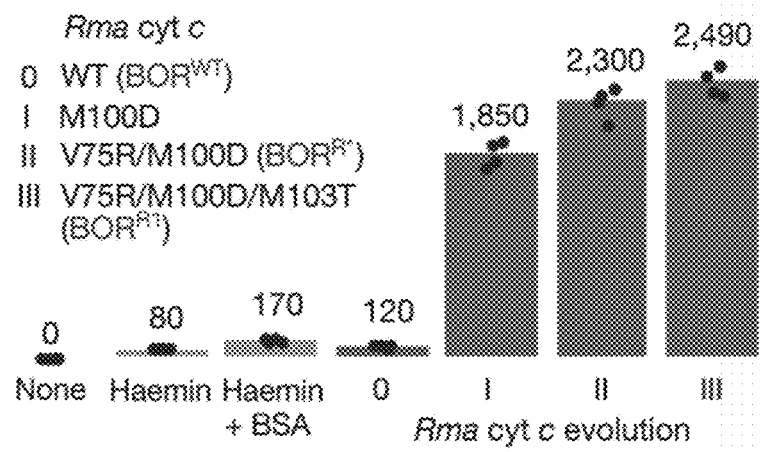
FIG. 6B shows that sequential site-saturation mutagenesis of whole-cell Rma cyt c targeting active-site amino acid residues M100, V75 and M103 improved the turnover of the bacterial production of organoborane 3. Whole-cell Rma cyt c variants were compared using *E. coli* cells at concentration $OD_{600}$=15. Total turnover numbers (TTNs) were calculated with respect to the concentration of Rma cyt c expressed in *E. coli* and represent the total number of turnovers obtained from the catalyst under the stated reaction conditions. Single-letter abbreviations for the amino acid residues are as follows: D, Asp; M, Met; R, Arg; T, Thr; and V, Val.
Figure 6C:
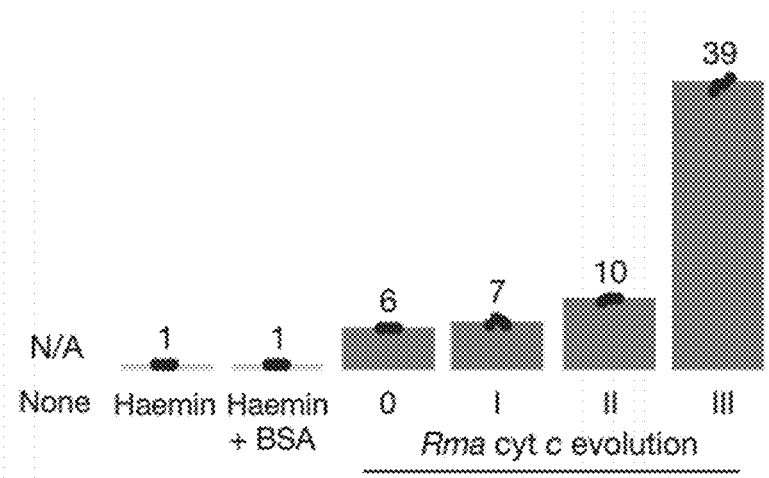
FIG. 6C shows that sequential site-saturation mutagenesis of whole-cell Rma cyt c targeting active-site amino acid residues M100, V75 and M103 improved the enantioselectivity of the bacterial production of organoborane 3. Whole-cell Rma cyt c variants were compared using *E. coli* cells at concentration $OD_{600}$=15.

We first set out to assess whether biological organoborane production might be feasible in a bacterial cell. When *E. coli* BL21(DE3) cells harbouring wild-type cytochrome c from *Rhodothermus marinus*, a Gram-negative, thermohalophilic bacterium from submarine hot springs in Iceland[8] (Rma cyt c), were incubated with N-heterocyclic carbene borane[22,23] (NHC-borane) 1 and ethyl 2-diazopropanoate (Me-EDA) 2 in neutral buffer (M9-N minimal medium, pH 7.4) at room temperature, in vivo production of organoborane 3 was observed, with 120 turnovers (calculated with respect to the concentration of Rma cyt c expressed in *E. coli*; FIG. 6A, FIG. 6B) and an e.r. of 85:15 (R/S isomer=6; FIG. 6C). Since the pET22b/pEC86 expression system translocates Rma cyt c to the *E. coli* periplasm for post-translational maturation (during which the heme cofactor is covalently ligated to the cyt c apoprotein)[24], we assumed that borylation takes places in the periplasmic compartment. In the absence of Rma cyt c, *E. coli* yielded only a trace amount of borylation product with very low stereoselectivity Table 2). Both substrates and the organoborane product were stable under these conditions. The heme cofactor alone could also promote the borylation reaction, although with no stereoselectivity. Other cytochrome c proteins, cytochromes P450, and globins also demonstrated carbon-boron bond forming ability, but their selectivities were unsatisfactory (Table 2).

TABLE 2

Preliminary experiments with heme and heme proteins.

NHC-borane (1) + Me-EDA (2) →[catalyst, M9-N buffer (pH 7.4), room temperature] 3

| Catalyst | TTN | e.r. |
|---|---|---|
| Controls | | |
| None | 0 | N/A |
| hemin | 80 ± 5 | 0 |
| hemin + BSA | 170 ± 10 | 54:46 |
| E. coli cell background | Trace | 55:45 |
| Cytochromes c | | |
| R. marinus cyt c | 120 ± 20 | 85:15 |
| H. thermophilus cyt c | 140 ± 10 | 55:45 |
| Globin | | |
| P. ferrireducens proglobin Y60V | NR | — |
| P450s | | |
| P411 CIS (12) | trace | n.d. |
| BM3 wild-type | NR | — |
| BM3 Hstar (13) | trace | n.d. |

N/A—not applicable;
NR—no product was detected;
n.d.—not determined

Unless otherwise noted, all chemicals and reagents were obtained from commercial suppliers (Sigma-Aldrich, VWR, Alfa Aesar, Acros) and used without further purification. Bovine serum albumin (BSA) was purchased from Sigma-Aldrich. Silica gel chromatography was carried out using AMD Silica Gel 60, 230-400 mesh. $^1$H and $^{13}$C NMR spectra were recorded on a Bruker Prodigy 400 MHz instrument (400 MHz for $^1$H and 100 MHz for $^{13}$C). Chemical shifts (δ) are reported in ppm downfield from tetramethylsilane, using the solvent resonance as the internal standard ($^1$H NMR: δ=7.26, $^{13}$C NMR: δ=77.36 for CDCl$_3$). $^{19}$F NMR and $^{11}$B NMR data were collected on a VARIAN 300 MHz spectrometer (101 MHz for $^{19}$F NMR) and a Bruker Prodigy 400 MHz instrument (128 MHz for $^{11}$B NMR), respectively. Sonication was performed using a Qsonica Q500 sonicator. High-resolution mass spectra were obtained at the California Institute of Technology Mass Spectral Facility. Chemical reactions were monitored using thin layer chromatography (Merck 60 gel plates) using a UV-lamp for visualization. Gas chromatography (GC) analyses were carried out using a Shimadzu GC-17A gas chromatograph, a FID detector, and J&W HP-5 column (30 m×0.32 mm, 0.25 μm film). Gas chromatography-mass spectrometry (GC-MS) analyses were carried out using Shimadzu GCMS-QP2010SE system and J&W HP-5 ms column. Analytical chiral supercritical fluid chromatography (SFC) was performed with a JACSO 2000 series instrument using i-PrOH and supercritical CO$_2$ as the mobile phase. Chiral normal-phase HPLC analyses were performed using an Agilent 1200 series instrument with i-PrOH and hexanes as the mobile phase. Chiral GC was performed on an Agilent 6850 GC with FID detector using a Chiraldex GTA column (30.0 m×0.25 mm) at 1.0 mL/min He carrier gas flow.

Plasmid pET22b(+) was used as a cloning vector, and cloning was performed using Gibson assembly[25]. The cytochrome c maturation plasmid pEC86' was used as part of a two-plasmid system to express prokaryotic cytochrome c proteins. Cells were grown using Luria-Bertani medium or HyperBroth (AthenaES) with 100 μg/mL ampicillin and 20 μg/mL chloramphenicol (LB$_{amp/chlor}$ or HB$_{amp/chlor}$). Cells without the pEC86 plasmid were grown with 100 μg/mL ampicillin (LB$_{amp}$ or HB$_{amp}$). Electrocompetent *Escherichia coli* cells were prepared following the protocol of Sambrook et al.[26]. T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM Na$_2$HPO$_4$, 22.0 mM KH$_2$PO$_4$, 8.6 mM NaCl, 2.0 mM MgSO$_4$, and 0.1 mM CaCl$_2$.

Plasmid Construction.

All variants described in this paper were cloned and expressed using the pET22b(+) vector (Novagen). The gene encoding Rma cyt c (UNIPROT ID B3FQS5) was obtained as a single gBlock (IDT), codon-optimized for *E. coli*, and cloned using Gibson assembly[25] into pET22b(+) (Novagen) between restriction sites NdeI and XhoI in frame with an N-terminal pelB leader sequence (to ensure periplasmic localization and proper maturation; MKYLLPTAAAGLLL-LAAQPAMA) and a C-terminal 6×His-tag. This plasmid was co-transformed with the cytochrome c maturation plasmid pEC86 into E. Cloni® EXPRESS BL21(DE3) cells (Lucigen).

Cytochrome c Expression and Purification.

Purified cytochrome c proteins were prepared as follows. One litre HB$_{amp/chlor}$ in a 4 L flask was inoculated with an overnight culture (20 mL, LB$_{amp/chlor}$) of recombinant E. Cloni® EXPRESS BL21(DE3) cells containing a pET22b (+) plasmid encoding the cytochrome c variant, and the pEC86 plasmid. The culture was shaken at 37° C. and 200 rpm (no humidity control) until the OD$_{600}$ was 0.7 (approximately 3 hours). The culture was placed on ice for 30 minutes, and isopropyl β-D-1-thiogalactopyranoside (IPTG) and 5-aminolevulinic acid (ALA) were added to final concentrations of 20 μM and 200 μM, respectively. The incubator temperature was reduced to 20° C., and the culture was allowed to shake for 22 hours at 200 rpm. Cells were harvested by centrifugation (4° C., 15 min, 4,000×g), and the cell pellet was stored at −20° C. until further use (at least 24 hours). The cell pellet was resuspended in buffer containing 100 mM NaCl, 20 mM imidazole, and 20 mM Tris-HCl buffer (pH 7.5 at 25° C.) and cells were lysed by sonication (2 minutes, 2 seconds on, 2 seconds off, 40% duty cycle; Qsonica Q500 sonicator). Cell debris was removed by centrifugation for 20 min (5000×g, 4° C.). Supernatant was sterile filtered through a 0.45 μm cellulose acetate filter and purified using a 1 mL Ni-NTA column (HisTrap HP, GE Healthcare, Piscataway, N.J.) using an AKTA purifier FPLC system (GE healthcare). The cytochrome c protein was eluted from the column by running a gradient from 20 to 500 mM imidazole over 10 column volumes. The purity of the collected cytochrome c fractions was analysed using sodium dodecyl sulphate-polyacrylamide gel electrophoresis (SDS-PAGE). Pure fractions were pooled and concentrated using a 3 kDa molecular weight cut-off centrifugal filter and dialyzed overnight into 0.05 M phosphate buffer (pH=7.5) using 3 kDa molecular weight cut-off dialysis tubing. The dialyzed protein was concentrated again, flash-frozen on dry ice, and stored at −20° C. The concentration of cytochrome c was determined in triplicate using the hemochrome assay described below.

Cytochrome P450 and Globin Expression and Purification.

Purified P450s and globins were prepared differently from the cytochrome c proteins, and described as follows. One litre $HB_{amp}$ in a 4 L flask was inoculated with an overnight culture (20 mL, $LB_{amp}$) of recombinant E. Cloni® EXPRESS BL21(DE3) cells containing a pET22b(+) plasmid encoding the P450 or globin variant. The culture was shaken at 37° C. and 200 rpm (no humidity control) until the $OD_{600}$ was 0.7 (approximately 3 hours). The culture was placed on ice for 30 minutes, and IPTG and ALA were added to final concentrations of 0.5 mM and 1 mM, respectively. The incubator temperature was reduced to 20° C., and the culture was allowed to shake for 20 hours at 200 rpm. Cells were harvested by centrifugation (4° C., 15 min, 4,000×g), and the cell pellet was stored at −20° C. until further use (at least 24 hours). The cell pellet was resuspended in buffer containing 100 mM NaCl, 20 mM imidazole, and 20 mM Tris-HCl buffer (pH 7.5 at 25° C.). Hemin (30 mg/mL, 0.1 M NaOH; Frontier Scientific) was added to the resuspended cells such that 1 mg of hemin was added for every 1 gram of cell pellet. Cells were lysed by sonication (2 minutes, 1 seconds on, 2 seconds off, 40% duty cycle; Qsonica Q500 sonicator). Cell debris was removed by centrifugation for 20 min (27,000×g, 4° C.). Supernatant was sterile filtered through a 0.45 µm cellulose acetate filter, and purified using a 1 mL Ni-NTA column (HisTrap HP, GE Healthcare, Piscataway, N.J.) using an AKTA purifier FPLC system (GE healthcare). The P450 and globin proteins were eluted from the column by running a gradient from 20 to 500 mM imidazole over 10 column volumes. The purity of the collected protein fractions was analysed using SDS-PAGE. Pure fractions were pooled and concentrated using a 10 kDa molecular weight cut-off centrifugal filter and buffer-exchanged with 0.1 M phosphate buffer (pH=8.0). The purified protein was flash-frozen on dry ice and stored at −20° C. P450 and globin concentrations were determined in triplicate using published extinction coefficients and the hemochrome assay described below.

Hemochrome Assay.

A solution of sodium dithionite (10 mg/mL) was prepared in M9-N buffer. Separately, a solution of 1 M NaOH (0.4 mL) was mixed with pyridine (1 mL), followed by centrifugation (10,000×g, 30 seconds) to separate the excess aqueous layer gave a pyridine-NaOH solution. To a cuvette containing 700 µL protein solution (purified protein or heat-treated lysate) in M9-N buffer, 50 µL of dithionite solution and 250 µL pyridine-NaOH solution were added. The cuvette was sealed with Parafilm, and the UV-Vis spectrum was recorded immediately. Cytochrome c concentration was determined using $\varepsilon_{550\text{-}535}$=22.1 $mM^{-1}cm^{-1}$.[27] Protein concentrations determined by the hemochrome assay were in agreement with that determined by the bicinchoninic acid (BCA) assay (Thermo Fisher) using bovine serum albumin (BSA) for standard curve preparation.

Cell Lysate Preparation.

Cell lysates were prepared as follow: E. coli cells expressing Rma cyt c variant were pelleted (4,000×g, 5 min, 4° C.), resuspended in M9-N buffer and adjusted to the appropriate $OD_{600}$. Cells were lysed by sonication (2 minutes, 1 seconds on, 2 seconds off, 40% duty cycle; Qsonica Q500 sonicator), aliquoted into 2 mL microcentrifuge tubes, and the cell debris was removed by centrifugation for 10 min (14,000×g, 4° C.). The supernatant was sterile filtered through a 0.45 µm cellulose acetate filter, and the concentration of cytochrome c protein lysate was determined using the hemochrome assay. Using this protocol, the protein concentrations we typically observed for $OD_{600}$=15 lysates are in the 8-15 µM range for wild-type Rma cyt c and 1-10 µM for other Rma cyt c variants.

Small-Scale Whole-Cell Bioconversion.

In an anaerobic chamber, NHC-borane (10 µL, 400 mM in MeCN) and diazo reagent (10 µL, 400 mM in MeCN) were added to E. coli harbouring Rma cyt c variant (380 µL, adjusted to the appropriate $OD_{600}$) in a 2 mL crimp vial. The vial was crimp-sealed, removed from the anaerobic chamber, and shaken at 500 rpm at room temperature for 6 h (24 h for reactions with Ph-EDA or $CF_3$-DMB). At the end of the reaction, the crimp vial was opened and the reaction was quenched with hexanes/ethyl acetate (4:6 v/v, 0.6 mL), followed by the addition of internal standard (20 µL of 20 mM 1,2,3-trimethoxybenzene in toluene). The reaction mixture was transferred to a microcentrifuge tube, vortexed (10 seconds, 3 times), then centrifuged (14,000×g, 5 min) to completely separate the organic and aqueous layers (the vortex-centrifugation step was repeated if complete phase separation was not achieved). The organic layer (200 µL) was removed for GC-MS and chiral SFC/HPLC analysis. All biocatalytic reactions reported were performed in replicates (duplicates to quadruplicates) from at least two biological replicates. The total turnover numbers (TTNs) reported are calculated with respect to Rma cyt c expressed in E. coli and represent the total number of turnovers obtained from the catalyst under the stated reaction conditions. For reactions using $OD_{600}$=15 E. coli cells, the catalyst loadings are 0.0001-0.0015 mol % of enzymes with respect to the limiting reagent in the reaction. The $g_{borylation\ product}/g_{dry\ cell}$ weight ratios ranged from ~0.05 (wild-type) to ~2 (engineered variant).

Preparation of Whole-Cell Suspensions for Borylation Reactions:

$HB_{amp/chlor}$ (200 mL) in a 1 L flask was inoculated with an overnight culture (4 mL, $LB_{amp/chlor}$) of recombinant E. Cloni® EXPRESS BL21(DE3) cells containing a pET22b (+) plasmid encoding Rma cyt c variant, and the pEC86 plasmid. The culture was shaken at 37° C. and 250 rpm (no humidity control) until the $OD_{600}$ was 0.7 (typically 2-3 hours). The culture was placed on ice for 30 minutes, and IPTG and ALA were added to final concentrations of 20 µM and 200 µM, respectively. The incubator temperature was reduced to 20° C., and the culture was allowed to shake for 22 hours at 140 rpm. Cells were pelleted by centrifugation (4° C., 5 min, 4,000×g), resuspended in M9-N buffer and adjusted to $OD_{600}$=30. The whole-cell suspension was placed on ice and bubbled with Ar for 30 min.

Figure 6D:
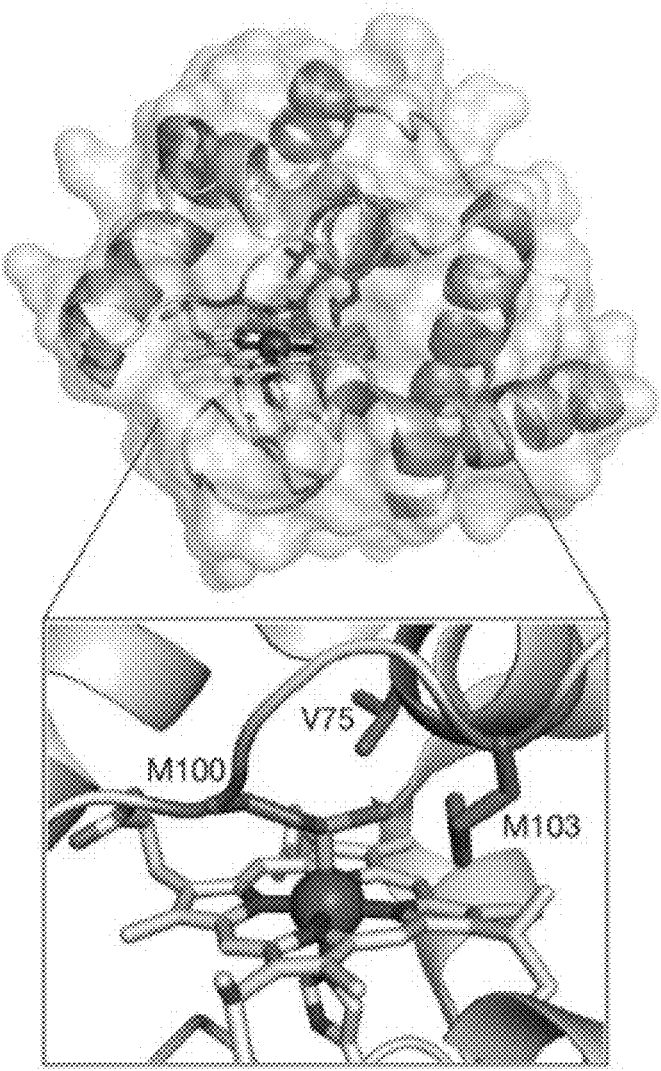
FIG. 6D shows the X-ray crystal structure of wild-type Rma cyt c (PDB: 3CP5).

Example 6: Evolution of Borylation Catalysts Via Site-Saturation Mutagenesis of R. marinus Cytochrome c To improve the performance of this whole-cell catalyst, we subjected the wild-type Rma cyt c (which we refer to as $BOR^{WT}$ hereafter) to site-saturation mutagenesis, sequentially targeting active-site amino acid residues M100, V75 and M103, which are closest to the heme iron in BOR$^{WT}$ (within 7A, FIG. 6D). Each single-site site-saturation mutagenesis library was cloned using the 22c-trick method[28], screened as whole-cell catalysts in 96-well plates for improved borylation enantioselectivity, and the best variant was used to parent the next round of mutation and screening.

Mutagenesis Library Construction.

Cytochrome c site-saturation mutagenesis libraries were generated using a modified version of the 22-codon site-saturation method[28]. For each site-saturation library, oligonucleotides were ordered such that the coding strand contained the degenerate codon NDT, VHG or TGG. The reverse complements of these primers were also ordered. The three forward primers were mixed together in a 12:9:1 ratio, (NDT:VHG:TGG) and the three reverse primers were mixed similarly. Two PCRs were performed, pairing the mixture of forward primers with a pET22b(+) internal reverse primer, and the mixture of reverse primers with a pET22b(+) internal forward primer. The two PCR products were gel purified, ligated together using Gibson assembly[25], and transformed into E. Cloni® EXPRESS BL21(DE3) cells.

Mutagenesis Library Screening in Whole Cells.

Single colonies were picked with toothpicks off of LB$_{amp/chlor}$ agar plates, and grown in deep-well (2 mL) 96-well plates containing LB$_{amp/chlor}$ (400 μL) at 37° C., 250 rpm shaking, and 80% relative humidity overnight. After 16 hours, 30 μL aliquots of these overnight cultures were transferred to deep-well 96-well plates containing HB$_{amp/chlor}$ (1 mL) using a 12-channel EDP3-Plus 5-50 μL pipette (Rainin). Glycerol stocks of the libraries were prepared by mixing cells in LB$_{amp/chlor}$ (100 μL) with 50% v/v glycerol (100 μL). Glycerol stocks were stored at −78° C. in 96-well microplates. Growth plates were allowed to shake for 3 hours at 37° C., 250 rpm shaking, and 80% relative humidity. The plates were then placed on ice for 30 min. Cultures were induced by adding 10 μL of a solution, prepared in sterile deionized water, containing 2 mM IPTG and 20 mM ALA. The incubator temperature was reduced to 20° C., and the induced cultures were allowed to shake for 20 hours (250 rpm, no humidity control). Cells were pelleted (4,000×g, 5 min, 4° C.), resuspended in 380 μL M9-N buffer, and the plates containing the cell suspensions were transferred to an anaerobic chamber. To deep-well plates of cell suspensions were added NHC-borane substrate (10 μL per well, 400 mM in MeCN) and diazo reagent (10 μL per well, 400 mM in MeCN). The plates were sealed with aluminium sealing tape, removed from the anaerobic chamber, and shaken at 500 rpm for 6 h (24 h for reactions with Ph-EDA or CF$_3$-DMB due to their lower aqueous solubility). After quenching with hexanes/ethyl acetate (4:6 v/v, 0.6 mL), internal standard was added (20 μL of 20 mM 1,2,3-trimethoxybenzene in toluene). The plates were then sealed with sealing mats and shaken vigorously to thoroughly mix the organic and aqueous layers. The plates were centrifuged (4,000×g, 5 min) and the organic layer (200 μL) was transferred to autosampler vials with vial inserts for gas chromatography-mass spectrometry (GC-MS) or chiral high performance liquid chromatography (HPLC)/supercritical fluid chromatography (SFC) analysis. Hits from library screening were confirmed by small-scale biocatalytic reactions.

With a single mutation M100D replacing the distal axial ligand, the first-generation biocatalyst exhibited 16-fold improvement in turnover over the wild-type (1850 TTN, FIG. 6B), with 88:12 e.r. (R/S isomer=7; FIG. 6C). The M100D mutation also substantially improved carbene transfer reactivity for Si—H insertion catalyzed by Rma cyt c[6]. This improvement in catalytic performance is likely due to removal of the axial ligand from the heme iron, which opens a site primed for iron carbenoid formation and subsequent product formation[29]. Two subsequent rounds of mutagenesis and screening led to variant BOR$^{R1}$ (V75R M100D M103T), which exhibited a turnover of 2490 and an e.r. of 97.5:2.5 (R/S isomer=39).

Example 7: Biocatalytic Synthesis of (1,3-dimethyl-1H-imidazol-3-ium-2-yl)(1-ethoxy-1-oxopropan-2-yl)dihydroborate The genetically programmed biological function of the biocatalysts is readily scalable from analytic to mmol scale—with 0.5 mmol substrates, BOR$^{R1}$ produced organoborane 3 in 97.5:2.5 e.r. and 75% isolated yield (3000 TTN). The absolute configuration of product 3 was unambiguously assigned to be R by X-ray crystallography.

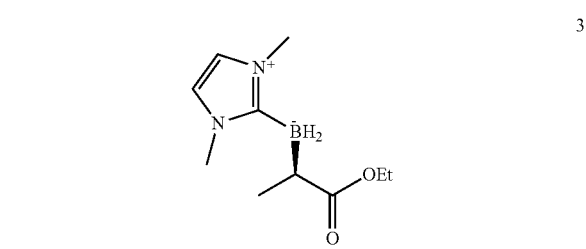

3

Under anaerobic conditions, to a 40 mL vial were added 12 mL Rma cyt c BOR$^{R1}$ whole-cell suspension (OD$_{600}$=30), 3 mL glucose solution (250 mM), diMeNHC—BH$_3$ solution (125 μL, 2 M in MeCN) and Me-EDA (125 μL, 2 M in MeCN). The vial was capped and shaken at 520 rpm in an anaerobic chamber at room temperature. After 4 hours, another portion of diMeNHC—BH$_3$ (125 μL, 2 M in MeCN) and Me-EDA (125 μL, 2 M in MeCN) were added and the vial was shaken for 8 more hours at 520 rpm. The reaction mixture was then transferred to a 50 mL Falcon tube and extracted by 30 mL 3:7 hexanes/EtOAc via vortexing (30 s for three times). Centrifugation (5,000×g, 5 min) was used to completely separate the organic and aqueous layers. After removal of the organic layers, two additional rounds of extraction were performed. The combined organic extracts were dried over anhydrous Na$_2$SO$_4$, concentrated, and purified by flash chromatography (dry loading) with EtOAc/hexanes (5% to 60% EtOAc/hexanes gradient) to afford pure organoborane product 3 (79 mg, 0.376 mmol, 75% yield). The protein concentration of OD$_{600}$=30 whole-cell solution was determined to be 10.41 μM by hemochrome assay after cell lysis by sonication. The total turnover number for this reaction was 3000. The stereoselectivity of the product was determined as 97.5:2.5 e.r. by normal-phase chiral HPLC. $[\alpha]_D^{23}$=+114.5 (c 0.19, EtOAc). $^1$H NMR (400 MHz, Chloroform-d) δ 6.82 (s, 2H), 3.98-3.78 (m, 2H), 3.75 (s, 6H), 1.95-1.10 (m, 2H), 1.88 (br s, 1H), 1.10 (d, J=6.2 Hz, 3H), 1.06 (t, J=7.1 Hz, 3H); $^{13}$C NMR (101 MHz, Chloroform-d) δ 183.5, 120.4, 58.7, 36.2, 30.5, 17.8, 14.6. The boron-bound NHC quaternary carbon was not resolved; $^{11}$B NMR (128 MHz, Chloroform-d) δ −24.55 (t, J=90 Hz).

Example 8: Study Borylation Kinetics with R. Marinus Cytochrome c Variants

With an excellent borylating bacterium in hand, the properties and potential of the system were assessed. We characterised the initial rates of in vivo borylation and found that screening for improved enantioselectivity also led to an overall rate enhancement: whole-cell $BOR^{R1}$ is 15 times faster than $BOR^{WT}$, with a turnover frequency of 6100 h$^{-1}$.

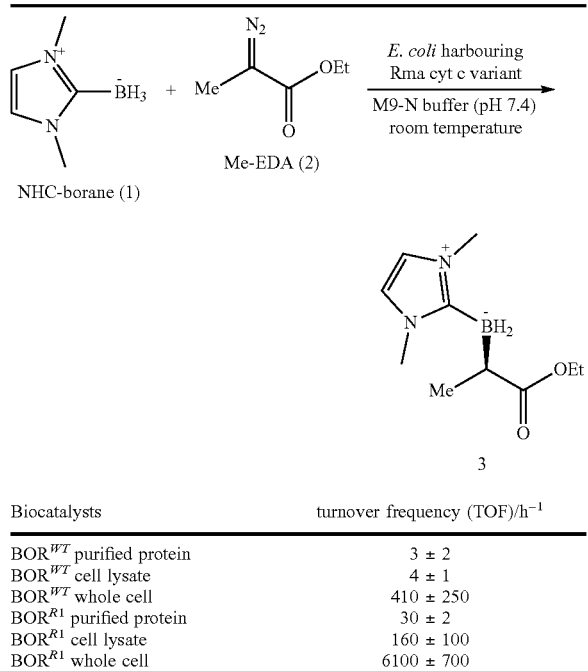

| Biocatalysts | turnover frequency (TOF)/h$^{-1}$ |
|---|---|
| $BOR^{WT}$ purified protein | 3 ± 2 |
| $BOR^{WT}$ cell lysate | 4 ± 1 |
| $BOR^{WT}$ whole cell | 410 ± 250 |
| $BOR^{R1}$ purified protein | 30 ± 2 |
| $BOR^{R1}$ cell lysate | 160 ± 100 |
| $BOR^{R1}$ whole cell | 6100 ± 700 |

TOFs reported represent mean values averaged over four experiments. Errors quoted indicate one standard deviation.

Whole cell-catalysed reaction: Experiments were performed using whole *E. coli* cells harbouring $BOR^{WT}$ or $BOR^{R1}$ (with the BOR protein concentration normalised to 10 μM), 10 mM borane, 10 mM diazo ester, 5 vol % MeCN, M9-N buffer at room temperature under anaerobic conditions for various time intervals.

Cell lysate-catalysed reaction: Experiments were performed using cell lysate of *E. coli* harbouring $BOR^{WT}$ or $BOR^{R1}$ (with the BOR protein concentration normalised to 10 μM), 10 mM borane, 10 mM diazo ester, 10 mM $Na_2S_2O_4$, 5 vol % MeCN, M9-N buffer at room temperature under anaerobic conditions for various time intervals. See Methods section of the manuscript for cell lysate preparation procedure.

Purified protein-catalysed reaction: Experiments were performed using purified $BOR^{WT}$ or $BOR^{R1}$ (10 μM), 10 mM borane, 10 mM diazo ester, 10 mM $Na_2S_2O_4$, 5 vol % MeCN, M9-N buffer at room temperature under anaerobic conditions for various time intervals. See Methods section of the manuscript for purified protein preparation procedure General Procedure for Timed Experiments:

In an anaerobic chamber, 3.8 mL of whole *E. coli* cells harboring BOR variant, or a solution of 3.4 mL of BOR variant cell lysate/purified protein and 0.4 mL $Na_2S_2O_4$ (100 mM in M9-N buffer), was added to a 10 mL glass vial. After charging NHC-borane 1 (100 μL, 400 mM in MeCN) and Me-EDA 2 (100 μL, 400 mM in MeCN), the vial was capped and the reaction was shaken at 600 rpm on an orbital shaker. At regular time intervals (see table below), 400 μL of the reaction mixture was removed from the vial and added to a 2 mL microcentrifuge tube containing 600 μL cyclohexane/ EtOAc (1:1 v/v) and internal standard (20 μL, 20 mM 1,2,3-trimethoxybenzene in toluene). After vortexing for 20 seconds, 200 μL of the organic layer was immediately removed for GC analysis. The following table shows time points at which the biocatalytic reaction was sampled to determine the reaction initial rate.

| Biocatalysts | Sampling time |
|---|---|
| $BOR^{WT}$ purified protein | Every hour from t = 1 to 4 h |
| $BOR^{WT}$ cell lysate | Every hour from t = 1 to 4 h |
| $BOR^{WT}$ whole cell | Every minute from t = 1 to 4 min |
| $BOR^{R1}$ purified protein | Every minute from t = 1 to 4 min |
| $BOR^{R1}$ cell lysate | Every minute from t = 0.5 to 3.5 min |
| $BOR^{R1}$ whole cell | Every minute from t = 0.5 to 3.5 min |

Figure 6E:
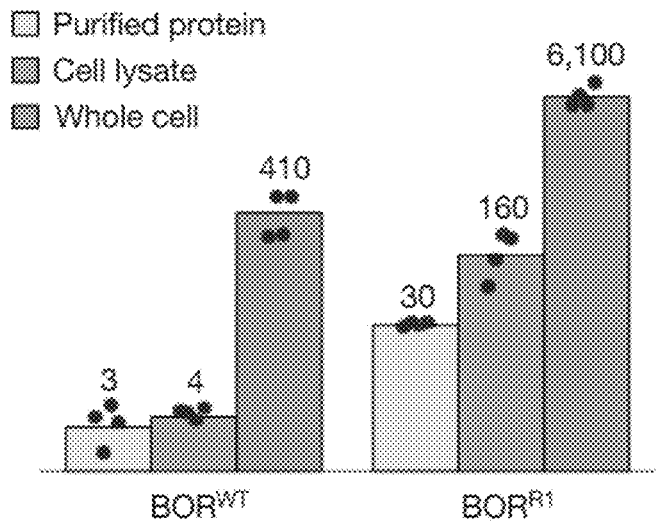
FIG. 6E shows the turnover frequencies (TOFs) of BOR$^{WT}$ and BOR$^{R1}$ as purified proteins (left bars), cell lysates (middle bars), or whole-cell catalysts (right bars), for the production of organoborane 3.
Figure 6F:
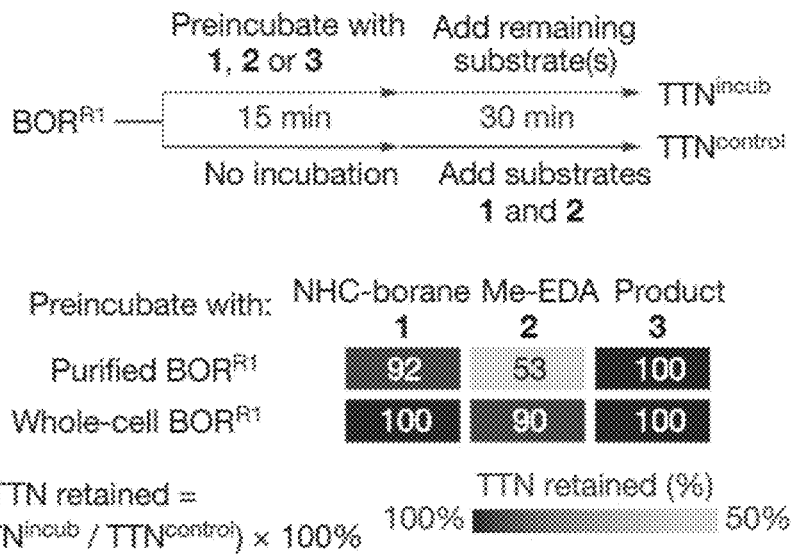
FIG. 6F shows a scheme for purified and whole-cell BOR$^{R1}$, preincubated with NHC-borane 1, Me-EDA 2, or organoborane 3 before they were used as borylation catalysts to determine the inhibitory effects of 1-3. Bars and numbers above bars represent mean values averaged over four experiments. Error bars indicate one standard deviation. BSA, bovine serum albumin.

Interestingly, as purified protein or in cell lysate, both $BOR^{R1}$ and $BOR^{WT}$ are orders of magnitude slower (FIG. 6E). When isolated $BOR^{R1}$ protein and whole-cell $BOR^{R1}$ were preincubated with Me-EDA 2 before the borylation reaction, the isolated protein retained only ~50% of its activity, whereas whole-cell $BOR^{R1}$ retained >90% activity (FIG. 6F).

Example 9: Borylation Reagents and Products do not Inactivate Engineered Catalysts Inactivation studies of $BOR^{R1}$ were carried out using purified protein or whole cell *E. coli* harboring $BOR^{R1}$. Effects of NHC-borane 1, Me-EDA 2, or organoborane 3 were determined by preincubating the biocatalyst with either one of these reagents (10 mM) for 15 min before the catalyst was used for borylation, and by comparing the TTN of the resulting catalyst ($TTN^{incub}$) with that of an untreated biocatalyst ($TTN^{control}$), as described in FIG. 6F.

Purified protein-catalysed reactions were performed using purified $BOR^{R1}$ (10 μM), 10 mM borane, 10 mM diazo ester, 10 mM $Na_2S_2O_4$, 5 vol % MeCN, M9-N buffer at room temperature under anaerobic conditions for 30 min. See Methods section of the manuscript for purified protein preparation procedure Whole cell-catalysed reactions were performed using whole *E. coli* cells harbouring $BOR^{R1}$ (with the BOR protein concentration normalised to 10 μM), 10 mM borane, 10 mM diazo ester, 5 vol % MeCN, M9-N buffer at room temperature under anaerobic conditions for 30 min.

NHC-borane 1 and organoborane product 3 did not inactivate the enzyme. Me-EDA likely inactivates $BOR^{R1}$ through carbene transfer to the heme cofactor and/or nucleophilic side chains of the protein, a mechanism we previously studied in detail for a cytochrome P450-based carbene transferase[30]. The intact periplasm apparently protects $BOR^{R1}$ from inactivation by Me-EDA, and carbene transfer to yield the organoborane product is generally faster than protein inactivation pathway(s) under those conditions. Similar observations have been reported for other protein-based carbene transfer reaction systems.[7,31]

Example 10: Organoboron Chemistry does not Affect Cell Viability

Figure 7:
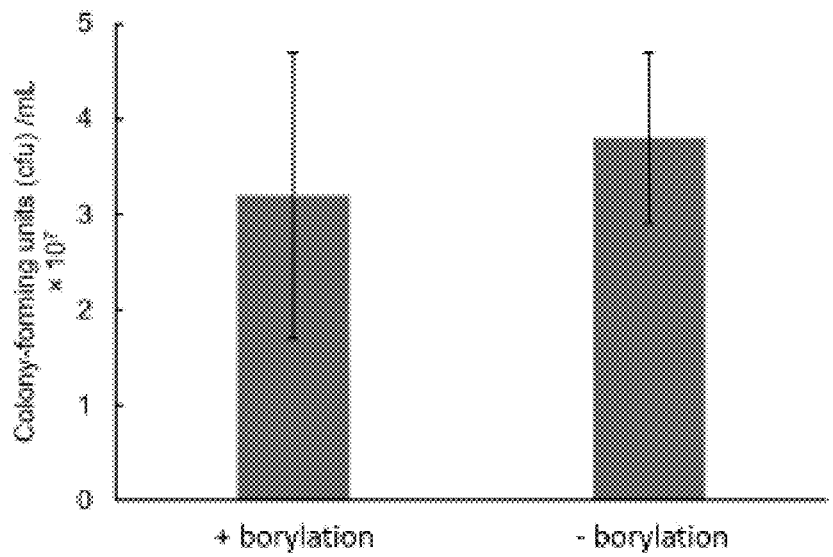
FIG. 7 shows the effect of biological borylation on *E. coli* cell viability.

Analysis of colony-forming units shows that in vivo organoborane production does not dramatically reduce the viability of the *E. coli* (FIG. 7). The colony forming units (cfu) of whole-cell reactions (+ borylation) and controls without borylation reagents (− borylation) were determined with biological replicates according to the following procedures. Six 2 mL screw cap vials containing 380 μL suspension of *E. coli* harbouring $BOR^{R1}$ ($OD_{600}$=15) were transferred to an anaerobic chamber. To three of these vials were added NHC-borane 1 (10 μL, 400 mM in MeCN) and Me-EDA 2 (10 μL, 400 mM in MeCN). These vials were capped and shaken at 500 rpm in the anaerobic chamber (+ borylation). The remaining three vials were capped and shaken in the absence of reagents 1 and 2 (− borylation). After 2.5 hours, all six vials were removed from the anaerobic chamber. Aliquots of cell suspension were removed the vials and subjected to serial dilution to obtain stock solutions of $10^6$, $10^7$, and $10^8$-fold dilution. 50 μL of each stock solution was plated on LBamp/chlor agar plates and incubate at 37° C. overnight. The cfu of the cell suspensions were calculated based on the colony counts of $10^7$-dilution plate. The cfu for each vial are shown in FIG. 7.

Example 11: Preparation and Evaluation of Boron Reagents

Figure 8A:
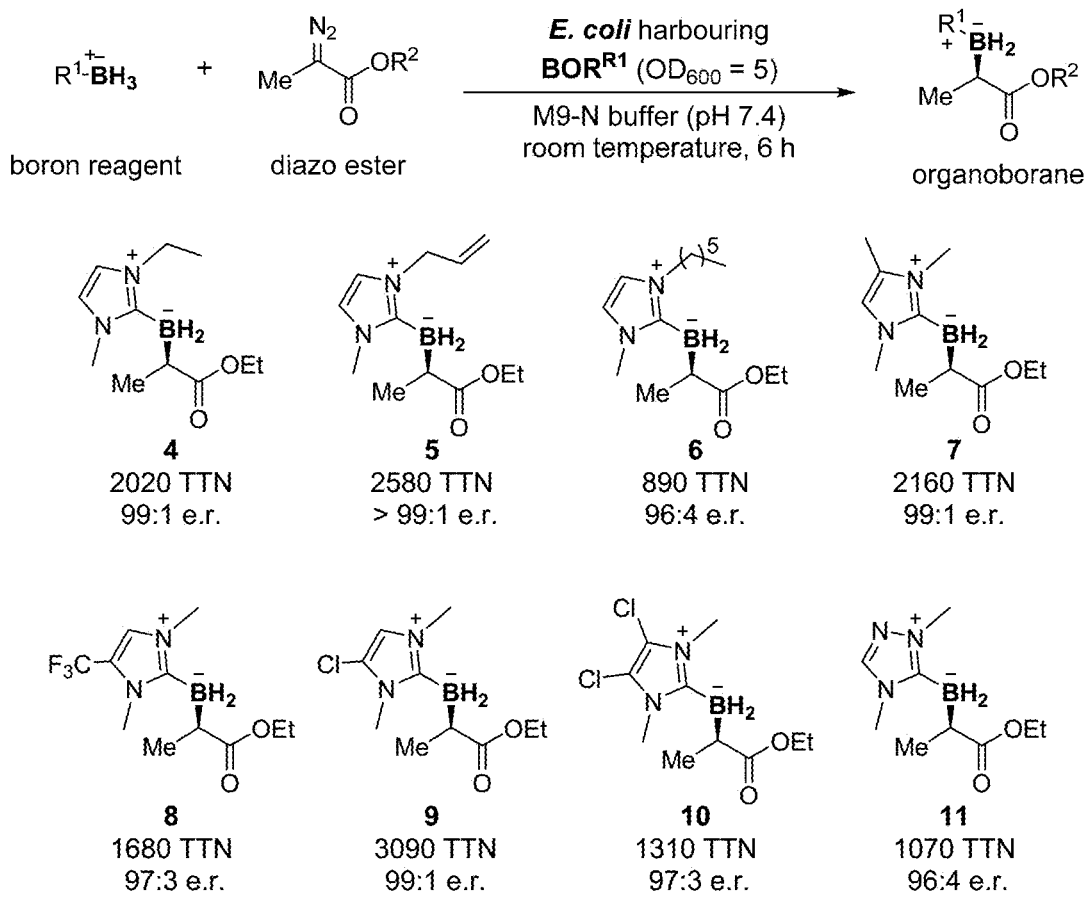
FIG. 8A shows the scope of boron reagents for chiral organoborane production in *E. coli* harboring BOR$^{R1}$. Standard substrate loading was 10 mM, and reactions were conducted in duplicate.

We next explored the scope of boron reagents that could function in the cellular environment. Ten boron reagents were tested under turnover-optimised conditions: though the size, solubility and lipophilicity of these reagents varied, all were found to permeate the cell membrane and give the desired products in excellent selectivities and turnovers (FIG. 8A).

Picoline borane substrate was obtained from Sigma-Aldrich. Ethyl 2-diazopropanoate (Me-EDA) was obtained from Arch Bioscience. All commercially available reagents were used as received. The following diazo compounds are known and prepared according to literature procedures: methyl 2-diazopropanoate[32], isopropyl 2-diazopropanoate[33], benzyl 2-diazopro-panoate[34], ethyl 2-phenyldiazoacetate (Ph-EDA)[35], ethyl 2-diazo-3,3,3-trifluoropropanoate $(CF_3\text{-}EDA)^{36}$, and (1-diazo-2,2,2-trifluoroethyl)benzene $(CF_3\text{-}DMB)^{37}$.

Other NHC—$BH_3$ substrates were synthesized from corresponding imidazolium iodide salts as reported[38]. Namely, imidazolium iodide salts (5 mmol) were resuspended in 5 mL THF. A solution of NaHMDS (1M in THF, 1.05 equiv.) was then added at −78° C. under Ar and shaken for 1 h at −78° C. Afterwards, a solution of $BH_3$-THF (1M in THF, 1 equiv.) was added to the reaction and the reaction mixture was allowed to warm from −78° C. to rt and stirred overnight. The solvent was removed under reduced pressure and the residue was purified by flash column chromatography to give the NHC—$BH_3$ complexes. The $^1H$ NMR resonances of the B—H protons are broad (due to geminal coupling with boron) and generally in the range of 0.4-1.6 ppm. The $^{13}C$ NMR resonances of the boron-binding NHC quaternary carbons usually appear at around 170 ppm and are typically broad (due to germinal coupling with boron) and weak; these signals are sometimes not visible in the $^{13}C$ NMR spectra.

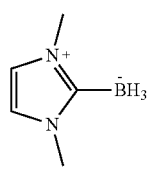

(1)

Compound 1 has been reported previously, and was prepared as described in the general procedure above.[39] $^1H$ NMR (400 MHz, Chloroform-d) δ 6.91-6.66 (m, 2H), 3.71 (s, 6H), 0.99 (dd, J=172.7, 86.3 Hz, 3H).

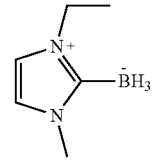

(4a)

Compound 4a has been reported previously, and was prepared as described in the general procedure above.[40] $^1H$ NMR (400 MHz, Chloroform-d) δ 6.87-6.65 (m, 2H), 4.00 (q, J=7.3 Hz, 2H), 3.57 (s, 3H), 1.22 (t, J=7.3 Hz, 3H), 1.44-0.30 (m, 3H).

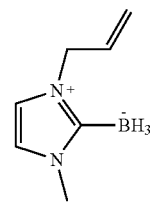

(5a)

Compound 5a has been reported previously, and was prepared as described in the general procedure above.[39] $^1H$ NMR (400 MHz, Chloroform-d) δ 6.84-6.79 (m, 2H), 5.91 (ddt, J=17.1, 10.2, 6.1 Hz, 1H), 5.30-5.06 (m, 2H), 4.71 (dt, J=6.1, 1.5 Hz, 2H), 3.71 (s, 3H), 1.43-0.35 (m, 3H).

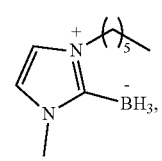

(6a)

Compound 6a was prepared as described in the general procedure above. $^1H$ NMR (400 MHz, Chloroform-d) δ 6.82-6.76 (m, 2H), 4.13-3.97 (m, 2H), 3.69 (s, 3H), 1.83-1.63 (m, 2H), 1.42-1.19 (m, 6H), 0.97-0.75 (m, 3H), 1.46-0.41 (m, 3H); $^{13}C$ NMR (101 MHz, $CDCl_3$) δ 171.0, 119.9, 118.7, 48.8, 35.8, 31.3, 30.1, 26.1, 22.5, 14.0; $^{11}B$ NMR (128 MHz, Chloroform-d) δ −37.4 (q, J=86 Hz); MS (FAB) m/z [(M+H)$^+$—$H_2$] calcd for $C_{10}H_{20}N_2B$: 179.1720, found: 179.1707.

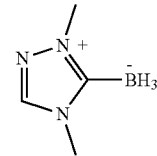

(11a)

Compound 11a has been reported previously, and was prepared as described in the general procedure above.[39] $^1H$ NMR (400 MHz, Chloroform-d) δ 7.85 (s, 1H), 3.94 (s, 3H), 3.74 (s, 3H), 1.45-0.42 (m, 3H).

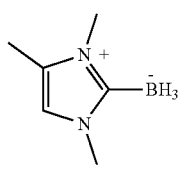

(7a)

Compound 7a has been reported previously, and was prepared as described in the general procedure above.[41] $^1$H NMR (400 MHz, Chloroform-d) δ 6.49 (q, J=1.2 Hz, 1H), 3.56 (s, 3H), 3.50 (s, 3H), 2.07 (d, J=1.3 Hz, 3H), 1.31-0.43 (m, 3H).

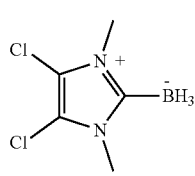

(10a)

Compound 10a has been reported previously, and was prepared as described in the general procedure above.[42] $^1$H NMR (400 MHz, Chloroform-d) δ 3.72 (s, 6H), 1.44-0.41 (m, 3H).

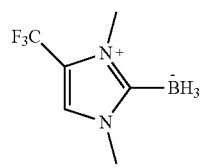

(8a)

Compound 8a was prepared as described in the general procedure above. $^1$H NMR (400 MHz, Chloroform-d) δ 7.23 (q, J=1.5 Hz, 1H), 3.82 (s, 3H), 3.77 (s, 3H), 1.49-0.54 (m, 3H). $^{13}$C NMR (101 MHz, CDCl$_3$) δ 177.1, 122.2, 121.8, 119.40 (q, J=267.3 Hz), 36.5, 34.0. $^{11}$B NMR (128 MHz, Chloroform-d) δ −37.4 (q, J=88 Hz). $^{19}$F NMR (282 MHz, Chloroform-d) δ −61.2 (d, J=3 Hz); MS (FAB) m/z [(M+H)$^+$—H$_2$] calcd for C$_6$H$_9$F$_3$N$_2$B: 177.0811, found: 177.0815.

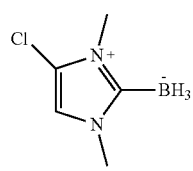

(9a)

Compound 9a was prepared as described in the general procedure above. $^1$H NMR (400 MHz, Chloroform-d) δ 6.78 (s, 1H), 3.71 (s, 3H), 3.67 (s, 3H), 1.45-0.51 (m, 3H). $^{13}$C NMR (101 MHz, CDCl$_3$) δ $^{13}$C NMR (101 MHz, CDCl$_3$) δ 173.5, 119.3, 116.9, 36.4, 33.0. $^{11}$B NMR (128 MHz, Chloroform-d) δ −36.9 (q, J=87 Hz); MS (FAB) m/z [(M+H)$^+$—H$_2$] calcd for C$_5$H$_9$N$_2$BCl: 143.0547, found: 143.0547.

Various substitutions on the NHC nitrogen are tolerated (3 to 10). The reaction is chemoselective in the presence of terminal olefins (5), which could function as a reaction handle suitable for downstream biological or bio-orthogonal derivatization. Sterically more demanding tetra- and penta-substituted NHCs are also accepted (7 to 10). Beside imidazole-based boron reagents, triazolylidene borane and picoline borane could also be used for in vivo borylation, yielding products 11 and 12 in 1070 TTN and 2440 TTN, respectively, with uniformly high selectivities (96:4 e.r.).

Figure 8B:
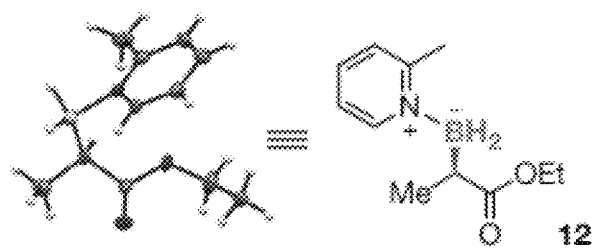
FIG. 8B shows results of the gram scale synthesis (8.4 mmol) of organoborane 12 catalyzed by whole-cell BOR$^{R1}$ ($OD_{600}$=30). The small scale preparation of 12 (2440 TTN, 96:4 e.r.) was also reported for comparison. The absolute configuration of biosynthesized 12 was assigned to be R by X-ray crystallography.

On gram scale, in vivo borylation produced 740 mg of ethyl 2-((2-methyl-pyridin-1-yl)boraneyl)propanoate (12) with 2910 TTN, 96:4 e.r. and 42% isolated yield (64% based on recovered starting material, FIG. 8B). The absolute configuration of 12 was assigned to be R by X-ray crystallography.

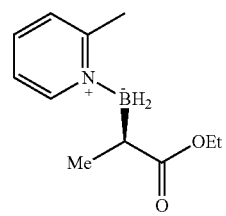

12

Under anaerobic conditions, to a 250 mL conical flask were added 50 mL Rma cyt c BOR$^{R1}$ whole-cell solution (OD$_{600}$=30), glucose (2.6 mL, 1 M), picoline borane (1.4 mL, 2 M in MeCN) and Me-EDA (1.4 M in MeCN). The flask was shaken at 240 rpm in an anaerobic chamber. At 3 h intervals, two additional batches of whole-cell solution (50 mL), glucose (2.6 mL, 1 M), picoline borane (1.4 mL, 2 M in MeCN) and Me-EDA (1.4 M in MeCN) were added. The reaction mixture was shaken for a total of 24 hours and then divided between six 50 mL Falcon tubes. 25 mL 3:7 hexanes/EtOAc was added to each tube to extract the borylation product via vortexing (30 s for three times) and centrifugation (5,000×g, 5 min). After removal of the organic layers, two additional rounds of extraction were performed. The combined organic extracts were dried over anhydrous Na$_2$SO$_4$, concentrated, and purified by flash chromatography (dry loading) with EtOAc/hexanes (5% to 40% EtOAc/hexanes gradient) to afford pure organoborane product 12 (0.74 g, 3.57 mmol, 42% yield). The protein concentration of OD$_{600}$=30 whole-cell solution was determined to be 8.18 μM by hemochrome assay after cell lysis by sonication. The total turnover number for this reaction was 2910. The stereoselectivity of the product was determined as 96:4 e.r. by normal-phase chiral HPLC. [α]$_D^{23}$=+117.2 (c 0.37, EtOAc). $^1$H NMR (400 MHz, Chloroform-d) δ 8.53 (dd, J=6.0, 1.6 Hz, 1H), 7.84 (td, J=7.7, 1.7 Hz, 1H), 7.42-7.36 (m, 1H), 7.33-7.28 (m, 1H), 3.79 (AB qq, J=10.8, 7.1 Hz, 2H), 3.30-2.15 (m, 2H), 2.77 (s, 3H), 2.05-1.92 (m, 1H), 1.05 (d, J=6.8 Hz, 3H), 0.94 (t, J=7.1 Hz, 3H). $^{13}$C NMR (101 MHz, Chloroform-d) δ 182.13, 157.92, 149.35, 140.26, 127.67, 122.60, 58.83, 32.78, 22.76, 15.16, 14.61. $^{11}$B NMR (128 MHz, Chloroform-d) δ −5.10 (t, J=103 Hz).

Synthesis and Characterization of Authentic Organoborane Products.

Racemic standard references of organoborane products were prepared via Rh-catalyzed B—H insertion reactions with procedures slightly modified from a previously reported method[39]. Namely, a 4 mL vial with screw cap and PTFE septum was charged with a borane substrate (1.0 mmol, 1 equiv.) and Rh$_2$(OAc)$_4$ (11 mg, 2.5 mol %). The vial was evacuated and backfilled with Ar three times and 2 mL of anhydrous CH$_2$Cl$_2$ was added. The vial was placed in a 38° C. water bath. A CH$_2$Cl$_2$ solution (1 mL) of diazo compound (1.0 mmol) was slowly added to the reaction mixture over 4 hours. Afterwards, the reaction mixture was allowed to further react overnight. The crude reaction mixture was purified by flash chromatography (dry loading) using EtOAc and hexanes as eluents and afforded organoborane products in 30-75% yield. The $^1$H NMR resonances of the B—H protons are broad (due to geminal coupling with boron) and generally in the range of 0.4-1.6 ppm. The $^{13}$C NMR resonances of the boron-binding NHC quaternary carbons usually appear at around 170 ppm and are typically broad (due to germinal coupling with boron) and weak; these signals are sometimes not visible in the $^{13}$C NMR spectra.

(1,3-Dimethyl-1H-imidazol-3-ium-2-yl)(1-ethoxy-1-oxopropan-2-yl)dihydroborate (3)

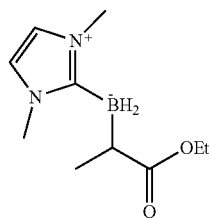

$^1$H NMR (400 MHz, Chloroform-d) δ 6.82 (s, 2H), 3.98-3.78 (m, 2H), 3.75 (s, 6H), 1.95-1.10 (m, 2H), 1.88 (br s, 1H), 1.10 (d, J=6.2 Hz, 3H), 1.06 (t, J=7.1 Hz, 3H); $^{13}$C NMR (101 MHz, Chloroform-d) δ 183.5, 120.4, 58.7, 36.2, 30.5, 17.8, 14.6. The boron-bound NHC quaternary carbon was not resolved; $^{11}$B NMR (128 MHz, Chloroform-d) δ −24.6 (t, J=90 Hz); MS (FAB) m/z [(M+H)$^+$—H$_2$] calcd for C$_{10}$H$_{18}$O$_2$N$_2$B: 209.1461, found: 209.1456.

(1-Ethoxy-1-oxopropan-2-yl)(3-ethyl-1-methyl-1H-imidazol-3-ium-2-yl)dihydroborate (4)

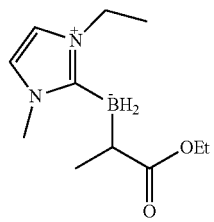

$^1$H NMR (400 MHz, Chloroform-d) δ 6.91-6.82 (m, 2H), 4.28-3.97 (m, 2H), 3.93-3.73 (m, 2H), 3.70 (s, 3H), 1.84 (br s, 1H), 1.95-1.10 (br m, 2H), 1.34 (t, J=7.3 Hz, 3H), 1.05 (d, J=6.7 Hz, 3H), 0.98 (t, J=7.2 Hz, 3H); $^{13}$C NMR (101 MHz, Chloroform-d) δ 183.3, 170.0, 120.7, 118.2, 58.4, 43.5, 35.9, 30.4, 17.6, 15.8, 14.4; $^{11}$B NMR (128 MHz, Chloroform-d) δ −24.5 (t, J=89 Hz). MS (FAB) m/z [M$^+$] calcd for C$_{11}$H$_{21}$O$_2$N$_2$B: 224.1696, found: 224.1693.

(3-Allyl-1-methyl-1H-imidazol-3-ium-2-yl)(1-ethoxy-1-oxopropan-2-yl)dihydroborate (5)

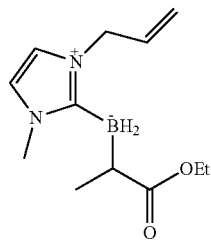

$^1$H NMR (400 MHz, Chloroform-d) δ 6.85 (AB q, J=2.0 Hz, 2H), 5.94 (ddt, J=17.1, 10.2, 6.1 Hz, 1H), 5.39-5.17 (m, 2H), 4.82 (ddt, J=15.3, 6.0, 1.5 Hz, 1H), 4.68 (ddt, J=15.3, 6.2, 1.4 Hz, 1H), 3.99-3.78 (m, 2H), 3.76 (s, 3H), 1.92-1.05 (m, 2H), 1.87 (br s, 1H), 1.09 (d, J=6.6 Hz, 3H), 1.05 (t, J=7.1 Hz, 3H); $^{13}$C NMR (101 MHz, Chloroform-d) δ 183.6, 132.9, 120.9, 119.7, 119.0, 58.8, 51.4, 36.4, 32.0, 17.9, 14.8. The boron-bound NHC quaternary carbon was not resolved; $^{11}$B NMR (128 MHz, Chloroform-d) δ −24.6 (t, J=90 Hz). MS (FAB) m/z [M+H$^+$] calcd for C$_{12}$H$_{22}$O$_2$N$_2$B: 237.1774, found: 237.1783.

(1-Ethoxy-1-oxopropan-2-yl)(3-hexyl-1-methyl-1H-imidazol-3-ium-2-yl)dihydroborate (6)

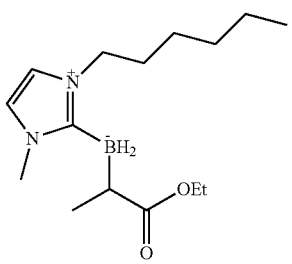

$^1$H NMR (400 MHz, Chloroform-d) δ 6.88-6.79 (m, 2H), 4.20-4.06 (m, 1H), 3.99 (m, 1H), 3.93-3.74 (m, 2H), 3.72 (s, 3H), 1.93-1.79 (m, 1H), 1.72 (dt, J=13.8, 6.9 Hz, 2H), 1.71-1.20 (m, 8H), 1.12-1.05 (m, 3H), 1.01 (td, J=7.2, 2.4 Hz, 3H), 0.90-0.80 (m, 3H); $^{13}$C NMR (101 MHz, Chloroform-d) δ 183.6, 120.7, 119.0, 58.7, 48.9, 36.2, 31.6, 30.8, 30.5, 26.5, 22.7, 17.9, 14.7, 14.2. The boron-bound NHC quaternary carbon was not resolved; $^{11}$B NMR (128 MHz, Chloroform-d) δ −24.5 (t, J=90 Hz); MS (FAB) m/z [M$^+$] calcd for C$_{15}$H$_{29}$O$_2$N$_2$B: 280.2322, found: 280.2330.

(1-Ethoxy-1-oxopropan-2-yl)(1,3,4-trimethyl-1H-imidazol-3-ium-2-yl)dihydroborate (7)

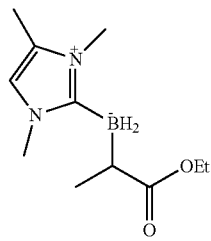

$^1$H NMR (400 MHz, Chloroform-d) δ 6.55 (q, J=1.2 Hz, 1H), 3.95-3.77 (m, 2H), 3.66 (s, 3H), 3.61 (s, 3H), 2.16 (d, J=1.1 Hz, 3H), 1.84 (br s, 1H), 1.93-1.10 (m, 2H), 1.07 (s, 3H), 1.12-1.02 (m, 3H); $^{13}$C NMR (101 MHz, Chloroform-d) δ 183.7, 170.0, 128.3, 117.6, 58.7, 35.9, 32.7, 32.0-29.5 (m), 17.9, 14.7, 9.7; $^{11}$B NMR (128 MHz, Chloroform-d) δ −24.2 (t, J=89 Hz); MS (FAB) m/z [M$^{+•}$] calcd for $C_{11}H_{22}O_2N_2B$: 224.1696, found: 224.1695.

(1,3-Dimethyl-4-(trifluoromethyl)-1H-imidazol-3-ium-2-yl)(1-ethoxy-1-oxopropan-2-yl)dihydroborate (8)

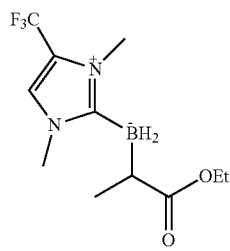

$^1$H NMR (400 MHz, Chloroform-d) δ 7.29 (q, J=1.3 Hz, 1H), 4.00-3.70 (m, 2H), 3.85 (s, 3H), 3.81 (s, 3H), 1.88 (br s, 1H), 1.85-1.05 (m, 2H), 1.12 (d, J=6.6 Hz, 3H), 1.05 (t, J=7.1 Hz, 3H); $^{13}$C NMR (101 MHz, Chloroform-d) δ 183.2, 123.6, 122.8-122.5 (m), 119.6 (q, J=267.6 Hz), 59.0, 36.9, 34.4, 30.0, 17.9, 14.7. The boron-bound NHC quaternary carbon was not resolved; $^{11}$B NMR (128 MHz, Chloroform-d) δ −24.7 (t, J=91 Hz). $^{19}$F NMR (282 MHz, Chloroform-d) δ −61.1; MS (FAB) m/z [M$^{+•}$] calcd for $C_{11}H_{18}O_2N_2BF_3$: 278.1414, found: 278.1405.

(4-Chloro-1,3-dimethyl-1H-imidazol-3-ium-2-yl)(1-ethoxy-1-oxopropan-2-yl)dihydroborate (9)

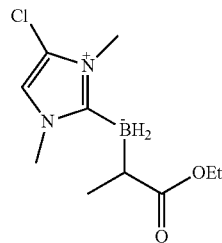

$^1$H NMR (400 MHz, Chloroform-d) δ 6.83 (s, 1H), 3.97-3.79 (m, 2H), 3.73 (s, 3H), 3.70 (s, 3H), 2.00-1.10 (m, 2H), 1.94-1.76 (m, 1H), 1.13-1.02 (m, 6H); $^{13}$C NMR (101 MHz, Chloroform-d) δ 183.4, 173.0, 119.9, 117.3, 58.9, 36.6, 33.3, 30.3, 17.9, 14.7; $^{11}$B NMR (128 MHz, Chloroform-d) δ −24.2 (t, J=90 Hz); MS (FAB) m/z [M$^{+•}$] calcd for $C_{10}H_{18}O_2N_2BCl$: 244.1150, found: 244.1154.

(4,5-Dichloro-1,3-dimethyl-1H-imidazol-3-ium-2-yl)(1-ethoxy-1-oxopropan-2-yl)dihydro-borate (10)

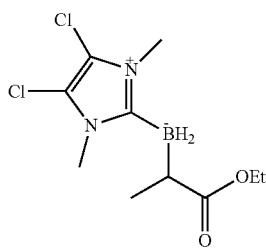

$^1$H NMR (400 MHz, Chloroform-d) δ 3.95-3.78 (m, 2H), 3.72 (s, 6H), 1.83 (br s, 1H), 1.99-1.05 (m, 2H), 1.10 (d, J=11.9 Hz, 3H), 1.05 (t, J=7.1 Hz, 3H); $^{13}$C NMR (101 MHz, Chloroform-d) δ 183.1, 172.0, 116.6, 59.0, 34.1, 30.0, 17.8, 14.7; $^{11}$B NMR (128 MHz, Chloroform-d) δ −23.9 (t, J=91 Hz); MS (FAB) m/z [M+H$^+$] calcd for $C_{10}H_{18}O_2N_2BCl_2$: 279.0838, found: 279.0846.

(1,4-Dimethyl-4H-1,2,4-triazol-1-ium-5-yl)(1-ethoxy-1-oxopropan-2-yl)dihydroborate (11)

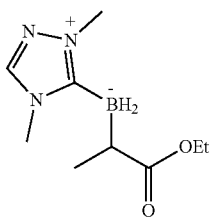

$^1$H NMR (400 MHz, Chloroform-d) δ 7.92 (s, 1H), 3.95 (s, 3H), 3.94-3.79 (m, 2H), 3.78 (s, 3H), 1.89 (br s, 1H), 2.00-1.05 (m, 2H), 1.13-1.09 (m, 3H), 1.05 (t, J=7.1 Hz, 3H). $^{13}$C NMR (101 MHz, Chloroform-d) δ 183.2, 141.7, 59.0 (d, J=8.0 Hz), 38.6, 34.1, 30.0, 17.9, 14.7. The boron-bound NHC quaternary carbon was not resolved; $^{11}$B NMR (128 MHz, Chloroform-d) δ −25.0 (t, J=91 Hz). MS (FAB) m/z [M+H$^+$] calcd for $C_9H_{19}O_2N_3B$: 212.1570, found: 212.1570.

65
Ethyl 2-((2-methyl-pyridin-1-yl)boraneyl)propanoate (12)

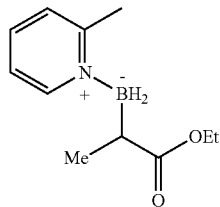

¹H NMR (400 MHz, Chloroform-d) δ 8.53 (dd, J=6.0, 1.6 Hz, 1H), 7.84 (td, J=7.7, 1.7 Hz, 1H), 7.42-7.36 (m, 1H), 7.33-7.28 (m, 1H), 3.79 (AB qq, J=10.8, 7.1 Hz, 2H), 3.30-2.15 (m, 2H), 2.77 (s, 3H), 2.05-1.92 (m, 1H), 1.05 (d, J=6.8 Hz, 3H), 0.94 (t, J=7.1 Hz, 3H); ¹³C NMR (101 MHz, Chloroform-d) δ 182.1, 157.9, 149.4, 140.2, 127.7, 122.6, 58.8, 32.8, 22.8, 15.2, 14.6; ¹¹B NMR (128 MHz, Chloroform-d) δ −5.1 (t, J=103 Hz); MS (FAB) m/z [M⁺•] calcd for $C_{11}H_{18}O_2NB$: 207.1431, found: 207.1431.

(1,3-Dimethyl-1H-imidazol-3-ium-2-yl)(1-methoxy-1-oxopropan-2-yl)dihydroborate (13)

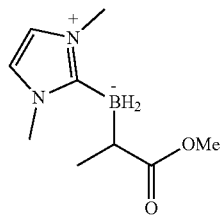

¹H NMR (400 MHz, Chloroform-d) δ 6.82 (s, 1H), 3.72 (s, 6H), 3.43 (s, 2H), 1.99-1.08 (m, 3H), 1.06 (d, J=6.8 Hz, 2H); ¹³C NMR (101 MHz, Chloroform-d) δ 183.9, 170.0, 120.6, 50.7, 36.2, 30.5, 17.8; ¹¹B NMR (128 MHz, Chloroform-d) δ −24.6 (t, J=90 Hz); MS (FAB) m/z [M⁺•] calcd for $C_9H_{17}O_2N_2B$: 196.1383, found: 196.1388.

(1,3-Dimethyl-1H-imidazol-3-ium-2-yl)(1-isopropoxy-1-oxopropan-2-yl)dihydroborate (14)

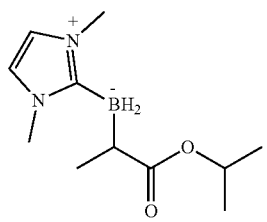

¹H NMR (400 MHz, Chloroform-d) δ 6.81 (s, 2H), 4.76 (hept, J=6.2 Hz, 1H), 3.75 (s, 6H), 1.86 (br s, 1H), 2.00-1.10 (m, 2H), 1.09 (d, J=6.2 Hz, 6H), 0.94 (d, J=6.3 Hz, 3H); ¹³C NMR (101 MHz, Chloroform-d) δ 183.3, 170.0, 120.6, 65.1, 36.4, 30.7, 22.5, 22.2, 18.1; ¹¹B NMR (128 MHz, Chloroform-d) δ −24.5 (t, J=90 Hz); MS (FAB) m/z [M⁺•] calcd for $C_{11}H_{21}O_2N_2B$: 224.1696, found: 224.1703.

66
(1-(Benzyloxy)-1-oxopropan-2-yl)(1,3-dimethyl-1H-imidazol-3-ium-2-yl)dihydroborate (15)

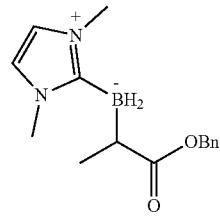

¹H NMR (400 MHz, Chloroform-d) δ 7.36-7.17 (m, 5H), 6.71 (s, 2H), 4.92 (s, 2H), 3.62 (s, 6H), 2.10-1.15 (m, 2H), 1.97 (br s, 1H), 1.16 (d, J=6.5 Hz, 3H); ¹³C NMR (101 MHz, Chloroform-d) δ 183.2, 170.0, 137.6, 128.4, 128.1, 127.7, 120.5, 64.7, 36.1, 30.8, 17.9; ¹¹B NMR (128 MHz, Chloroform-d) δ −24.5 (t, J=88 Hz); MS (FAB) m/z [(M+H)⁺—H₂] calcd for $C_{15}H_{20}O_2N_2B$: 271.1618, found: 271.1616.

(1,3-Dimethyl-1H-imidazol-3-ium-2-yl)(3-ethoxy-1,1,1-trifluoro-3-oxopropan-2-yl)dihydroborate (16)

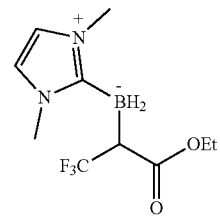

¹H NMR (400 MHz, Chloroform-d) δ 6.88 (s, 2H), 4.15-3.97 (m, 2H), 3.76 (s, 6H), 2.65 (s, 1H), 2.10-1.25 (m, 2H), 1.18 (t, J=7.1 Hz, 3H); ¹³C NMR (101 MHz, Chloroform-d) δ 174.2 (d, J=5.2 Hz), 168.0, 128.7 (q, J=276.2 Hz), 121.2, 60.0, 42.6, 36.3, 14.6; ¹¹B NMR (128 MHz, Chloroform-d) δ −28.6 (t, J=92 Hz). ¹⁹F NMR (282 MHz, Chloroform-d) δ −62.5 (d, J=10 Hz); MS (FAB) m/z [(M+H)⁺—H₂] calcd for $C_{10}H_{15}O_2N_2BF_3$: 263.1179, found: 263.1167.

(1,3-Dimethyl-1H-imidazol-3-ium-2-yl)(2-ethoxy-2-oxo-1-phenylethyl)dihydroborate (17)

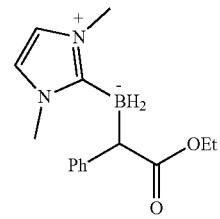

¹H NMR (400 MHz, Chloroform-d) δ 7.35-7.24 (m, 2H), 7.19-7.11 (m, 2H), 7.07-6.99 (m, 1H), 6.77 (s, 2H), 4.24-3.93 (m, 2H), 3.46 (s, 6H), 3.35-3.22 (m, 1H), 2.34-1.41 (m, 2H), 1.21 (t, J=7.1 Hz, 3H); ¹³C NMR (101 MHz, Chloroform-d) δ 179.7, 145.8, 127.9, 127.8, 124.1, 120.7, 120.2, 59.3, 45.6 (d, J=44.3 Hz), 36.0, 14.8, (the NHC quaternary carbon was too broad to be visible due to coupling with B); $^{11}$B NMR (128 MHz, Chloroform-d) δ −23.2 (t, J=93 Hz); MS (FAB) m/z calcd for $C_{15}H_{21}O_2N_2B$: 272.1696, found: 272.1687.

(1,3-Dimethyl-1H-imidazol-3-ium-2-yl)(2,2,2-trifluoro-1-phenylethyl)dihydroborate (18)

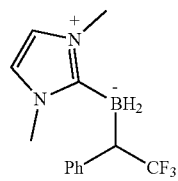

$^{1}$H NMR (400 MHz, Chloroform-d) δ 7.23-7.05 (m, 5H), 6.76 (s, 2H), 3.52 (s, 6H), 2.90-2.60 (m, 1H), 2.25-1.40 (m, 2H); $^{13}$C NMR (101 MHz, Chloroform-d) δ 169.1, 143.7 (d, J=3.5 Hz), 131.4 (q, J=278.0 Hz), 128.4, 128.3, 125.2, 120.8, 43.5, 36.0; $^{11}$B NMR (128 MHz, Chloroform-d) δ −26.7 (t, J=90 Hz); $^{19}$F NMR (282 MHz, Chloroform-d) δ −61.8 (d, J=13 Hz); MS (ESI) m/z [M+H$^+$] calcd for $C_{13}H_{17}N_2BF_3$: 269.1437, found: 269.1440.

All e.r. values of enzymatically synthesized borane products were determined using chiral SFC or normal-phase chiral HPLC. The absolute configurations of enzymatically synthesized borane products 3, 12, and 18 were determined to be R via X-ray crystallography.

For products 3 and 18, 10 mg of pure compound was dissolved in 0.5 mL ethylacetate and added to a 4 mL vial, which was then placed in a 20 mL vial containing 10 mL n-pentane. The 20 mL vial was capped, sealed with parafilm, and left undisturbed for three days at 4° C. A suitable crystal was selected and mounted in a nylon loop in immersion oil. All measurements were made on a Bruker photon diffractometer with filtered Cu-Kα radiation. Crystals of compound 12 were obtained via slow evaporation of an ethylacetate solution of 12 at room temperature.

Low-temperature diffraction data (φ- and ω-scans) were collected on a Bruker AXS D8 VENTURE KAPPA diffractometer coupled to a PHOTON 100 CMOS detector with Cu K$_\alpha$ radiation (λ=1.54178 Å) from an IμS micro-source. The structure was solved by direct methods using SHELXS[43] and refined against F$^2$ on all data by full-matrix least squares with SHELXL-2016[44] using established refinement techniques[45]. All non-hydrogen atoms were refined anisotropically. Unless otherwise noted, all hydrogen atoms were included into the model at geometrically calculated positions and refined using a riding model. The isotropic displacement parameters of all hydrogen atoms were fixed to 1.2 times the U value of the atoms they are linked to (1.5 times for methyl groups). Compound 18 (sample No. P17253) crystallizes in the monoclinic space group P21 with two molecules in the asymmetric unit. The coordinates for the hydrogen atoms bound to B1 and B2 were located in the difference Fourier synthesis and refined semi-freely with the help of a restraint on the B—H distance (1.12(4) Å). The crystal was refined as a two-component twin.

The absolute configurations of compounds 3, 12 and 18 were established by anomalous-dispersion effects using Cu K$_\alpha$ radiation (2=1.54178 Å). For P17170 (compound 3), the Flack x parameter of 0.02(7) was determined using 1062 quotients [(I$^+$)−(I$^−$)]/[(I$^+$)+(I$^−$)]. For P17207 (compound 18), the Flack x parameter of 0.08(3) was determined using 2543 quotients [(I$^+$)−(I$^−$)]/[(I$^+$)+(I$^−$)] and the Hooft y is 0.06(2). For P17253 (a two component twin, compound 12), the Flack x parameter of 0.07(10) was determined using 2069 quotients [(I$^+$)−(I$^−$)]/[(I$^+$)+(I$^−$)], the Hooft y is 0.16(9), and the PLATON P3 is 0.997. The Flack and van Hooft parameters are measures of the confidence of the absolute structure determination (zero (within several estimated standard deviation) for correct enantiomer, one for incorrect, intermediate for racemic twinning)[46,47].

The absolute configurations of organoborane products 4-11, 13-16 were inferred by analogy, assuming the facial selectivity of the diazo reagents from which these products were made remains the same as that of Me-EDA.

Example 12: Biosynthesis of Organoboranes Via Serial Substrate Addition

Figure 8C:
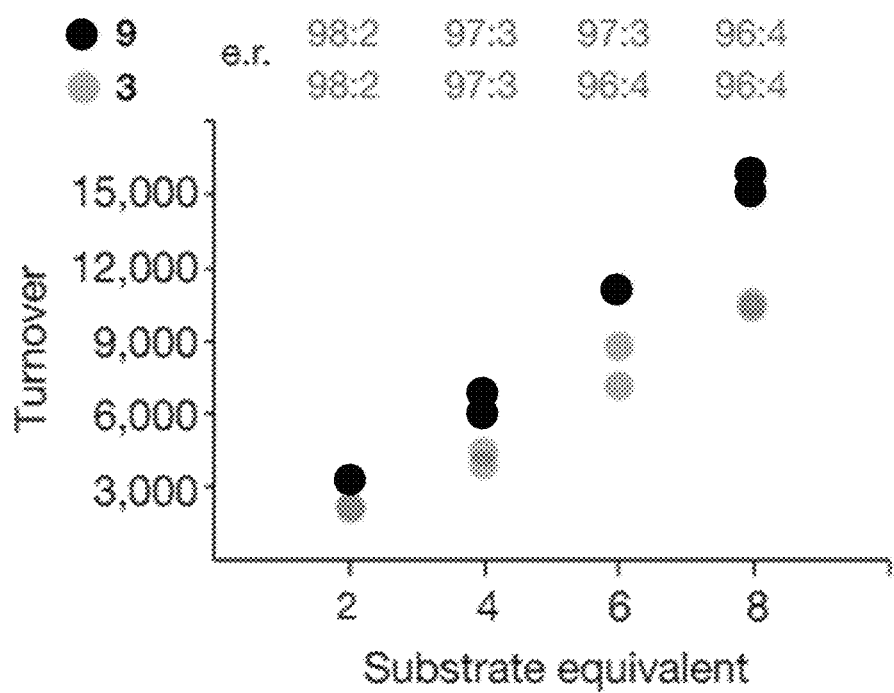
FIG. 8C shows the biosynthesis of organoboranes 9 and 3 catalyzed by whole-cell BOR$^{R1}$ ($OD_{600}$=15). One substrate equivalent (8 mM) was added to the reaction every 75 min. Reactions were conducted in duplicate. Bn, benzyl; e.r., enantiomeric ratio.

When substrates were added portion-wise at regular time intervals to *E. coli* expressing BOR$^{R1}$ (we tested the sequential addition of up to eight equivalents of substrates over a period of 12 hours, FIG. 8C; Table 3), organoborane 3 was produced with 10400 turnovers (50% yield, 96:4 e.r.), whereas organoborane 9 was obtained with 15300 turnovers (73% yield, 96:4 e.r.). No significant loss in activity or enantioselectivity was observed, demonstrating the potential of this bacterial catalyst for biosynthesis and incorporation into natural or engineered metabolic pathways.

TABLE 3

Continuous production of organoborane product via serial addition of NHC-borane and Me-EDA

3

| total equivalents of reagents | yield % of 3 | TTN of 3 | e.r. of 3 |
|---|---|---|---|
| 2 | 41 ± 1 | 2200 ± 70 | 97.5:2.5 |
| 4 | 40 ± 3 | 42000 ± 360 | 97:3 |
| 6 | 50 ± 7 | 7900 ± 400 | 96.5:3.5 |
| 8 | 49 ± 1 | 10400 ± 150 | 96.5:3.5 |

9

| total equivalents of reagents | yield % of 9 | TTN of 9 | e.r. of 9 |
|---|---|---|---|
| 2 | 61 ± 2 | 3200 ± 110 | 97.5:2.5 |
| 4 | 61 ± 6 | 6400 ± 630 | 97:3 |
| 6 | 70 ± 1 | 11000 ± 100 | 96.5:3.5 |
| 8 | 73 ± 2 | 15300 ± 490 | 96:4 |

Twelve 2 mL screw cap vials containing 400 μL suspension of cells harbouring Rma cyt c BOR$^{R1}$ (OD$_{600}$=15) and 100 μL of glucose (250 mM) were transferred to an anaerobic chamber. The twelve vials were grouped into four group sets to determine the yield, TTN, and e.r. for reactions involving the stepwise addition of 2, 4, 6 or 8 equivalents of reagents. Each equivalent is 2.5 μL it solution of NHC—BH₃ substrate in MeCN (2 M) and 2.5 μL Me-EDA solution in MeCN (2 M). The time interval between each equivalent was 75 minutes. All four group sets were shaken at 480 rpm in the anaerobic chamber until the completion of the addition and reaction for the last group set. The vials were then removed from the anaerobic chamber and quenched with 1 mL of 4:6 hexanes/ethyl acetate and 100 μL internal standard (1,2,3-trimethoxybenzene, 20 mM in toluene). The reaction mixture was transferred to a microcentrifuge tube, vortexed (10 seconds, 3 times), then centrifuged (14,000×g, 5 min) to completely separate the organic and aqueous layers (the vortex-centrifugation step was repeated if complete phase separation was not achieved). The organic layer was removed. Another 1 mL of 4:6 hexanes/ethyl acetate and 100 μL internal standard were added for a second round of extraction and the organic solutions of two rounds of extraction were combined. 300 μL of the extract was taken for GC-MS and chiral HPLC analysis to determine the yield, TTN, and e.r.

Example 13. Evaluation of Diazo Ester Reagents

Figure 8D:
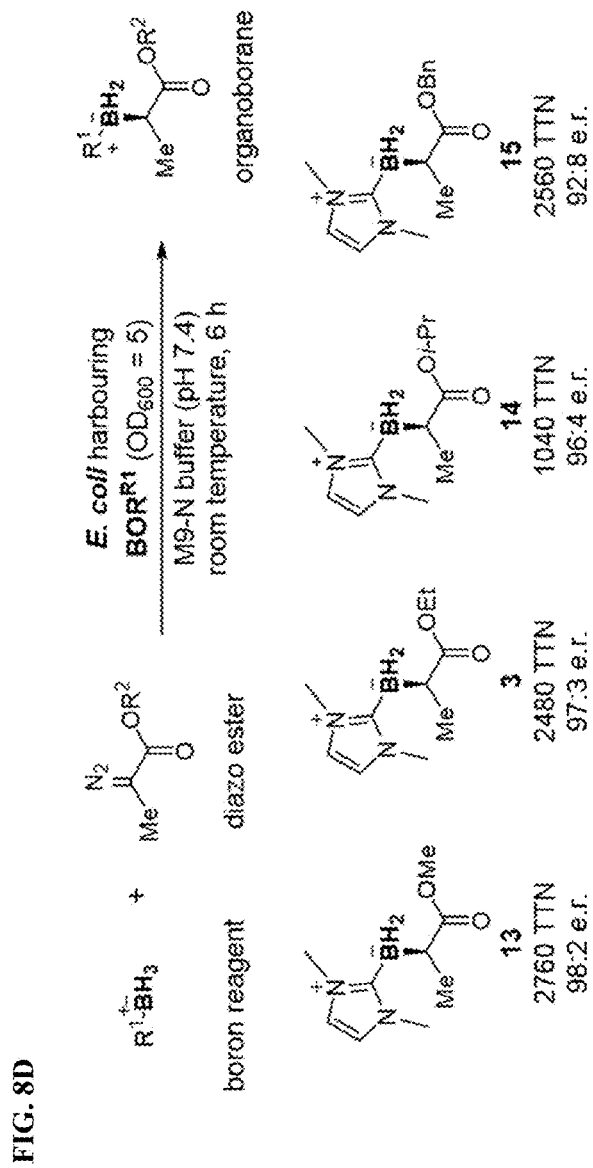
FIG. 8D shows the scope of diazo ester reagents for chiral organoborane production in *E. coli* harboring BOR$^{R1}$. Standard substrate loading was 10 mM, and reactions were conducted in duplicate.

Systematic modification of the diazo ester substituents from Et to Me, i-Pr or Bn revealed that the borylation ability of BOR$^{R1}$ is not limited to Me-EDA (3, 13 to 15, FIG. 8D). The protein's relative insensitivity to steric bulk of the ester might indicate that in the putative iron carbenoid intermediate this moiety is solvent-exposed rather than embedded within the active site. By re-randomising the 103 position in BOR$^{R1}$, a residue we believe might modulate loop dynamics for improved binding of this substrate, the borylation turnover of 15 improved (from 2560 to 4200 TTN) using V75R M100D M103D (BORR$^2$, FIG. 9A). From the same site-saturation library, a borylation catalyst for trifluoromethyl-substituted diazo ester (CF$_3$-EDA) was also discovered (V75R M100D M103F, BOR$^{R3}$). Acceptor/acceptor diazo reagents such as CF$_3$-EDA are less reactive towards carbenoid formation due to their electron-deficient nature and have not been employed before this for enzymatic carbene-transfer reactions. The present system tolerates this class of substrates and yielded product 16 with 95:5 e.r. and 1560 TTN.

Figure 9A:
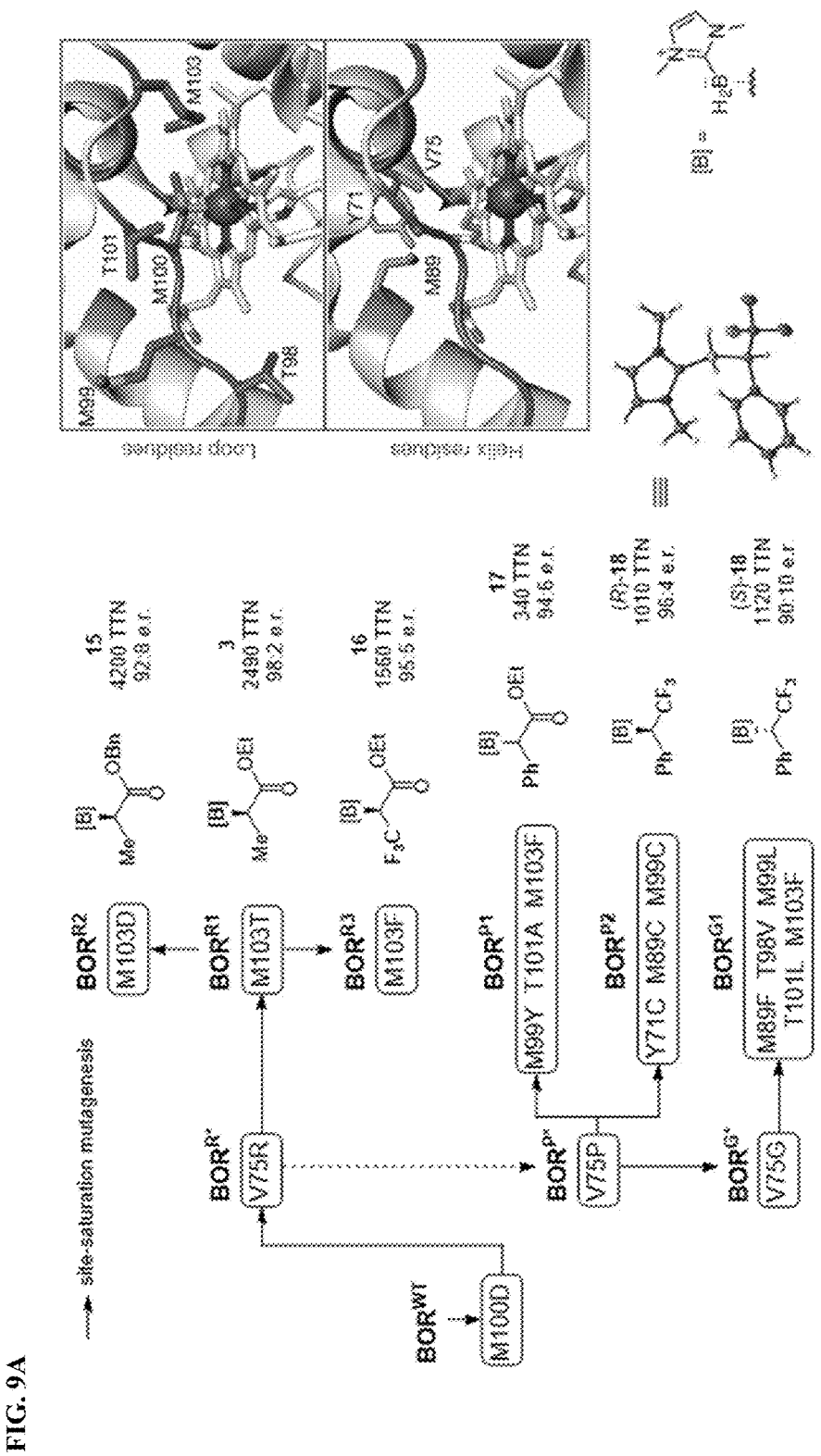
FIG. 9A depicts the generality and utility of biological borylation. The generality of in vivo borylation was expanded through directed evolution to accommodate bulky substrates (15, 17) and less reactive acceptor/acceptor diazo reagents (16), to move beyond diazo ester-based substrates (18, 19), and to provide either enantiomer of the organoborane products (18, 19). Reactions conducted in quadruplicate. Solid arrows represent site saturation mutagenesis studies. BOR$^{P}$* was discovered in the M100D V75X site-saturation mutagenesis library for Me-EDA borylation. Amino acid residues targeted during directed evolution are depicted in the X-ray crystal structure of wild-type Rma cyt c (PDB: 3CP5). The absolute configuration of biosynthesized 18 was assigned to be R by X-ray crystallography. Single-letter abbreviations for the amino acid residues are as follows: A, Ala; C, Cys; D, Asp; F, Phe; G, Gly; L, Leu; M, Met; P, Pro; R, Arg; T, Thr; V, Val; and Y, Tyr.

To further broaden the generality of this borylation platform, we re-examined the evolutionary landscape from BOR$^{WT}$ to BOR$^{R1}$ to search for promiscuous mutants that might unlock new reactivities. Double mutant V75P M100D (BOR$^{P*}$) stood out as highly productive but poorly selective (69:31 e.r.) for Me-EDA borylation in the M100D V75X site-saturation library. As proline-mediated helix kinks are known to induce structural and dynamic changes to proteins, we asked whether the V75P mutation might provide access to a unique reaction space. Ethyl 2-diazophenylacetate (Ph-EDA) is a bulky donor/acceptor diazo reagent inactive towards BOR$^{WT}$, but when added to E. coli harbouring BOR$^{P*}$ with NHC-borane 1, Ph-EDA was transformed to organoborane 17 in 100 TTN and 75:25 e.r. (FIG. 9A). By accumulating three additional loop mutations though directed evolution (M99Y, T101A and M103F; Table 4), BOR$^{P*}$ evolved into a synthetically useful catalyst (BOR$^{P1}$) for the borylation of Ph-EDA, supporting 340 turnovers with an e.r. of 94:6.

TABLE 4

Directed evolution of whole cell Rma cyt c for improved enantioselectivity in the biosynthesis of organoborane 17.

17

| mutations | e.r. of 17 |
| --- | --- |
| M100D V75P | 75:25 |
| M100D V75P M99Y | 81:19 |
| M100D V75P M99Y T101A | 89:11 |
| M100D V75P M99Y T101A M103F | 94:6 |

Example 14. Engineering of Catalysts for Expansion of Substrate Scope

BOR$^{P*}$ also allows us to move beyond diazo ester-based substrates and apply bacterial production to a different class of chiral organoboranes: though inactive towards BOR$^{WT}$, CF$_3$-substituted (diazomethyl)benzene (CF$_3$-DMB) reacted with NHC-borane 1 in the presence of BOR$^{P*}$ to yield organoborane (R)-18 in vivo.

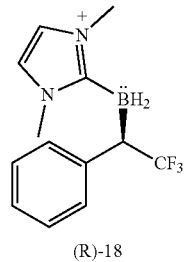

(R)-18

To a 250 mL conical flask were added 40 mL Rma cyt c BOR$^{P1}$ whole-cell solution (OD$_{600}$=30), glucose (2.6 mL, 1 M), diMeNHC—BH$_3$ (1.2 mL, 0.6 M in MeCN) and CF$_3$-DMB (1.0 mL, 0.6 M in MeCN). The flask was shaken at 240 rpm in the anaerobic chamber. After 6 hours, another batch of whole-cell solution (40 mL, OD$_{600}$=30), glucose (2.6 mL, 1 M), diMeNHC—BH$_3$ (1.2 mL, 0.6 M in MeCN) and CF$_3$-DMB (1.0 mL, 0.6 M in MeCN) were added to the reaction mixture. The reaction mixture was shaken for a total of 30 hours and then divided between four 50 mL Falcon tubes. 25 mL 3:7 hexanes/EtOAc was added to each tube to extract the borylation product via vortexing (30 s for three times) and centrifugation (5,000×g, 5 min). After removal of the organic layers, two additional rounds of extraction were performed. The combined organic extracts were dried over anhydrous Na$_2$SO$_4$, concentrated, and purified by silica column chromatography (dry loading) with EtOAc/hexanes (5% to 50% EtOAc/hexanes gradient) to afford pure organoborane product (R)-18 (130 mg, 0.485 mmol, 40% yield). Recovered borane starting material was 82 mg. The yield based on consumed starting material was 70%. The protein concentration of OD$_{600}$=30 whole-cell solution was determined to be 6.06 μM by hemochrome assay after cell lysis by sonication. The total turnover number (TTN) for this reaction was 1000. The stereoselectivity of the product was determined as 96:4 e.r. by normal-phase chiral HPLC. $[\alpha]_D^{23}$=−81.3 (c 0.67, EtOAc). $^1$H NMR (400 MHz, Chloroform-d) δ 7.23-7.05 (m, 5H), 6.76 (s, 2H), 3.52 (s, 6H), 2.90-2.60 (m, 1H), 2.25-1.40 (m, 2H); $^{13}$C NMR (101 MHz, Chloroform-d) δ 169.1, 143.7 (d, J=3.5 Hz), 131.4 (q, J=278.0 Hz), 128.4, 128.3, 125.2, 120.8, 43.5, 36.0; $^{11}$B NMR (128 MHz, Chloroform-d) δ −26.72 (t, J=90 Hz); $^{19}$F NMR (282 MHz, Chloroform-d) δ −61.80 (d, J=13 Hz).

The reaction catalyzed by BOR$^{P*}$ proceeded with 74 turnovers and modest selectivity (79:21 e.r.). We enhanced this through three cysteine mutations at Y71, M89 and M99 (BOR$^{P2}$; Table 5) to produce organoborane (R)-18 in 96:4 e.r. and 1010 TTN. Through X-ray crystallography, the absolute configuration of (R)-18 was unambiguously assigned as R.

TABLE 5

Directed evolution of whole cell Rma cyt c for improved enantioselectivity in the biosynthesis of organoborane 18

18

| mutations | e.r. of 18 |
|---|---|
| M100D V75P | 76:24 |
| M100D V75P M89C | 90:10 |
| M100D V75P M89C Y71C | 94:6 |
| M100D V75P M89C Y71C M99C | 96:4 |

Finally, we asked whether the stereochemical preference of biological borylation could be switched. Towards this end, examination of the M100D V75X site-saturation library for CF$_3$-DMB borylation led us to identify a variant (V75G M100D; BOR$^{G*}$) having an inverted stereochemical preference to BOR$^{P*}$ in the carbon-boron bond-forming step (31:69 e.r. for R/S isomer; 340 TTN). The selectivity of BOR$^{G*}$ was further tuned through mutations M89F, T98V, M99L, T101L and M103F (BOR$^{G1}$, Table 6) to yield organoborane (S)-18 with 90:10 e.r. and 1120 TTN.

TABLE 6

Directed evolution of whole cell Rma cyt c for improved enantioselectivity in the biosynthesis of organoborane 19

19

| mutations | e.r. of 19 |
|---|---|
| M100D V75G | 73:27 |
| M100D V75G M89F M103F | 78:22 |
| M100D V75G M89F M103F T101L | 86:14 |
| M100D V75G M89F M103F T101L M99L | 88:12 |
| M100D V75G M89F M103F T101L M99L T98V | 90:10 |

Example 15. Synthetic Elaboration of Enzyme Catalyzed Borylation Products

Figure 9B:
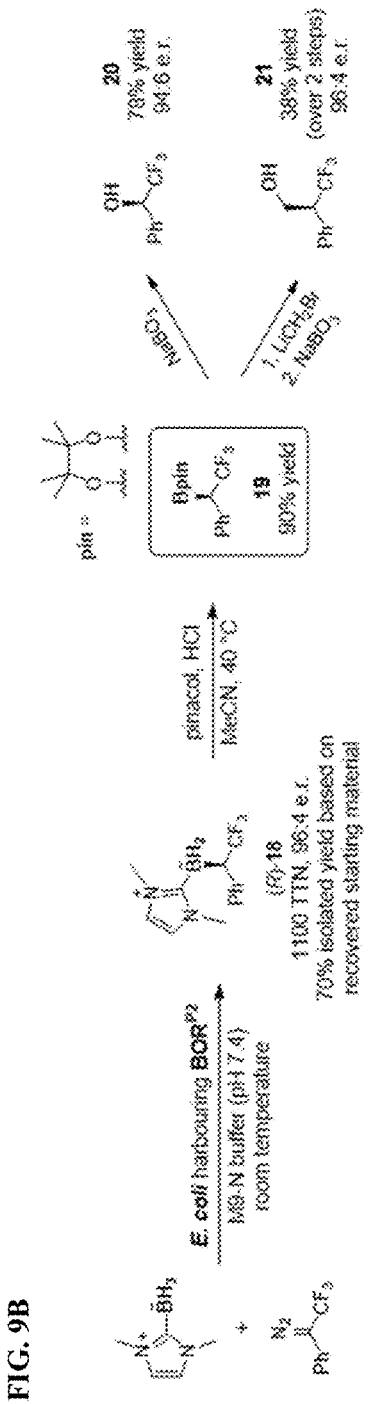
FIG. 9B shows the derivatization of biocatalytic product. Organoborane 18 was biosynthesized with *E. coli* harboring BOR$^{P2}$ (OD$_{600}$=30) on 1.3 mmol scale in 40% isolated yield (70% based on recovered starting material) for derivatization studies. Conversion to pinacol borane 20 was achieved with retention of the stereogenic carbon center (stereoselectivity determined after derivatization to alcohol 21). The yield reported for 20 was determined by $^{19}$F NMR. We demonstrated the stereospecific transformation of 20 to alcohol 21 and Mattheson homologation-oxidation product 22.

Chiral α-trifluoromethylated organoboranes are useful synthetic building blocks that combine the unique properties of fluorinated motifs with the versatile synthetic applications of organoboranes[48]; however, methods for their asymmetric preparation are rare[11,49]. Our ability to biosynthesise both enantiomers of these molecules may have applications in pharmaceutical and agrochemical synthesis. For example, product (R)-18 was converted to pinacol boronate 19 with retention of the stereogenic carbon centre (FIG. 9B). Through well-established stereospecific transformations[19-21], pinacol boronates can be diversified into a broad array of chiral compounds. We demonstrated the transformation of 19 to alcohol 20, a motif found in compounds useful for the treatment of cancer[50] and neurodegenerative diseases[51], and the Matteson homologation-oxidation product 21, both of which were obtained with good stereocontrol.

Conversion of (R)-18 to the Corresponding Pinacol Boronate Ester 19

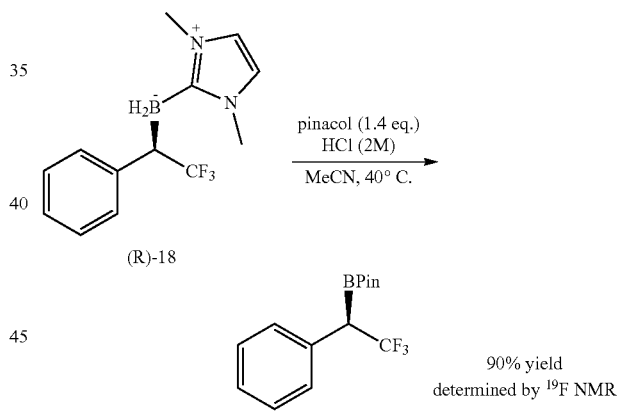

The protocol was modified from that reported by Zhou et al.[52]. To a 40 mL vial with screw cap were added 54 mg enzymatic product (R)-18 (0.2 mmol) and a stir bar. The vial was evacuated and backfilled with argon three times. 4 mL acetonitrile solution of pinacol (33 mg, 0.28 mmol, 1.4 eq.) was added to the vial via syringe. The resulting solution was stirred for 5 min for (R)-18 to dissolve, followed by the addition of 300 μL of 2 M HCl. The vial was stirred at 40° C. The reaction can be monitored by GC-MS (usual reaction time is 10-12 hours) or $^{19}$F NMR (19 has a chemical shift at δ −62.75 ppm (d, J=12 Hz)). After reaction completion, 10 μL fluorobenzene was added to the reaction mixture. An aliquot of reaction mixture was diluted with CDCl$_3$ to measure the yield via $^{19}$F NMR. The formation of 19 was confirmed by GC-MS, and by conversion of 19 to alcohol 20 (see section B below).

Conversion of Boronate Ester 19 to Alcohol 20

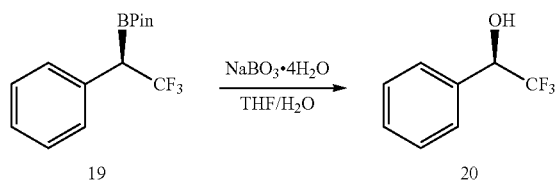

To the reaction mixture obtained after ligand exchange with pinacol in step A, 5 mL of water was added, and the mixture was extracted with 15 mL of 1:1 hexanes:EtOAc three times. The solvent was removed under reduced pressure and the vial was backfilled with argon. The crude product 19 was dissolved in 15 mL of pentane and passed through a syringe filter to remove the insoluble materials. This process was repeated two additional times to ensure all soluble materials were extracted. The combined organic extracts were dried over anhydrous $Na_2SO_4$ and concentrated under reduced pressure. Under argon, THF (1 mL) was added to the vial to dissolve the crude product 19 followed by the addition of $H_2O$ (1 mL) and 154 mg of $NaBO_3 \cdot 4H_2O$. The reaction mixture was stirred for 6 hours and extracted with EtOAc (15 mL) three times. The combined organic extracts were concentrated under reduced pressure and purified by flash column chromatography to yield alcohol 20 (0-30% hexanes/EtOAc). 27.4 mg alcohol 1 was obtained (78% yield). The e.r. was confirmed by chiral GC with FID detector using a Chiraldex GTA column (30.0 m×0.25 mm) (conditions: 120° C. isothermal at 1.0 mL/min He carrier gas flow). Retention time: 7.09 min for R enantiomer, 7.52 min for S enantiomer). This compound is known[53]. $^1$H NMR (400 MHz, Chloroform-d) δ 7.56-7.34 (m, 5H), 5.03 (qd, J=6.7, 4.4 Hz, 1H), 2.57 (dd, J=4.5, 1.5 Hz, 1H) $^{13}$C NMR (101 MHz, Chloroform-d) δ 134.3, 130.0, 129.0, 127.8, 124.6 (q, J=282.1) Hz, 73.2 (q, J=32.0 Hz). $^{19}$F NMR (282 MHz, Chloroform-d) δ −78.40 (d, J=7 Hz).

Conversion of Boronate Ester 19 to Alcohol 21 Via Matteson Homologation and Oxidation

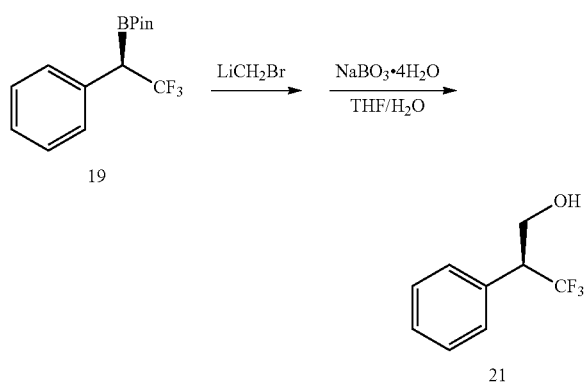

To the reaction mixture obtained after ligand exchange with pinacol in step A, 5 mL of water was added and the mixture was extracted with 15 mL of 1:1 hexanes:EtOAc three times. The solvent was removed under reduced pressure and the vial was backfilled with argon. The crude product 19 was dissolved in 15 mL of pentane and passed through a syringe filter to remove the insoluble materials. This process was repeated two additional times to ensure all soluble materials were extracted. The combined organic extracts were concentrated under reduced pressure. Under argon, 2 mL of anhydrous THF and dibromomethane (35 µL, 2.5 eq.) were added and the vial was cooled in a dry ice/acetone bath. n-BuLi (160 µL, 2.5 M in hexanes, 2.0 eq.) was added dropwise over 30 min. The solution was allowed to warm to room temperature slowly. The reaction mixture was then diluted with 3 mL sat. $NH_4Cl$ and extracted with EtOAc (15 mL) for three times. The combined organic extracts were dried over anhydrous $Na_2SO_4$ and concentrated under reduced pressure. The resulting crude mixture was dissolved in THF (1 mL). 1 mL of $H_2O$ and $NaBO_3 \cdot 4H_2O$ (154 mg) were then added and the reaction mixture was stirred for 6 hours. The reaction was then extracted with EtOAc. The organic extracts were dried, concentrated under reduced pressure, and purified by flash column chromatography to yield alcohol 21 (0-30% hexanes/EtOAc). 12.6 mg alcohol 21 was obtained (33% overall yield, 38% for the Matteson homologation and oxidation steps). The e.r. was confirmed by chiral GC with FID detector using a Chiraldex GTA column (30.0 m×0.25 mm) (conditions: 110° C. isothermal at 1.0 mL/min He carrier gas flow). Retention time: 11.625 min for S enantiomer, 12.443 min for R enantiomer). This compound is known[54]. $^1$H NMR (400 MHz, Chloroform-d) δ 7.44-7.31 (m, 5H), 4.20 (dd, J=11.7, 5.7 Hz, 1H), 4.04 (dd, J=11.4, 7.8 Hz, 1H), 3.56 (qdd, J=9.4, 7.8, 5.8 Hz, 1H), 1.57 (s, 1H). $^{13}$C NMR (101 MHz, Chloroform-d) δ 132.8 (d, J=2.2 Hz), 129.5, 129.4, 129.0, 126.4 (q, J=280.5 Hz), 61.7 (q, J=2.9 Hz), 52.9 (q, J=25.5 Hz). $^{19}$F NMR (282 MHz, Chloroform-d) δ −67.47 (d, J=9 Hz).

Example 16. Preparation of Organoboron Products with Diazohaloalkanes and Diazoesters α-Trifluoromethylated (α-$CF_3$) organoborons represent an important class of boron-containing molecules that are currently difficult to synthesize. See, e.g., Argintaru, et al. *Angew. Chem. Int. Ed.* 2013, 52, 13656-13660. These molecules possess high potentials for drug development as they can be readily converted into numerous $CF_3$-containing pharmaceutical motifs. See, e.g., Ma, et al. *Chem. Rev.* 2004, 104, 6119-6146; Purser, et al. *Chem. Soc. Rev.* 2008, 37, 320-330. However, the applications of these compounds have been hampered by the lack of methods for their enantioselective synthesis. During initial screening, several variants of Rma cytochromes c that can accept $CF_3$-substituted diazo compounds for synthesis of α-$CF_3$ organoborons were identified. This biocatalytic system would be the first general method to make chiral α-$CF_3$ organoborons and will dramatically empower their use in various biomedical research endeavors.

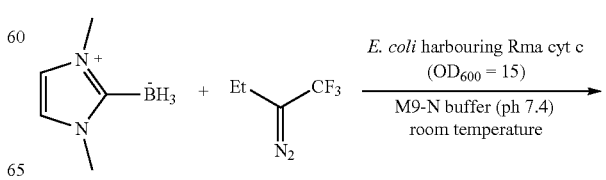

-continued

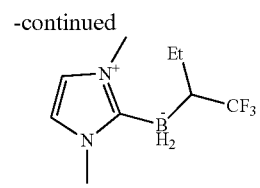

| heme proteins | Product/Internal |
|---|---|
| Rma cyt c M100D | 0.12 |
| Rma cyt c M100D V75C | 0.20 |
| Rma cyt c M100D V75T | 0.17 |

P450 variants that can utilize diazoketone substrate for B—H insertion reaction have also been identified. The obtained organoboron products can serve as intermediates for the synthesis of β-aminoboronic acids, which are important building blocks for boron-peptidomimetics. See, e.g., Smoum, et al. *Chem. Rev.* 2012, 112, 4156-4220; Touchet, et al. *Chem. Soc. Rev.* 2011, 40, 3895-3914.

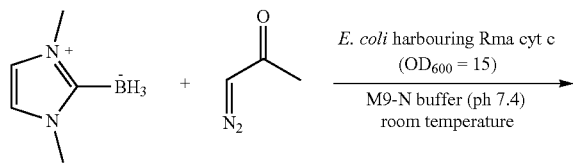

| heme proteins | Product/Internal |
|---|---|
| Rma cyt c V75R M100D M103T | NR |
| Rma cyt c M100D | NR |
| Rma cyt c V75R M100D | NR |
| P411 C8 | 1.1 |

Small-scale (400 μL) reactions were carried out in 2 mL glass crimp vials (Agilent Technologies, San Diego, Calif.). Whole cell catalysts (380 μL, $OD_{600}$=15 in M9-N minimal medium) were added to an unsealed crimp vial before crimp sealing with a silicone septum. The headspace of the vial was flushed with argon for 10 min (no bubbling). A solution of borane reagent of formula I (10 μL, 400 mM in MeCN; for example, 1,3-dimethylimidazol-2-ylidene borane) and a solution of diazo reagent (10 μL, 400 mM in MeCN; for example, ethyl 2-diazopropanoate or Me-EDA). The reaction vial was left to shake on a plate shaker at 400 rpm for 6 h at room temperature. To quench the reaction, the vial was uncapped and a 1:1 mixture of ethylacetate/hexanes (0.6 mL) was added, followed by 1,2,3-trimethoxybenzene (20 μL, 20 mM in toluene) as an internal standard. The mixture was transferred to a 1.5 mL Eppendorf tube and vortexed and centrifuged (14000× rcf, 5 min). The organic layer was analyzed by gas chromatography-mass spectrometry (GCMS).

V. References

1. Renata, H., Wang, Z. J. & Arnold, F. H. Expanding the enzyme universe: accessing non-natural reactions by mechanism-guided directed evolution. *Angew. Chem. Int. Ed.* 54, 3351-3367 (2015).
2. Hyster, T. K., Ward, T. R. Genetic optimization of metalloenzymes: Enhancing enzymes for non-natural reactions. *Angew. Chem. Int. Ed.* 55, 7344-7357 (2016).
3. Hammer, S. C., Knight, A. M., Arnold, F. H. Design and evolution of enzymes for non-natural chemistry. *Curr. Opin. Green Sustainable Chem.* (2017)
4. Coelho, P. S. et al. A serine-substituted P450 catalyzes highly efficient carbene transfer to olefins in vivo. *Nat. Chem. Biol.* 9, 485-487 (2013).
5. Jeschek, M. et al. Directed evolution of artificial metalloenzymes for in vivo metathesis. *Nature* 537, 661-665 (2016).
6. Kan, S. B. J., Lewis, R. D., Chen, K. & Arnold, F. H. Directed evolution of cytochrome c for carbon-silicon bond formation: Bringing silicon to life. *Science* 354, 1048-1051 (2016).
7. Tinoco, A., Steck, V., Tyagi, V. & Fasan, R. Highly diastereo- and enantioselective synthesis of trifluoromethyl-substituted cyclopropanes via myoglobin-catalyzed transfer of trifluoromethylcarbene. *J. Am. Chem. Soc.* 139, 5293-5296 (2017).
8. Stelter, M. et al. A novel type of monoheme cytochrome c: biochemical and structural characterization at 1.23 Å resolution of *Rhodothermus marinus* cytochrome c. Biochemistry 47, 11953-11963 (2008).
9. Cheng, Q.-Q., Zhu, S.-F., Zhang, Y.-Z., Xie, X.-L. & Zhou, Q.-L. Copper-catalyzed B—H bond insertion reaction: a highly efficient and enantioselective C—B bond-forming reaction with amine-borane and phosphine-borane adducts. *J. Am. Chem. Soc.* 135, 14094-14097 (2013).
10. Chen, D., Zhang, X., Qi, W.-Y., Bin Xu & Xu, M.-H. Rhodium(I)-catalyzed asymmetric carbene insertion into B—H bonds: highly enantioselective access to functionalized organoboranes. *J. Am. Chem. Soc.* 137, 5268-5271 (2015).
11. Hyde, S. et al. Copper-catalyzed insertion into heteroatom-hydrogen bonds with trifluorodiazoalkanes. *Angew. Chem. Int. Ed.* 55, 3785-3789 (2016).
12. Irschik, H., Schummer, D., Gerth, K., Hofle, G. & Reichenbach, H. The tartrolons, new boron-containing antibiotics from a myxobacterium, *Sorangium cellulosum. J. Antibiot.* 48, 26-30 (1995).
13. Wolkenstein, K., Sun, H., Falk, H. & Griesinger, C. Structure and absolute configuration of Jurassic polyketide-derived spiroborate pigments obtained from microgram quantities. *J. Am. Chem. Soc.* 137, 13460-13463 (2015).
14. Chen, X. et al. Structural identification of a bacterial quorum-sensing signal containing boron. *Nature* 415, 545-549 (2002).
15. Elshahawi, S. I. et al. Boronated tartrolon antibiotic produced by symbiotic cellulose-degrading bacteria in shipworm gills. *Proc. Natl. Acad. Sci. U.S.A.* 110, E295-E304 (2013).
16. Dembitsky, V. M., Aziz Al Quntar, Al, A. & Srebnik, M. Natural and synthetic small boron-containing molecules as potential inhibitors of bacterial and fungal quorum sensing. *Chem. Rev.* 111, 209-237 (2011).
17. Prier, C. K., Zhang, R. K., Buller, A. R., Brinkmann-Chen, S. & Arnold, F. H. Enantioselective, intermolecular benzylic C—H amination catalysed by an engineered iron-heme enzyme. *Nat. Chem.* 9, 629-634 (2017).
18. Das, B. C. et al. Boron chemicals in diagnosis and therapeutics. *Future Med. Chem.* 5, 653-676 (2013).
19. Miyaura, N. & Suzuki, A. Palladium-catalyzed cross-coupling reactions of organoboron compounds. *Chem. Rev.* 95, 2457-2483 (1995).

20. Leonori, D. & Aggarwal, V. K. Lithiation-borylation methodology and its application in synthesis. *Acc. Chem. Res.* 47, 3174-3183 (2014).
21. Leonori, D. & Aggarwal, V. K. Stereospecific couplings of secondary and tertiary boronic esters. *Angew. Chem. Int. Ed.* 54, 1082-1096 (2015).
22. Curran, D. P. et al. Synthesis and reactions of N-heterocyclic carbene boranes. *Angew. Chem. Int. Ed.* 50, 10294-10317 (2011).
23. Würtemberger-Pietsch, S., Radius, U. & Marder, T. B. 25 years of N-heterocyclic carbenes: activation of both main-group element-element bonds and NHCs themselves. *Dalton Trans.* 45, 5880-5895 (2016).
24. Arslan, E., Schulz, H., Zufferey, R., Künzler, P. & Thöny-Meyer, L. Overproduction of the *Bradyrhizobium japonicum* c-type cytochrome subunits of the cbb3 oxidase in *Escherichia coli. Biochem. Biophys. Res. Commun.* 251, 744-747 (1998).
25. Gibson, D. G., Young, L., Chuang, R. Y., Venter, J. C., Hutchison 3rd, C. A. & Smith, H. O. Enzymatic assembly of DNA molecules up to several hundred kilobases. *Nat. Methods* 6, 343-345 (2009).
26. Sambrook, J., Frisch, E. & Maniatis, T. *Molecular Cloning: A Laboratory Manual* (Cold Spring Harbor Laboratory Press, New York, 1989).
27. Berry, E. A. & Trumpower, B. L. Simultaneous determination of hemes a, b, and c from pyridine hemochrome spectra. *Anal. Biochem.* 161, 1-15 (1987).
28. Kille, S. et al. Reducing codon redundancy and screening effort of combinatorial protein libraries created by saturation mutagenesis. *ACS Synth. Biol.* 2, 83-92 (2013).
29. Mara, M. W. et al. Metalloprotein entatic control of ligand-metal bonds quantified by ultrafast X-ray spectroscopy. *Science* 356, 1276-1280 (2017).
30. Renata, H. et al. Identification of mechanism-based inactivation in P450-catalyzed cyclopropanation facilitates engineering of improved enzymes. *J. Am. Chem. Soc.* 138, 12527-12533 (2016).
31. Hernandez, K. E. et al. Highly Stereoselective Biocatalytic Synthesis of Key Cyclopropane Intermediate to Ticagrelor. *ACS Catal.* 6, 7810-7813 (2016).
32. L. Gao, B. C. Kang, D. H. Ryu, Catalytic asymmetric insertion of diazoesters into aryl-CHO bonds: highly enantioselective construction of chiral all-carbon quaternary centers. *J. Am. Chem. Soc.* 135, 14556-14559 (2013).
33. C. Peng, Y. Wang, J. Wang, Palladium-catalyzed cross-coupling of α-diazocarbonyl compounds with arylboronic acids. *J. Am. Chem. Soc.* 130, 1566-1567 (2008).
34. X. Gao, B. Wu, W.-X. Huang, M-W. Chen, Y-G. Zhou, Enantioselective palladium-catalyzed C—H functionalization of indoles using an axially chiral 2,2'-bipyridine ligand. *Angew. Chem. Int. Ed.* 54, 11956-11960 (2015).
35. Y. Tang, Q. Chen, X. Liu, G. Wang, L. Lin, X. Feng, Direct synthesis of chiral allenoates from the asymmetric C—H insertion of α-diazoesters into terminal alkynes. *Angew. Chem. Int. Ed.* 54, 9512-9516 (2015).
36. G. Shi, Y. Xu, Trifluoromethyl-substituted carbethoxy carbene as a novel CF3-containing a2 synthon equivalent for the preparation of 2-(trifluoromethyl)-4-oxo carboxylic ester derivatives: highly functionalized synthetic building blocks bearing a CF3 group. *J. Org. Chem.* 55, 3383-3386 (1990).
37. E. Emer, J. Twilton, M. Tredwell, S. Calderwood, T. L. Collier, B. Liégault, M. Taillefer, V. Gouverneur, Diversity-oriented approach to CF3CHF—, CF3CFBr—, CF3CF2-, (CF3)2CH—, and CF3(SCF3)CH-substituted arenes from 1-(diazo-2,2,2-trifluoroethyl)arenes. *Org. Lett.* 16, 6004-6007 (2014).
38. A. Solovyev, S.-H. Ueng, J. Monot, L. Fensterbank, M. Malacria, E. Lacôte, D. P. Curran, Estimated rate constants for hydrogen abstraction from N-heterocyclic carbene-borane complexes by an alkyl radical. *Org. Lett.* 12, 2998-3001 (2010).
39. X. Li, D. P. Curran, Insertion of reactive rhodium carbenes into boron-hydrogen bonds of stable N-heterocyclic carbene boranes. *J. Am. Chem. Soc.* 135, 12076-12081 (2013).
40. S. Huang, X. Qi, T. Liu, K. Wang, W. Zhang, J. Li, Q. Zhang, Towards safer rocket fuels: hypergolic imidazolylidene-borane compounds as replacements for hydrazine derivatives. *Chem. Eur. J.* 22, 10187-10193 (2016).
41. M.-H. Wang, L.-Y. Chen, An efficient FeCl3-mediated approach for reduction of ketones through N-heterocyclic carbene boranes. *Tetrahedron Lett.* 58, 732-735 (2017).
42. S.-C. Ren, F.-L. Zhang, J. Qi, Y.-S. Huang, A.-Q. Xu, H.-Y. Yan, Y-F. Wang, Radical borylation/cyclization cascade of 1,6-enynes for the synthesis of boron-handled hetero- and carbocycles. *J. Am. Chem. Soc.* 139, 6050-6053 (2017).
43. G. M. Sheldrick, Phase annealing in SHELX-90: Direct methods for larger structures. *Acta Cryst.* A46, 467-473 (1990).
44. G. M. Sheldrick, Crystal structure refinement with SHELXL. *Acta Cryst.* C71, 3-8 (2015).
45. P. Müller, Practical suggestions for better crystal structures. *Crystallogr. Rev.* 15, 57-83 (2009).
46. S. Parsons, H. D. Flack, T. Wagner, Use of intensity quotients and differences in absolute structure refinement. *Acta Cryst.* B69, 249-259 (2013).
47. R. W. W. Hooft, L. H. Strayer, A. L. Spek, Using the t-distribution to improve the absolute structure assignment with likelihood calculations. *J. Appl. Cryst.* 43, 665-668 (2010).
48. Argintaru, O. A., Ryu, D., Aron, I. & Molander, G. A. Synthesis and applications of α-trifluoromethylated akylboron compounds. *Angew. Chem. Int. Ed.* 52, 13656-13660 (2013).
49. Jiang, Q., Guo, T. & Yu, Z. Copper-catalyzed asymmetric borylation: Construction of a stereogenic carbon center bearing both CF3 and organoboron functional groups. *J. Org. Chem.* 82, 1951-1960 (2017).
50. Kanouni, T., Stafford, J. A., Veal, J. M. & Wallace, M. B. Histone demethylase inhibitors. WO 2014/151106 A1.
51. Scopes, D. Pyrrolo[3,2-E][1,2,4]triazolo[1,5-A] pyrimidines derivatives as inhibitors of microglia activation. US 2012/0289523 A1.
52. J.-M. Yang, Z.-Q. Li, M.-L. Li, Q. He, S.-F. Zhu, Q.-L. Zhou, Catalytic B—H bondinsertion reactions using alkynes as carbene precursors. *J. Am. Chem. Soc.* 139, 3784-3789 (2017).
53. D. Sterk, M. Stephan, B. Mohar, Highly enantioselective transfer hydrogenation of fluoroalkyl ketones. *Org. Lett.* 8, 5935-5938 (2006).
54. J. Y. Hamilton, B. Morandi, E. M. Carreira, Homologative trifluoromethylation of acetals. *Synthesis* 45, 1857-1862 (2013).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for producing an organoboron product, the method comprising combining a boron-containing reagent and a carbene precursor in the presence of a heme protein under conditions sufficient to form the organoboron product, wherein:

the heme protein is a cytochrome c comprising all of the amino acid sequence set forth in SEQ ID NO:1, except for one or more mutations at residues corresponding to positions Y71, V75, M89, T98, M99, M100, T101, and M103 of SEQ ID NO: 1;

the carbene precursor is a compound according to Formula I:

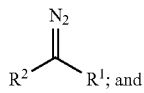

(I)

(i) the boron-containing reagent is a borane-Lewis base complex according to Formula IIa:

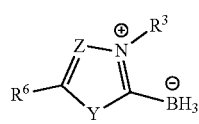

(IIa)

and the organoboron product is a compound according to Formula III:

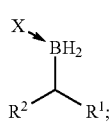

(III)

or (ii) the boron-containing reagent is a boronate ester according to Formula IId:

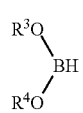

(IId)

and the organoboron product is a compound according to Formula IV:

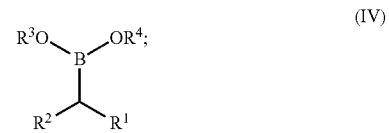

(IV)

wherein
X is:

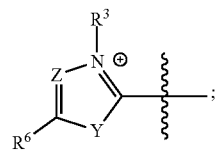

the wavy line represents the point of connection between X and the boron atom in Formula III, Y is selected from the group consisting of $NR^4$, $C(R^4)_2$, O, and S;

Z is selected from the group consisting of N and $CR^5$;

$R^1$ is a $C_{1-6}$ haloalkyl group or $C(O)R^{1a}$, wherein $R^{1a}$ is a $C_{1-6}$ alkyl group or a $C_{1-6}$ alkoxy group; and $R^2$, $R^3$, $R^4$, $R^5$ and $R^6$ are independently selected from the group consisting of H, an optionally substituted $C_{1-18}$ alkyl group, an optionally substituted $C_{1-18}$ alkoxy group, a $C_{1-18}$ haloalkyl group, a $C_{2-18}$ alkenyl group, a $C_{2-18}$ alkynyl group, an optionally substituted $C_{6-10}$ aryl group, a cyano group, and a halo group, wherein the optionally substituted $C_{1-18}$ alkyl group, the optionally substituted $C_{1-18}$ alkoxy group, and the optionally substituted $C_{6-10}$ aryl group are optionally substituted with one or more moeities selected from a halo group, a hydroxy group, an amino group, an alkylamino group, an alkoxy group, a haloalkyl group, a carboxy group, an amido group, a nitro group, an oxo group, and a cyano group.

2. The method of claim 1, wherein $R^2$ is a $C_{1-6}$ alkyl group or a $C_{6-10}$ aryl group.

3. The method of claim 1, wherein $R^1$ is $C(O)R^{1a}$ and $R^{1a}$ is a $C_{1-6}$ alkyl group or a $C_{1-6}$ alkoxy group.

4. The method of claim 1, wherein $R^1$ is a $C_{1-6}$ haloalkyl group.

5. The method of claim 1, wherein the boron-containing reagent is the borane-Lewis base complex according to Formula IIa and the organoboron product is the compound according to Formula III.

6. The method of claim 1, wherein the boron-containing reagent is the boronate ester according to Formula IId and the organoboron product is the compound according to Formula IV.

7. The method of claim 1, wherein the organoboron product is produced enantioselectively.

8. The method of claim 1, wherein the heme protein is expressed in a cell and the organoboron product is produced in vivo.

9. The method of claim 1, wherein the cytochrome c comprises: (i) an M100D mutation, and (ii) a V75R mutation, a V75P mutation, or a V75G mutation.

10. The method of claim 9, wherein the cytochrome c further comprises an M103T mutation, an M103D mutation, or an M103F mutation.

11. The method of claim 9, wherein the cytochrome c further comprises one or more mutations selected from the group consisting of Y71C, M89C, M89F, T98V, M99C, M99L, M99Y, T101A, T101L, and M103F.

* * * * *